United States Patent

Levin et al.

[11] Patent Number: 5,929,097
[45] Date of Patent: *Jul. 27, 1999

[54] PREPARATION AND USE OF ORTHO-SULFONAMIDO ARYL HYDROXAMIC ACIDS AS MATRIX METALLOPROTEINASE AND TACE INHIBITORS

[75] Inventors: Jeremy Ian Levin, Nanuet; Mila T. Du, Suffern; Aranapakam Mudumbai Venkatesan, Rego Park, all of N.Y.; Frances Christy Nelson, Wyckoff, N.J.; Arie Zask, New York; Yansong Gu, Pearl River, both of N.Y.

[73] Assignee: American Cyanamid Company, Madison, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/944,593

[22] Filed: Oct. 6, 1997

Related U.S. Application Data

[60] Provisional application No. 60/028,504, Oct. 16, 1996.
[51] Int. Cl.[6] .................. C07D 213/02; C07C 311/08; A61K 31/18; A61K 31/44
[52] U.S. Cl. .................. 514/351; 514/211; 514/238.2; 514/255; 514/327; 514/338; 514/342; 514/343; 514/424; 514/454; 514/602; 514/604; 540/526; 544/158; 544/384; 546/195; 546/216; 546/278.4; 546/280.1; 546/280.4; 546/283.1; 546/293; 548/565; 549/236; 564/84; 564/90
[58] Field of Search .................. 540/526; 544/158, 544/384; 546/195, 216, 278.4, 280.1, 280.4, 293, 283.1; 548/565; 549/236; 564/84, 90; 514/211, 238.2, 255, 327, 338, 342, 343, 351, 424, 454, 602, 604

[56] References Cited

U.S. PATENT DOCUMENTS

| | | | |
|---|---|---|---|
| 5,455,258 | 10/1995 | MacPherson et al. | 514/357 |
| 5,506,242 | 4/1996 | MacPherson et al. | 514/336 |
| 5,552,419 | 9/1996 | MacPherson et al. | 514/357 |

FOREIGN PATENT DOCUMENTS

| | | |
|---|---|---|
| 606046 | 12/1993 | European Pat. Off. . |
| 757984 | 2/1997 | European Pat. Off. . |
| 780386 | 6/1997 | European Pat. Off. . |
| WO9535275 | 12/1995 | WIPO . |
| WO9535276 | 12/1995 | WIPO . |
| WO9600214 | 1/1996 | WIPO . |
| WO9627583 | 9/1996 | WIPO . |
| WO9633172 | 10/1996 | WIPO . |
| 9719068 | 5/1997 | WIPO . |
| WO9718194 | 5/1997 | WIPO . |
| WO9720824 | 6/1997 | WIPO . |
| WO9722587 | 6/1997 | WIPO . |
| WO9724117 | 7/1997 | WIPO . |
| WO9727174 | 7/1997 | WIPO . |

OTHER PUBLICATIONS

Kato et al, Chemical Abstracts, vol. 126, No. 1, Abstract No. 7829f, p. 872, Jan. 6, 1997.
Priewe et al, Chemical Abstracts, vol. 52, No. 9, Abstract No. 10184d, May 10, 1958.

*Primary Examiner*—Zinna Northington Davis
*Attorney, Agent, or Firm*—Rebecca R. Barrett

[57] ABSTRACT

The present invention relates to the discovery of novel, low molecular weight, non-peptide inhibitors of matrix metalloproteinases (e.g. gelatinases, stromelysins and collagenases) and TNF-α converting enzyme (TACE, tumor necrosis factor-α converting enzyme) which are useful for the treatment of diseases in which these enzymes are implicated such as arthritis, tumor growth and metastasis, angiogenesis, tissue ulceration, abnormal wound healing, periodontal disease, bone disease, proteinuria, aneurysmal aortic disease, degenerative cartilage loss following traumatic joint injury, demyelinating diseases of the nervous system, graft rejection, cachexia, anorexia, inflammation, fever, insulin resistance, septic shock, congestive heart failure, inflammatory disease of the central nervous system, inflammatory bowel disease, HIV infection, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization.

The TACE and MMP inhibiting ortho-sulfonamido aryl hydroxamic acids of the present invention are represented by the formula

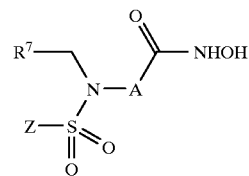

where the hydroxamic acid moiety and the sulfonamido moiety are bonded to adjacent carbons on group A.

11 Claims, No Drawings

PREPARATION AND USE OF ORTHO-SULFONAMIDO ARYL HYDROXAMIC ACIDS AS MATRIX METALLOPROTEINASE AND TACE INHIBITORS

This application claims the benefit of prior U.S. provisional application Ser. No. 60/028,504 flied Oct. 16, 1996.

BACKGROUND OF THE INVENTION

The present invention relates to the discovery of novel, low molecular weight, non-peptide inhibitors of matrix metalloproteinases (e.g. gelatinases, stromelysins and collagenases) and TNF-α converting enzyme (TACE, tumor necrosis factor-α converting enzyme) which are useful for the treatment of diseases in which these enzymes are implicated such as arthritis, tumor metastasis, tissue ulceration, abnormoal wound healing, periodontal disease, bone disease, proteinuria, aneurysmal aortic disease, degenerative cartilage loss following traumatic joint injury, demyelinating diseases of the nervous system and HIV infection.

Matrix metalloproteinases (MMPs) are a group of enzymes that have been implicated in the pathological destruction of connective tissue and basement membranes [Woessner, J. F., Jr. FASEB J. 1991, 5, 2145; Birkedal-Hansen, H.; Moore, W. G. I.; Bodden, M. K.; Windsor, L. J.; Birkedal-Hansen, B.; DeCarlo, A.; Engler, J. A. Crit. Rev. Oral Biol. Med. 1993, 4, 197; Cawston, T. E. Pharmacol. Ther. 1996, 70, 163; Powell, W. C.; Matrsian, L. M. Cur. Top. Microbiol. and Immunol. 1996, 213, 1]. These zinc containing endopeptidases consist of several subsets of enzymes including collagenases, stromelysins and gelatinases. Of these classes, the gelatinases have been shown to be the MMPs most intimtly involved with the growth and speead of tumors, while the collagenases have been associated with the pathogenesis of osteoarthritis [Howell, D. S.; Pelletier, J.-P. In Arthritis and Allied Conditions; McCarthy, D. J.; Koopman, W. J., Eds.; Lea and Febiger: Philadelphia, 1993; 12th Edition Vol. 2, pp. 1723; Dean, D. D. Sem. Arthritis Rheum. 1991, 20, 2; Crawford, H. C.; Matrisian, L. M. Invasion Metast. 1994–95, 14, 234; Ray, J. M.; Stetler-Stevenson, W. G. Exp. Opin. Invest. Drugs, 1996, 5, 323].

It is known that the level of expression of gelatinase is elevated in malignancies, and that gelatnase can degrade the basement membrane which may lead to tumor metastasis [Powell, W. C.; Matrisian, L. M. Cur. Top. Microbiol. and Immunol. 1996, 213, 1; Crawford, H. C.; Matrisian, L. M. Invasion Metast. 1994–95, 14, 234; Ray, J. M.; Stetler-Stevenson, W. G. Exp. Opin. Invest. Drugs, 1996, 5, 323; Himelstein, B. P.; Canete-Soler, R.; Bernhard, E. J.; Dilks, D. W.; Muschel, R. J. Invasion Metast. 1994–95, 14, 246; Nuovo, G. J.; MacConnell, P. B.; Simsir, A.; Valea, F.; French, D. L. Cancer Res. 1995, 55, 267–275; Walther, M. M.; Levy, A.; Hurley, K.; Venzon, D.; Linehen, W. M.; Stetler-Stevenson, W. J. Urol. 1995, 153 (Suppl. 4), 403A; Tokuraku, M; Sato, H.; Murakami, S.; Okada, Y.; Watanabe, Y.; Seiki, M. Int. J. Cancer, 1995, 64, 355; Himelstein, B.; Hua, J.; Bemhard, E.; Muschel, R. J. Proc. Am. Assoc. Cancer Res. Ann. Meet. 1996, 37, 632; Ueda, Y.; Imai, K.; Tsuchiya, H.; Fujimoto, N.; Nakanishi, I.; Katsuda, S.; Seiki, M.; Okada, Y. Am. J. Pathol. 1996, 148, 611; Gress, T. M.; Mueller-Pillasch, F.; Lerch, M. M.; Friess, H.; Buechler, M.; Adler, G. Int. J. Cancer, 1995, 62, 407; Kawashima, A.; Nakanishi, I.; Tsuchiya, H.; Roessner, A.; Obata, K.; Okada, Y. Virchows Arch., 1994, 424, 547–552.]. Angiogenesis, required for the growth of solid tumors, has also recently been shown to have a gelatinase component to its pathology [Crawford, H. C; Matrisian, L. M. Invasion Metast. 1994–95, 14, 234; Ray, J. M.; Stetler-Stevenson, W. G. Exp. Opin. Invest. Drugs, 1996, 5, 323.]. Furthermore, there is evidence to suggest that gelatinase is involved in plaque rupture associated with atherosclerosis [Dollery, C. M.; McEwan, J. R.; Henney, A. M. Circ. Res. 1995, 77, 863; Zempo, N.; Koyama, N.; Kenagy, R. D.; Lea, H. J.; Clowes, A. W. Arterioscler. Thromb. Vasc. Biol. 1996, 16, 28; Lee, R. T.; Schoen, F. J.; Loree, H. M.; Lark, M. W., Libby, P. Arterioscler. Thromb. Vasc. Biol. 1996, 16, 1070.]. Other conditions mediated by MMPs are restenosis, MMP-mediated osteopenias, inflammatory diseases of the central nervous system, skin aging, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premaure rupture of fetal membranes, inflanmatory bowel disease, periodontal disease, age related maclar degeneration, diabetic retinopathy, proliferative vitoretinopathy, retinopathy of prematurity, ocular inflam on, keratoconus, Sjogren's syndrome, myopia, ocular tumors, ocular angiogenesis/neovascularization and corneal graft rejection.

The hypothesis that MMPs are important mediators of the tissue destruction that occurs in arthritis has long been considered, since it was first recognized that these enzymes are capable of degrading collagens and proteoglycans which are the major structural components of cartilage [Sapolsky, A. I.; Keiser, H.; Howell, D. S.; Woessner, J. F., Jr.; J. Clin. Invest. 1976, 58, 1030; Pelletier, J.-P.; Martel-Pelletier, J.; Howell, D. S.; Ghandur-Mnaymneh, L.; Enis, J. E.; Woessner, J. F., Jr., Arthritis Rheum. 1983, 26, 63.], and continues to develop as new MMPs are identified. For example, collagenase-3 (MMP-13) was cloned from breast cancer cells in 1994, and the first report that it could be involved in arthritis appeared in 1995 [Freiji, J. M.; Diez-Itza, L; Balbin, M.; Sanchez, L. M.; Blasco, R.; Tolivia, J.; Lopez-Otin, C. J. Biol. Chem. 1994, 269, 16766; Flannery, C. R.; Sandy, J. D. 102–17, 41st Ann. Meet. Orth. Res. Soc. Orlando, Fla. Feb. 13–16, 1995.]. Evidence is accumulating that implicates MMP-13 in the pathogenesis of arthritis. A major structural component of articulr cartilage, type II collagen, is the preferred substrate for MMP-13 and this enzyme is significantly more efficient at cleaving type II collagen than the other collagenases [Knauper, V.; Lopez-Otin, C.; Smith, B.; Knight, G.; Murphy, G. J. Biol. Chem., 1996, 271, 1544–1550; Mitchell, P. G.; Magna, H. A.; Reeves, L. M.; Lopresti-Morrow, L. L.; Yocum, S. A.; Rosner, P. J.; Geoghegan, K. F.; Hambor, J. E. J. Clin. Invest. 1996, 97, 761.]. MMP-13 is produced by chondrocytes, and elevated levels of MMP-13 has been found in human osteoarthitic tissues [Reboul, P.; Pelletier, J-P.; Hambor, J.; Magna, H.; Tardif, G.; Cloutier, J-M.; Martel-Pelletier, J. Arthritis Rheum. 1995, 38 (Suppl. 9), S268; Shlopov, B. V.; Mainardi, C. L.; Hasty, K. A. Arthritis Rheum. 1995, 38 (Suppl. 9), S313; Reboul, P.; Pelletier, J-P.; Tardif, G.; Cloutier, J-M.; Martel-Pelletier, J. J. Clin. Invest. 1996, 97, 2011]. Potent inhibitors of MMPs were described over 10 years ago, but the poor bioavailability of these arliy peptidic, substrate mimeti MMP inhibitors precluded their evaluation in animal models of arthritis. More bioavailable, non-peptidic MMP inhibitors may be preferred for the treatment of diseases mediated by MMPs.

TNF-α converting enzyme catalyzes the formation of TNF-α from membrane bound TNF-α precursor protein.

TNF-α is a pro inflaoiatory cytokine that is now thought to have a role in rheumatoid arthritis, septic shock, graft rejection, insulin resistance and HIV infection in addition to its well documented antitumor properties. For example, research with anti-TNF-α antibodies and transgenic animas has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. Br. J. Rheumatol. 1995, 34, 334; Pharmaprojects, 1996, Therapeutic Updates 17 (Oct.), au197-M2Z.]. This observation has recently been extended to humans as well. Other conditions mediated by TNF-α are congestive heart failure, cachexia, anorexia, inflammation, fever, irmmrtory disease of the central nervous system, and inflammatory bowel disease.

It is expected that small molecule inhibitors of gelatinase and TACE therefore have the potential for treting a variety of disease states. While a variety of MMP and TACE inhibitors have been identified and disclosed in the literature, the vast majority of these molecules are peptidic or peptide-like compounds that may have bioavailability and pharmacokinetic problems that would limit their clinical effectiveness. Low molecular weight, potent, long-acting, orally bioavailable inhibitors of gelatinases, collagenases and/or TACE are therefore highly desirable for the potential chronic treatment of the above mentioned disease states. Several non-peptidc, sulfur-containing hydroxamic acids have recendy been disclosed and are listed below.

U.S. Pat. Nos. 5,455,258, 5,506,242 and 5,552,419, as well as European patent application EP606,046A1 and WIPO international publications WO96/00214 and WO97/22587 disclose non-peptide matrix metalloproteinase inhibitors of which the compound CGS27023A is representative. The discovery of this type of MMP inhibitor is further detiled by MacPherson, et. al. in J. Med. Chem., (1997),40, 2525. Additional publications disclosing sulfonamide based MMP inhibitors which are variants of the sulfonamide-hydroxamate shown below, or the analogous sulfonamide-carboxylates, are European patent application EP-757984-A1 and WIPO international publications WO95/35275, WO95/35276, WO96/27583, WO97/19068 and WO97/27174.

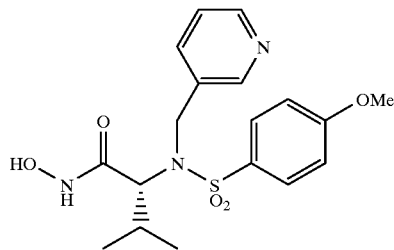

CGS 27023A

Publications disclosing β-sulfonamide-hydroxamate MMP inhibitor analogs of CGS 27023A in which the carbon alpha to the hydroxamic acid has been joined in a ring to the sulfonamide nitrogen, as shown below, include WIPO international publications WO96/33172 and WO97/20824.

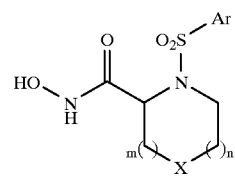

The German patent application DE19,542,189-A1 discloses additional examples of cylic sulfonamides as MMP inhibitors. In this case the sulfonamide-contning ring is fused to a phenyl ring to form an isoquinoline.

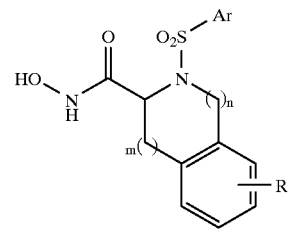

Analogs of the sulfonamide-hydroxamate MMP inhibitors in which the sulfonamide nitrogen has been replaced by a carbon atom, as shown in the general stmcture below, are European patent application EP-780386-A1 and WIPO international publication WO97/24117.

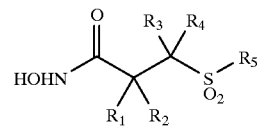

SUMMARY OF THE INVENTION

The TACE and MMP inhibiting orthosulfonamido aryl hydroxamic acids of the present invention are represented by the formula

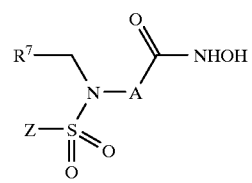

where the hydroxamic acid moiety and the sulfonamido moiety are bonded to adjacent carbons of group A where:

A is phenyl or naphthyl, optionally substituted by $R^1$, $R^2$, $R^3$ and $R^4$;

Z is aryl, heteroaryl, or heteroaryl fused to a phenyl,
  where aryl is phenyl or naphthyl optionally substituted by $R^1$, $R^2$, $R^3$ and $R^4$;
  heteroaryl is a 5–6 membered heteroaromatic ring having from 1 to 3 heteroatoms independently selected from N, O, and S, and optionally substituted by $R^1$, $R^2$, $R^3$ and $R^4$;
  and when heteroaryl is fused to phenyl, either or both of the rings can be optionally substituted by $R^1$, $R^2$, $R^3$ and $R^4$;

$R^1$, $R^2$, $R^3$ and $R^4$ are independently —H, —COR$^5$, —F, —Br, —Cl, —I, —C(O)NR$^5$OR$^6$, —CN, —OR$^5$, —$C_1$–$C_4$-perfluoroalkyl, —$S(O)_xR^5$ where x is 0–2, —$OPO(OR^5)OR^6$, —$PO(OR_6)R_5$, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R_5)SO_2R^6$, —$NR^5CONR^5R^6$, —$NR^5C(=NR^6)$ $NR^5R^6$, 3–6 membered cycloheteroalkyl having one to three heteroatoms independently selected from N, O, and S and optionally having 1 or 2 double bonds and optionally substituted by one to three groups each selected independently from $R^5$; -aryl or heteroaryl as defined above, biphenyl optionally substituted by one to four groups each selected independently from $R^4$, —$SO_2NHCOR^5$ or —$CONHSO_2R^5$ where $R^5$ is not H, -tetrazol-5-yl, —$SO_2NHCN$, —$SO_2NHCONR^5R^6$ or straight chain or branched -$C_1$–$C_6$ alkyl, -$C_2$–$C_6$-alkenyl, or -$C_2$–$C_6$-alkynyl, or -$C_3$–$C_6$-cycloalkyl optionally having 1 or 2 double bonds each optionally substituted with —$COR^5$, —CN, -$C_2$–$C_6$ alkenyl, -$C_2$–$C_6$ alkynyl, —$OR^5$, -$C_1$–$C_4$-perfluoroalkyl, —$S(O)_xR^5$ where x is 0–2, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, -$C_3$–$C_6$cycloalkyl as defined above, 3–6 membered cycloheteroallyl as defined above, aryl or heteroaryl as defined above, biphenyl, —$SO_2NHCOR^5$ or —$CONHSO_2R^5$ where $R^5$ is not hydrogen; —$PO(OR^5)OR^6$, —$PO(OR^6)R^5$, -tetrazol-5-yl, $C(O)NR^5OR^6$, —$NR^5C(=NR^6)$ $NR^5R^6$,—$SO_2NHCONR^5R^6$ or —$SO_2NHCN$;

with the proviso that when $R^1$ and $R^2$ are on adjacent carbons of A, $R^1$ and $R^2$ together with the carbons to which they are attached can form a 5 to 7 membered saturated or unsaturated heterocyclic ring or a 5–6 membered heteroaryl ring, each having 1 to 3 heteroatoms independently selected from O, S, or N, and each optionally substituted by one to four groups each selected independently from $R^4$; or a 5 to 7 membered saturated or unsaturated carbocyclic ring optionally substituted by one to four groups each selected independently from $R^4$;

$R^5$ and $R^6$ are independently H, aryl and heteroaryl as defined above, -$C_3$–$C_6$-cycloalkyl as defined above, -$C_3$–$C_6$-cycloheteroalkyl as defined above, -$C_1$–$C_4$-perfluoroalkyl, or straight chain or branched -$C_1$–$C_6$ alkyl, -$C_2$–$C_6$-alkenyl, or -$C_2$–$C_6$-alkynyl each optionally substituted with —OH, —$COR^8$, —CN, —$C(O)$ $NR^8OR^9$, -$C_2$–$C_6$-alkenyl, -$C_2$–$C_6$-alkynyl, —$OR^8$, -$C_1$–$C_4$-perfluoroakyl, —$S(O)_xR^8$ where x is 0–2, —$OPO(OR^8)OR^9$, —$PO(OR^8)R^9$, —$OC(O)NR^8R^9$, —$COOR^8$, —$CONR^8R^9$, —$SO_3H$, —$NR^8R^9$,— $NCOR^8R^9$, —$NR^8COOR^9$, —$SO_2NR^8R^9$, —$NO_2$, —$N(R^8)SO_2R^9$, —$NR^8CONR^8R^9$, -$C_3$–$C_6$ cycloalkyl as defined above, 3–6 rnembered cycloheteroalkyl as defined above, aryl or heteroaryl as defined above, —$SO_2NHCOR^8$ or —$CONHSO_2R^8$ where $R^8$ is not hydrogen, -tetrazol-5-yl, —$NR^8C(=NR^9)NR^8R^9$, —$SO_2NHCONR^8R^9$, or —$SO_2NHCN$;

$R^7$ is hydrogen, straight chain or branched -$C_1$–$C_6$-alkyl, -$C_2$–$C_6$-alkenyl, or -$C_2$–$C_6$-alkynyl each optionally substituted with —OH, —$COR^5$, —CN, -$C_2$–$C_6$alkenyl,-$C_2$–$C_6$-alkynyl, —$OR^5$,-$C_1$–$C_4$-perfluoroalkyl, —$S(O)_xR^5$ where x is 0–2, —$OPO$ $(OR^5)OR^6$, —$PO(OR^5)R^6$, —$OC(O)NR^5R^6$, —$COOR^5$, —$CONR^5R^6$, —$SO_3H$, —$NR^5R^6$,— $NR^5COR^6$, —$NR^5COOR^6$, —$SO_2NR^5R^6$, —$NO_2$, —$N(R^5)SO_2R^6$, —$NR^5CONR^5R^6$,-$C_3$–$C_6$ cycloalkyl as defined above, -$C_3$–$C_6$-cycloheteroalkyl as defined above, -aryl or heteroaryl as defined above, —$SO_2NHCOR^5$ or —$CONHSO_2R^5$ where $R^5$ is not hydrogen, -tetrazol-5-yl, —$NR^5C(=NR6)NR^5R^6$, —$C(O)N$ $R^5OR^6$, —$SO_2NHCONR^5R^6$ or —$SO_2NHCN$;

or $R^7$ is phenyl or naphthyl, optionally substituted by $R^1$, $R^2$, $R^3$ and $R^4$ or a 5 to 6 membered heteroaryl group having 1 to 3 heteroatoms selected independendy from N, O, and S and optionally substituted by $R^1$, $R^2$, $R^3$ and $R^4$;

or $R^7$ is $C_3$–$C_6$ cycloalkyl or 3–6 membered cycloheteroalkyl as defined above;

or $R^7CH_2$—N—A—, where A is as defined above, can form a non-aromatic 1,2-benzo-fused 7–10 membered heterocyclic ring optionally containing an additional heteroatom selected from O, S and N wherein said heterocyclic ring may be optionally fused to another benzene ring;

$R^8$ and $R^9$ are independently H, aryl or heteroaryl as defined above, -$C_3$–$C_7$-cycloalkyl or 3 to 6 membered cycloheteroalkyl as defined above, -$C_1$–$C_4$-perfluoroalkyl, straight chain or branched -$C_1$–$C_6$-alkyl, -$C_2$–$C_6$-alkenyl, or -$C_2$–$C_6$-alkynyl, each optionally substituted with hydroxy, alkoxy, aryloxy, -$C_1$–$C_4$-perfluoroalkyl, amino, mono- and di-$C_1$–$C_6$-alkylamino, carboxylic acid, carboalkoxy and carboaryloxy, nitro, cyano, carboxamido primay, mono- and di-$C_1$–$C_6$-alkylcarbamoyl;

and the pharmaceutically acceptable salts thereof and the optical isomers and diastremrs thereof.

Preftrred compounds are those wherein both of the carbons of A adjacent to the carbon bearing the sulfonamido group have a substituent other than hydrogen. Also preferrd are compounds where Z is 4-alkoxyphenyl, 4-aryloxyphenyl or heteroaryloxyphenyl.

In the above definitions, the term "heteroaryl" includes, but is not limited to pyrrole, furan, thiophene, pyridine, pyrimidine, pyridazine, pyrazine, triazole, pyrazole, imidazole, isothiazole, thiazole, isoxazole and oxazole. The term "5 to 7 membered saturated or unsaturated heterocyclic ring" includes, but is not limited to oxazolidine, thiazolidine, imidazolidine, tetrahydrofuran, tetrahydrohiophene, tetramethylene sulfone, dihydropyran, tetrahydropyran, piperidine, pyrrolidine, dioxane, morpholine, azepine and diazepine. The term "heteroaryl fused to a phenyl" includes, but is not limited to, benzoxazole, benzoisoxazole, indole, isoindole, benzothiophene, benzofuran, quinoline, quinazoline, quinoxaline, benzotriazole, benzimidazole, benzthiazole, benzopyrazole and isoquinoline.

The following compounds (1–10) which may be used in preparing invention compounds are known and references are given hereinbelow.

1

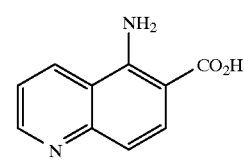

-continued

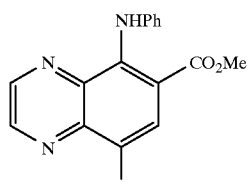

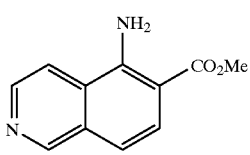

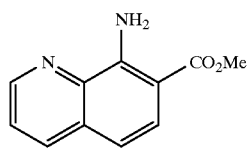

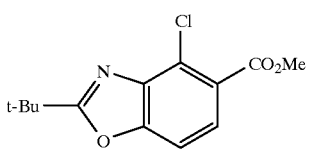

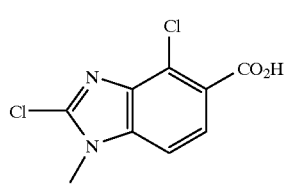

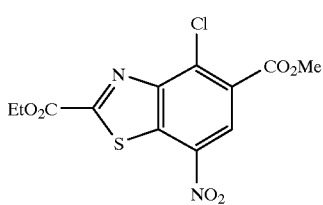

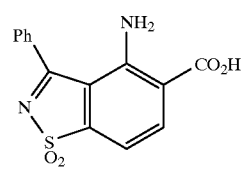

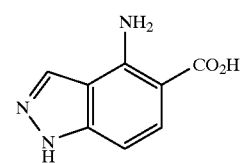

-continued

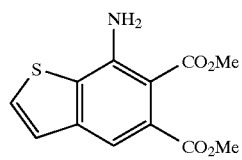

Compound 1:
  a) Meyer, Michael D.; Altenbach, Robert J.; Basha, Fatima Z.; Carroll, William A.; Drizin, Irene; Elmore, Steven W.; Kerwin, Jr James F.; Lebold, Suzanne A.; Lee, Edmund L.; Sippy, Kevin B.; Tietje, Karin R.; Wendt, Michael D. Tricyclic substituted hexahydrobenz[e]isoindole alpha-1 adrenergic antagonists. U.S. Pat. No. 5,597,823. CAN 126:199575.
  b) Meyer, Michael D.; Altenbach, Robert J.; Basha, Fatima Z.; Carroll, William A.; Drizin, Irene; Kerwin, James F., Jr.; Lebold, Suzanne A.; Lee, Edmund L.; Elmore, Steven W.; et al. Preparation of tricyclic substituted benz[e]isoindoles as a1 adrenergic antagonists. PCT Int. Appl WO 9622992 A1 CAN 125:221858.

Compound 2:
  Troll, Theodor, Schmid, Klaus. Preparation and reactions of a 2H-pyrrolo[3,4-b]pyridine and a 2H-pyrrolo[3,4-b]pyrazine. J. Heterocycl. Chem. (1986), 23(6), 1641–4.

Compound 3:
  Meyer, Michael D.; Altenbach, Robert J.; Basha, Fatima Z.; Carroll, William A.; Drizin, Irene; Elmore, Steven W.; Kerwin, Jr James F.; lebold, Suzanne A.; Lee, Edmund L.; Sippy, Kevin B.; Tietje, Karin R.; Wendt, Michael D. Tricyclic substituted hexahydrobenz[e]isoindole alpha-1 adrenergic antagonists. U.S. Pat. No. 5,597,823. CAN 126:199575.

Compond 4:
  a) Meyer, Michael D.; Altenbach, Robert J.; Basha, Fatima Z.; Carroll, William A.; Drizin, Irene; Elmore, Steven W.; Kerwin, Jr James F.; Lebold, Suzanne A.; Lee, Edmund L.; Sippy, Kevin B.; Tietje, Karin R.; Wendt, Michael D. Tricyclic substituted hexahydrobenz[e]isoindole alpha-1 adrenergic antagonists. U.S. Pat. No. 5,597,823. CAN 126:199575.
  b) Meyer, Michael D.; Altenbach, Robert J.; Basha, Fatima Z.; Carroll, William A.; Drizin, Irene; Kerwin, James F., Jr.; Lebold, Suzanne A.; Lee, Edmund L.; Elmore, Steven W.; et al. Preparation of tricyclic substituted benz[e]isoindoles as a1 adrenergic antagonists. PCT Int. Appl. WO 9622992 A1 CAN 125:221858.

Compound 5:
  Geach, Neil; Hawkins, David William; Pearson, Christopher John; Smith, Philip Henry Gaunt; White, Nicolas. Preparation of isoxazoles as herbicides. Eur. Pat. Appl. EP 636622 A1 CAN 122:290845.

Compound 6:
  Kotovskaya, S. K.; Mokrushina, G. A.; Suetina, T. A.; Chupakhin, O. N.; Zinchenko, E. Ya.; Lesovaya, Z. I.; Mezentsev, A. S.; Chernyshov, A. I.; Samoilova, L. N. Benzimidazolyl derivatives of penicillin and cephalosporin: synthesis and antimicrobial activity. Khim.-Farm. Zh. (1989), 23(8), 952–6.

Compound 7:
  Wagner, Klaus. Bactericidal and fungicidal 4chlorobenzothiazoles. Ger. Offen. DE 2136924 CAN 78:111293.

Compound 8:

Eggensperger, Heinz; Diehl, Karl H.; Kloss, Wilfried. 2-Hydroxy-4-alkoxybenzophenones. Ger. DE 1768599 711223. CAN 76:85557.

Compound 9:

Lichtenthaler, Frieder W.; Moser, Alfred. Nucleosides. 44. Benzo-separated pyrazolopyrimidines: expeditious syntheses of [3,4-g]- and [3,4-h]-linked pyrazoloquinazolinones. Tetrahedron Lett. (1981), 22(44), 4397–400.

Compound 10:

Terpstra, Jan W.; Van Leusen, Albert M. A new synthesis of benzo[b]thiophenes and benzo[c]thiophenes by annulation of disubstituted thiophenes. J. Org. Chem. (1986), 51(2), 230–8.

The compounds of this invention are shown to inhibit the enzymes MMP-1, MMP-9, MMP-13 and TNF-α converting enzyme (TACE) and inhibit cartilage weight loss and collegen content loss in-vivo are therefore useful in the treatment of arthritis, tumor metastasis, tissue ulceration, abnormal wound healing, periodontal disease, bone disease and HIV infection.

DETAILED DESCRIPTION OF THE INVENTION

The invention compounds are prepared using conventional techniques known to those skilled in the art of organic synthesis. The following scheme (Scheme I) illustrtes the general reaction sequence employed. For purposes of illustration only, wherein the group A shown is a phenyl, methyl anthranilate is reacted with p-methoxybenzenesulfonyl chloride to provide the requisite N-aryl sulfonamido-ester which is then alkylated to provide the N,N-disubstituted sulfonamide and subsequently converted into the corresponding hydroxamic acid in two further steps.

Basic salts of the hydroxamic acids can be formed with pharmaceutically acceptable alkli-forming metal cations such as lithium, sodium, potassium, calcium and aluminum. Acid addition salts can be formed when a substitutent contains a basic amino group using a pharmaceutically acceptable inorganic or organic acid such as hydrochloric, hydrobromic, phosphoric, sulfuric, acetic, benzoic, succinic, lactic, malic, maleic, fumaric or methanesulfonic acids.

Where the requisite anthranilic acid is not available, certain invention compounds are prepared by various procedures as shown in the following schemes. In some of the schemes, cerain conversions are not detailed but are understood to incorporate reactions denoted in a previous scheme. In certain reaction sequences a substituent R is not further identified by a number, but the identification of the substituent can readily be ascertained those skilled in the art by referring to the definitions of the various substituents in the generic formula above.

Scheme II below shows the synthetic route used to prepare the 3-trifluoromethyl compound of Example 125 via displacement of an ortho-fluorobenzonitrile.

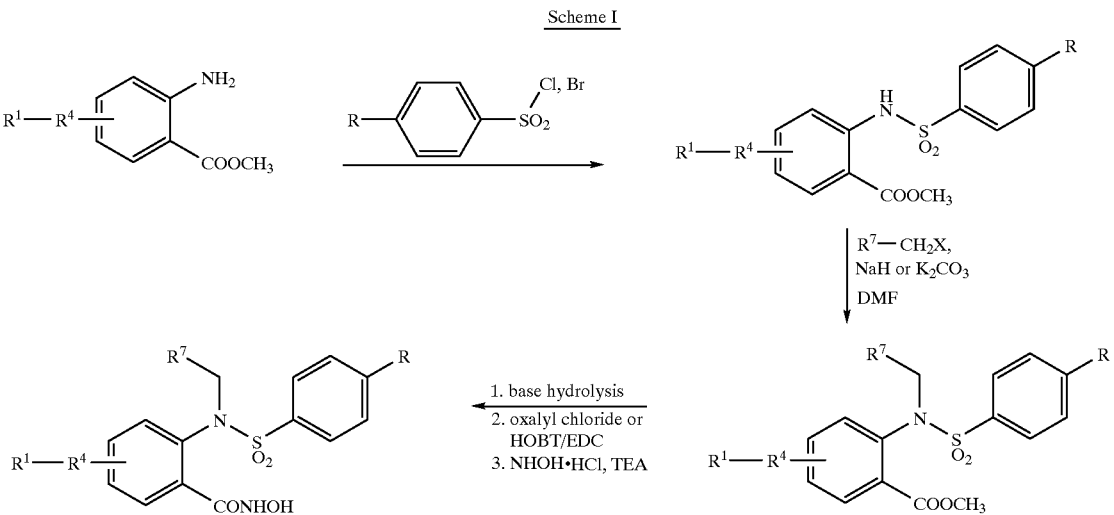

Scheme I

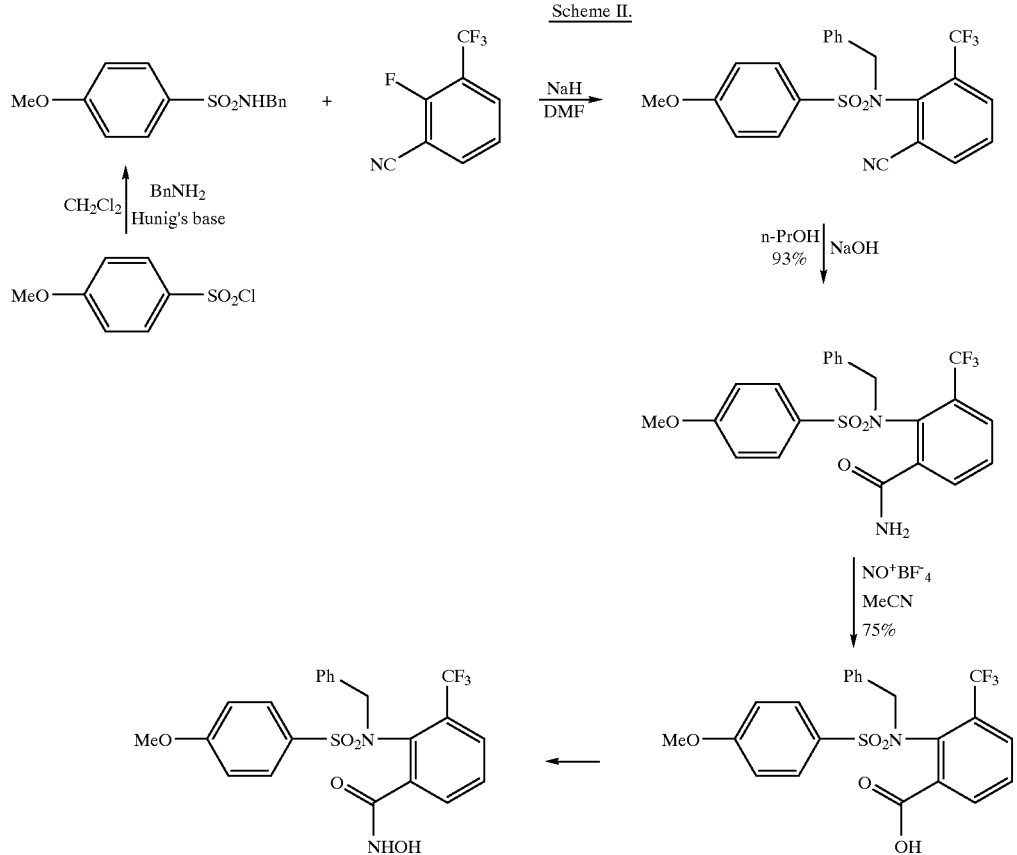

Scheme II.

Synthesis of 3- and 5-aryl and heteroaryl analogs was accomplished following the procedures shown in Schemes III and IV. In both schemes the aryl/heteroaryl group may be appended through the use of Stille or Suzuki palladium catalyzed coupling reactions. As shown in Scheme IV, the palladium catalyzed Stille or Suzuki couplings at the 5-position of the antanilic acid ring can be done before or after the alkylation of the sulfonamide nitrogen.

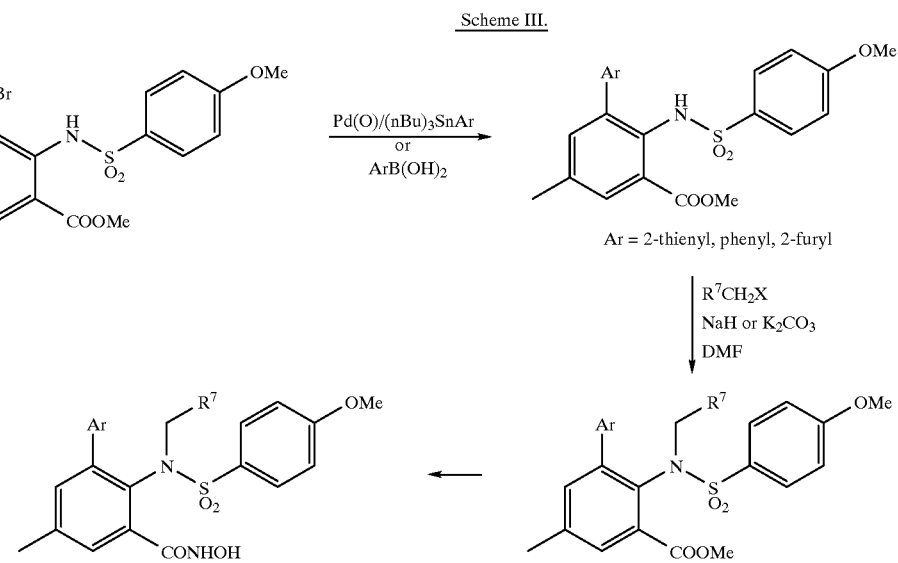

Scheme III.

Ar = 2-thienyl, phenyl, 2-furyl

Scheme IV

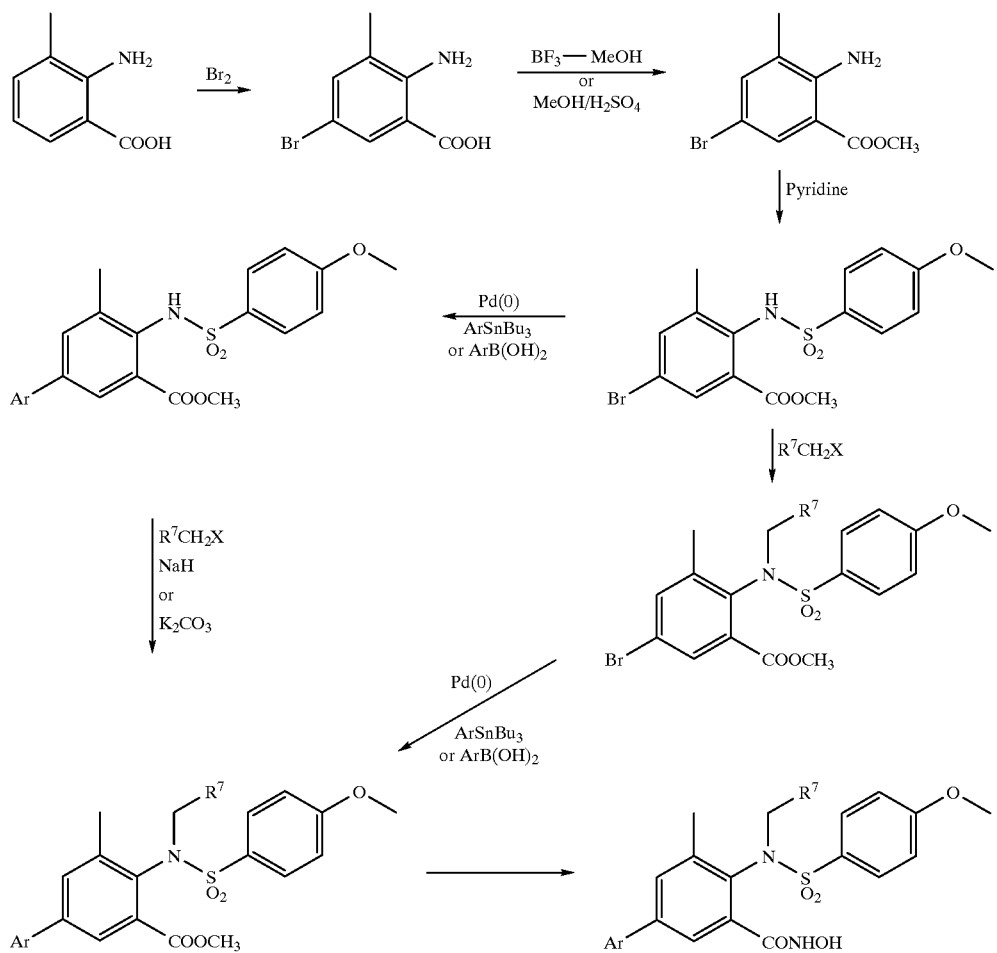

As shown in Scheme V, a Stille coupling of the 5-bromoaryl derivative, prepared as in Scheme IV, with a vinyl stannane provides access to the 5-substituted anthranilic acids bearing a wide variety of functionality including, but not limited to alkenes, allkes, hydroxamic acids, alcohols, halogens and amines. All of the ester derivatives shown in the Scheme may then be converted into the requisite hydroxamic acids.

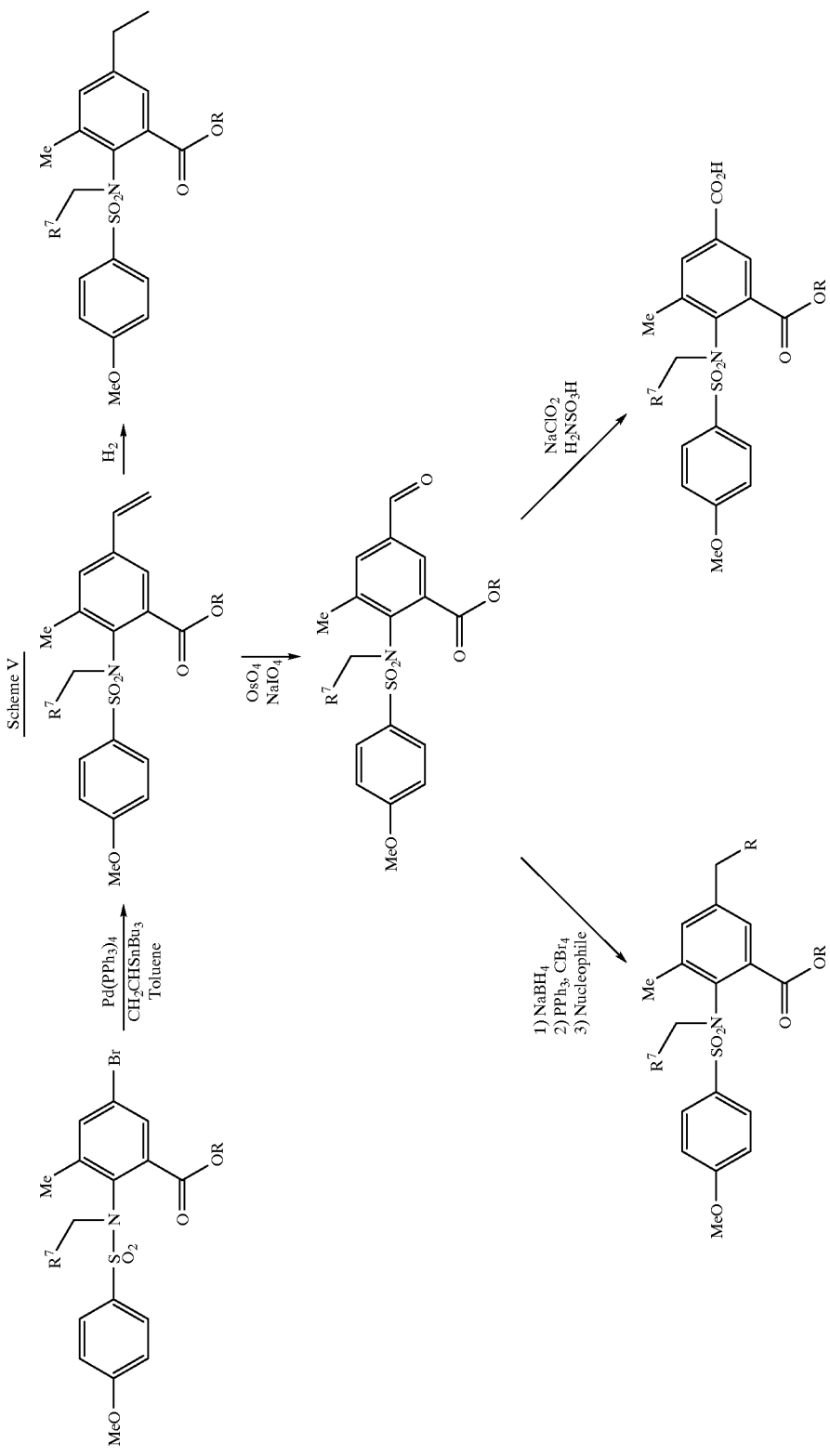

The 5-position of the anthranilic acid ring can also be functionalized through the use of padium caalyzed Heck reactions, as shown in Scheme VI. Thus, reaction of the 5-bromo aryl derivative, prepared as in Scheme IV, with an acrylamide, acrylic acid or acrylic ester provides the 5-cinnamate derivatives, which may then be manipulated and converted into the aryl-hydroxamic acids by known procedures. These cinnarates may also be hydrogenated to give the phenethyl derivatives prior to conversion into the aryl-hydroxamic acids. A variety of substituents are tolerated on the anthranilic acid ring for these transformations and the scheme is presented solely for illustrative purposes.

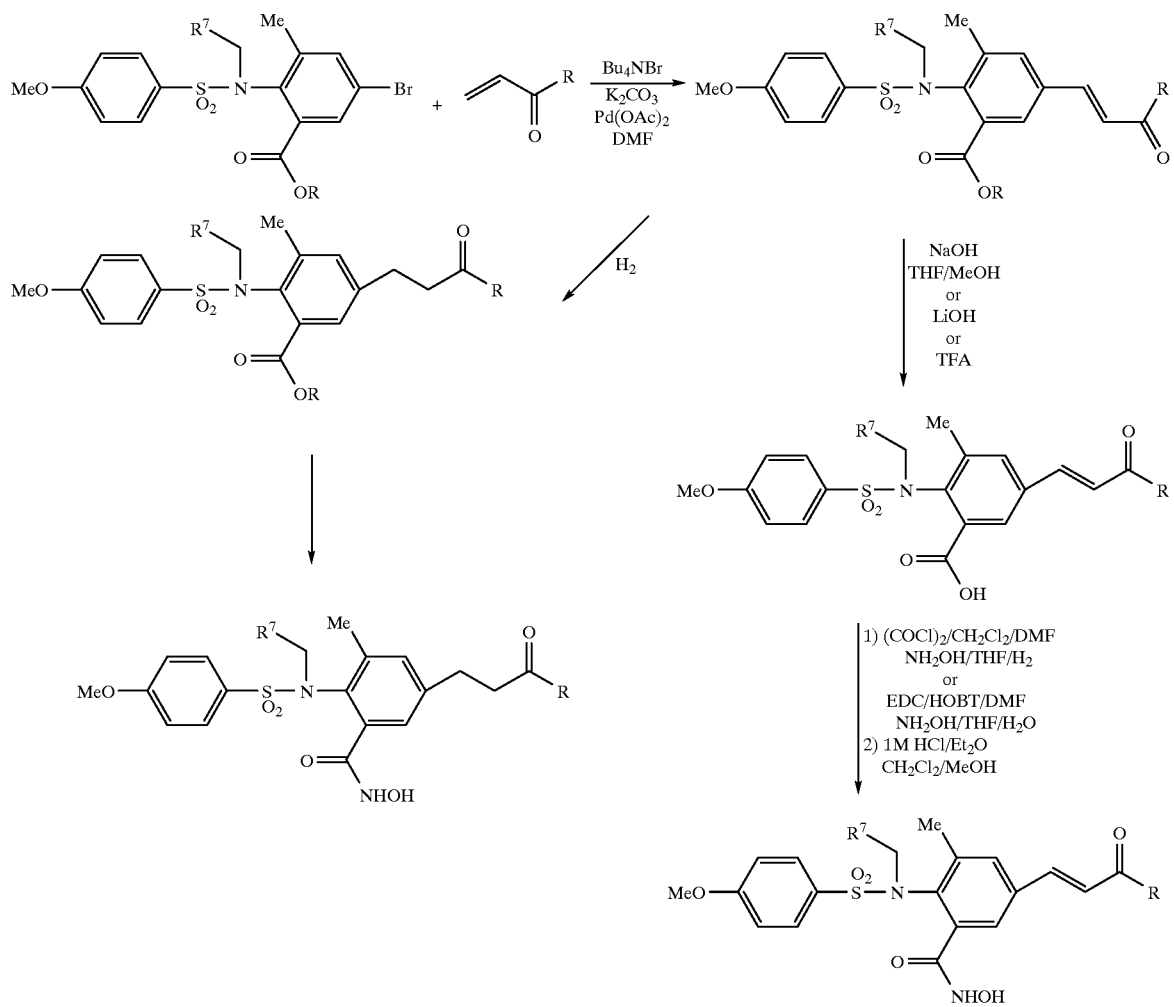

An additional route to anthrnilic acid derivatives substituted at the 5-position, via palladium catalyzed couplings of the aryl halide with alkynes, is shown in Scheme VII. Again, conversion of the aryl esters into the hydroxamates is not shown.

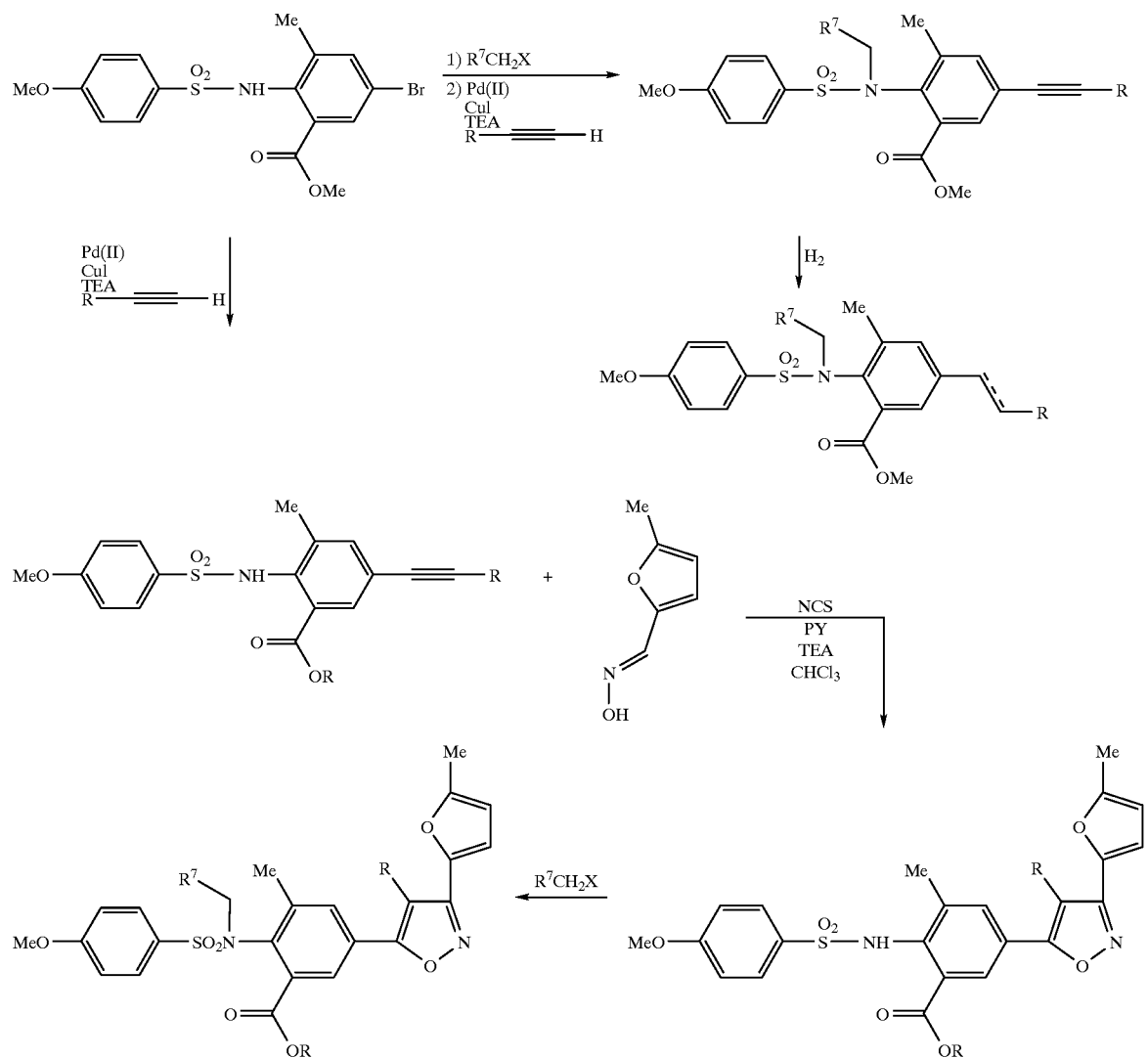

Schemes VIII and IX illustrate routes to anthanilic acid derivatives bearing amine-containing functionality at the 3-position of the anthanilic acid ring. The intiate benzylic bromides can also be diplaced with malonte anion or other carbon-based nucleophiles. The 5-substituent of the anthranilate may be manipulated before or after the amino group is added to the molecule.

Scheme VIII.
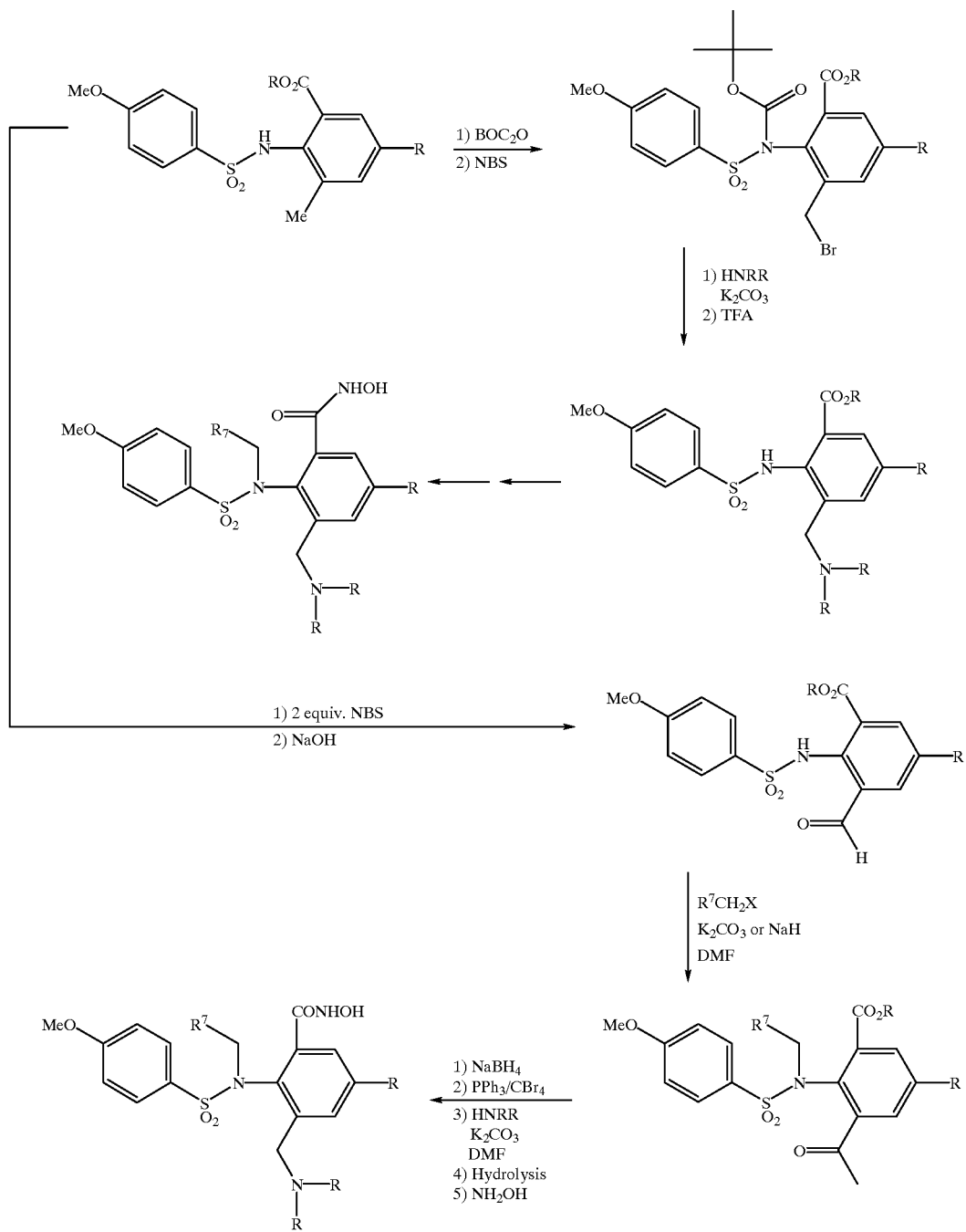

Scheme IX.
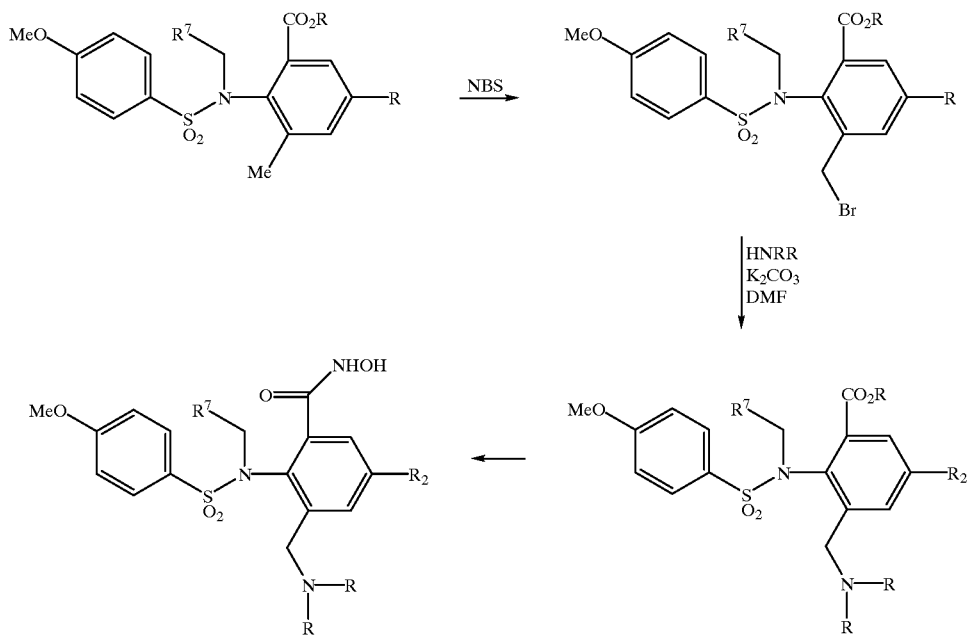
Scheme X shows the route used for the synthesis of 3,6-disubstituted anthranilic acid derivatives. Thus, the ester is converted into the hydroxamic acid by reduction to the alcohol followed by stepwise oxidation to the aldehyde and then the carboxylic acid. The carboxylic acid is then transferred into the hydroxamic acid by the usual procedures.
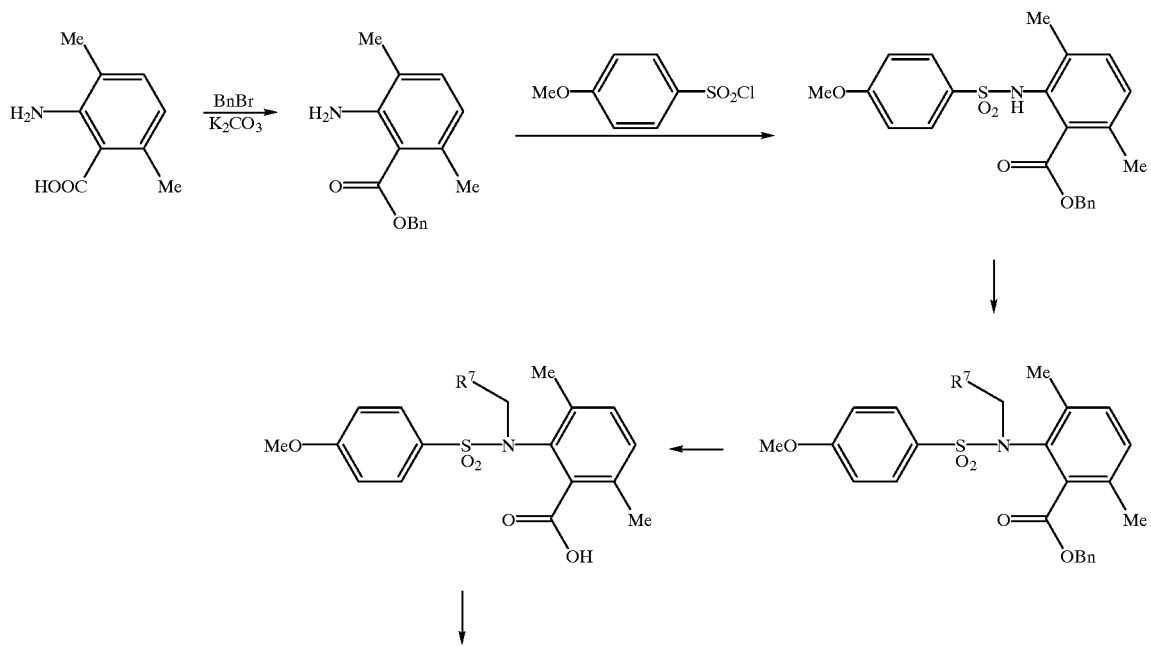

-continued

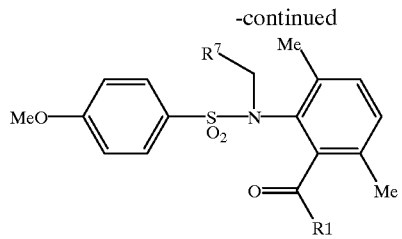

Schemnes XI and XII illustrate two methods for incorporating amino groups into the substituent attached to the sulfonamide nitrogen of the compounds of the invention. Thus, in Scheme XI the NH-sulfonamide is alkylated with propargyl bromide to provide the propargyl sulfonamide. This alkyne is reacted with paraformaldehyde in the presence of a lopimr or secondary amine and cuprous chloride to give the propargyl amine which is converted, as before, to the desired hydroxamnic acid.

In Scheme XII, selective hydrolysis of the ester of the p-carboethoxybenzyl sulfonamide group provides a monocarboxylic acid. This acid may be converted into an amide (not shown), followed by conversion of the anthranilate into the corresponding hydroxamate, or reduced to the corresponding alcohol with diborane. The alcohol may be converted into the analogous amine via the benzylic bromide, followed by conversion of the anthranilate into the corresponding hydroxamate.

Scheme XI.

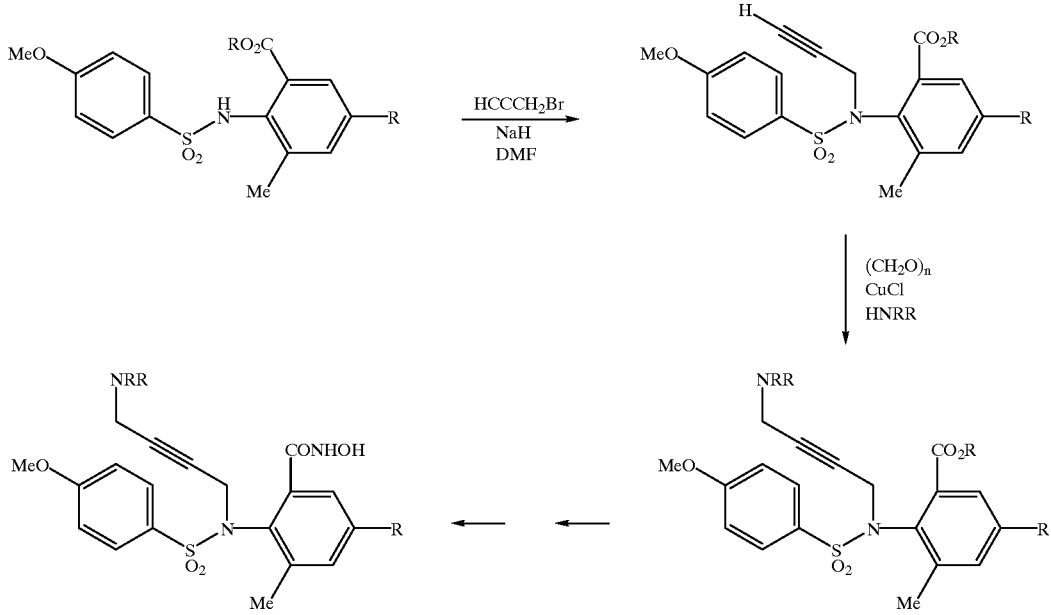

Scheme XII.

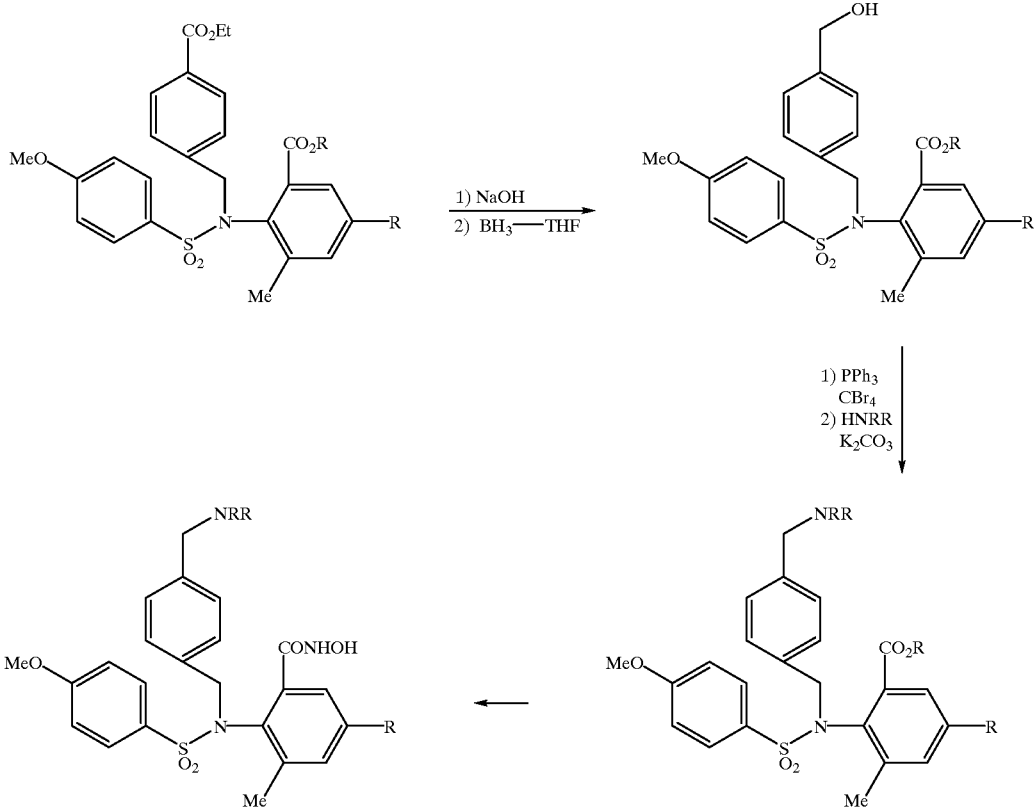

Amine substituents on the anthranilic acid are also available via the 3-nitro anthranilate derivative, as shown in Scheme XIII. The $R^7CH_2$— group is added after the nitration reaction.

Palladium catalyzed couplings of the aryl bromides with the desired amines, as shown in Scheme XIV, can also be used to incorporate amnino groups into the anthranilate ring. When R7 in Scheme XIV is a bromoaryl group, this meth- Scheme XIII.

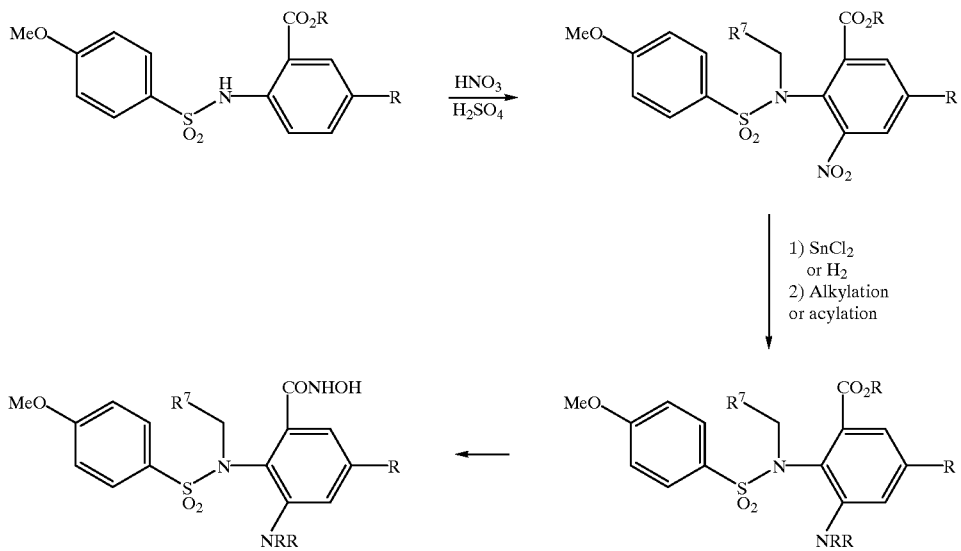

odology may also be used to generate the analogous aminoaryl derivative.

Scheme XIV.

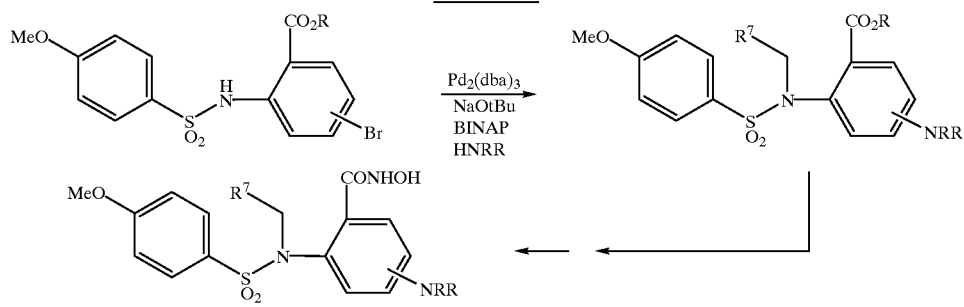

The manipulation of the 3-carboxaldehyde substituent, prepared as shown in Scheme VIII, to append alcohols, ethers and esters at the 3-position of the anthranilic acids is shown in Scheme XV. The carboxylic acid product of the sodium chlorite/sulfamic acid oxidation shown in this scheme may also be used to synthesize carboxamides. The methods illustrated here are applicable to substituents at any position of the anthranilate.

Scheme XV.

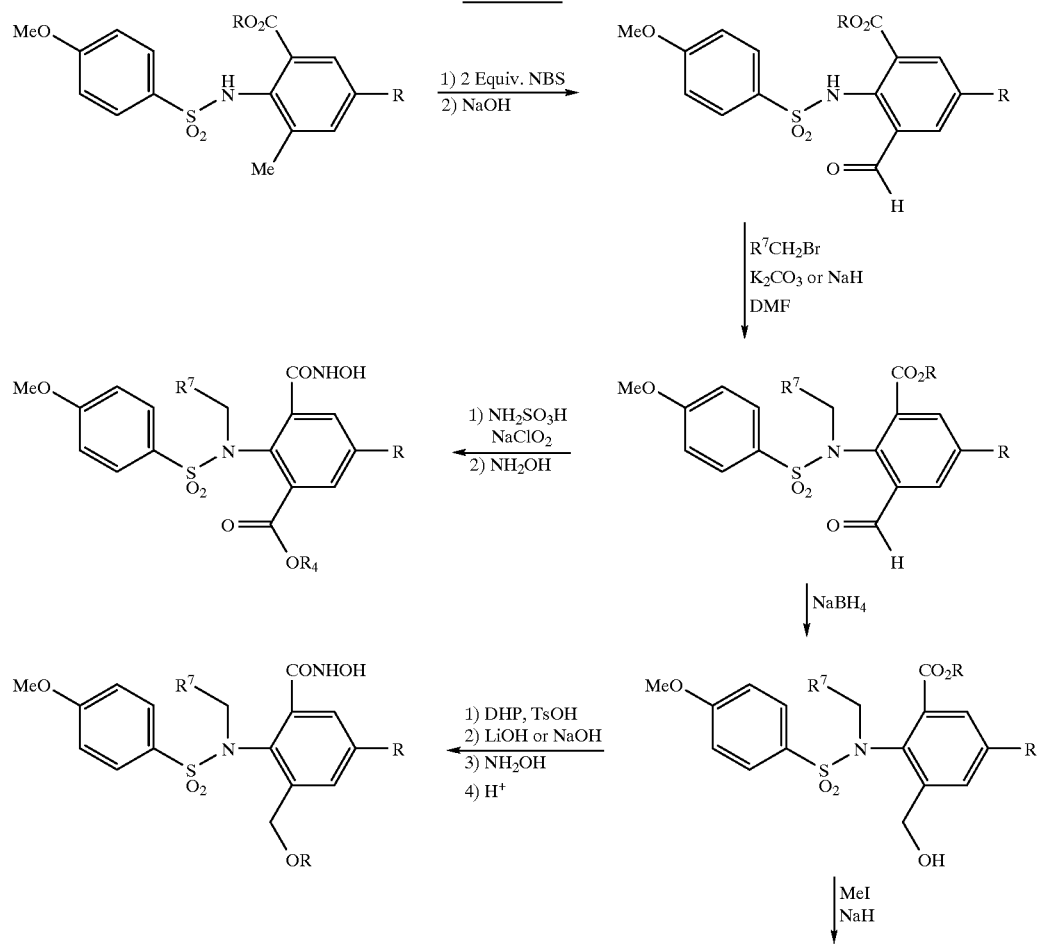

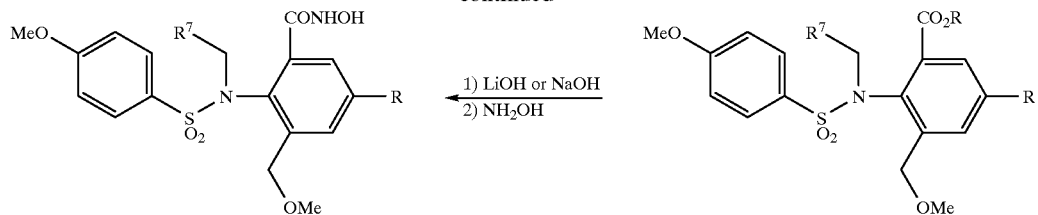
Scheme XVI shows the route used to prepare 3-alkoxy and substituted alkoxy compounds (Examples 34, 54–60, 101, 174)
Scheme XVII shows the route used to prepare benzoic acid ester intermediates of the invention compounds where $R^7$-N-A forms a non-aromatic heterocyclic ring.
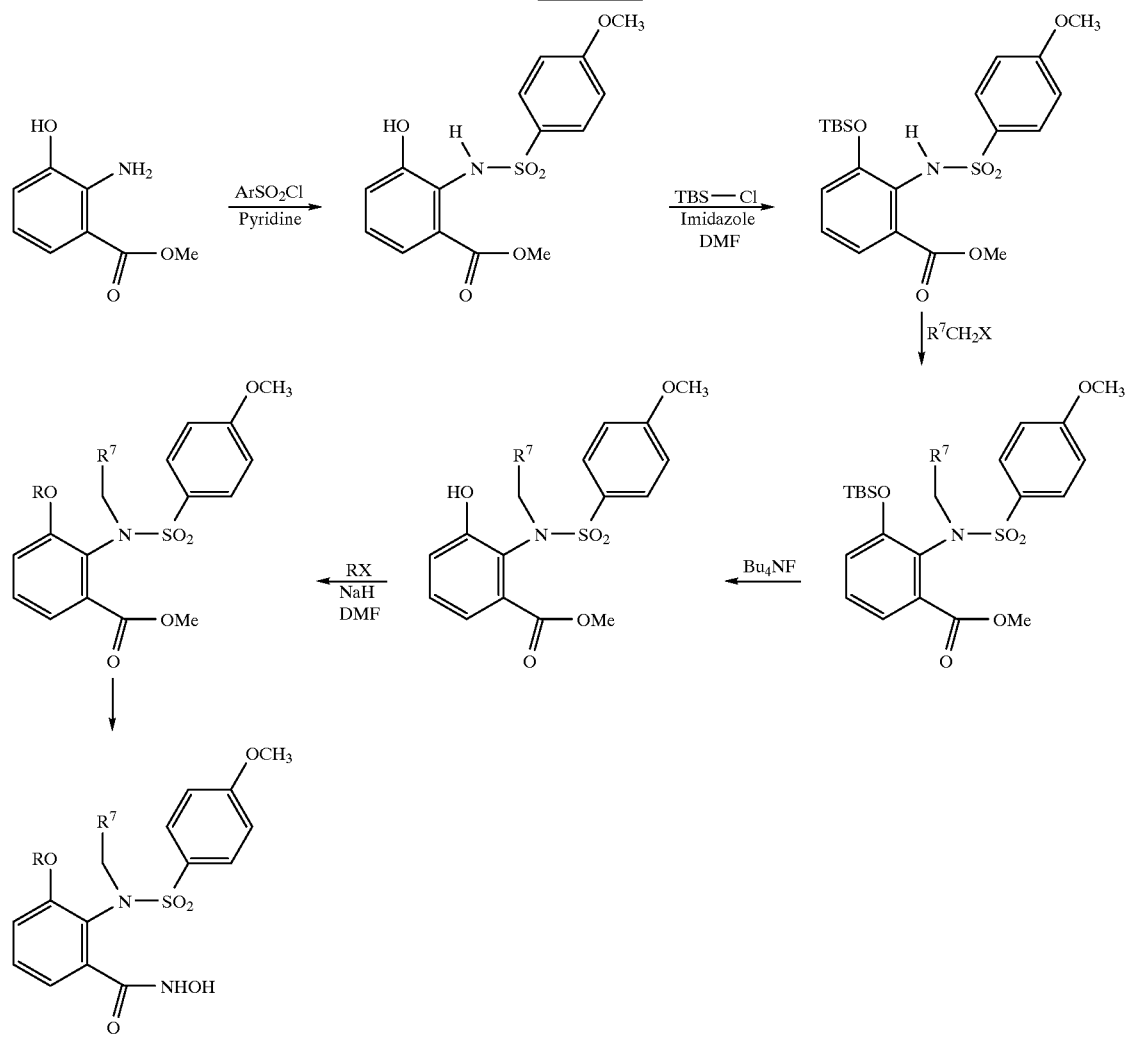

Scheme XVII.

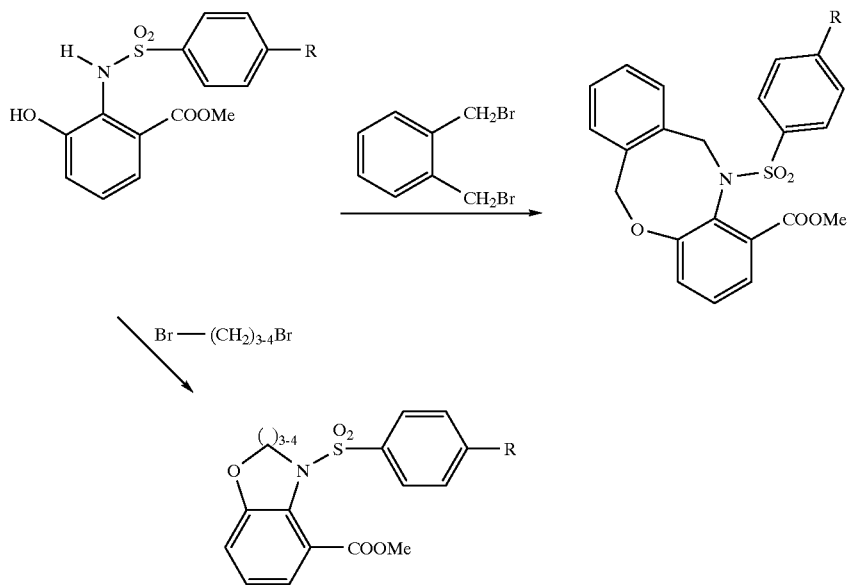

Methods for synthesizing variations of substituents on the sulfonyl aryl group are shown in Schemes XVIII through XXI. As shown in Scheme XVIII, biaryl sulfonyl groups are synthesized by Suzuki couplings on a bromo-substituted benzene sulfonamide. The starting bromo-substituted benzene sulfonamide is synthesized from the commercially available bromobenzenesulfonyl chloride and the anthranilate ester.

Methods for synthesizing sulfonyl aryl ethers are shown in Schemes XIX through XXI. In Scheme XIX biaryl ethers, or aryl heteroaryl ethers, are synthesized starting from the known sulfonyl chlorides (see for example: Zook SE; Dagnino, R; Deason, ME, Bender, SL; Melnick, MJ WO 97/20824).

Scheme XVIII.

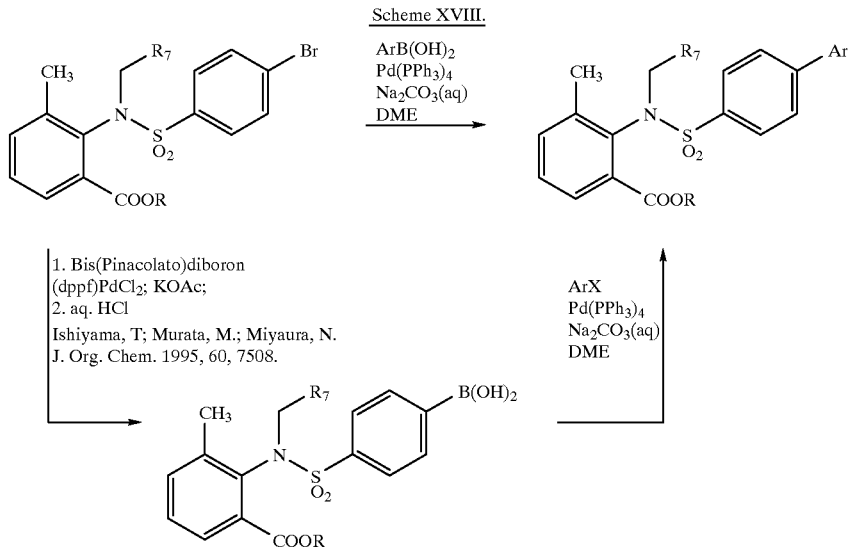

Scheme XIX.
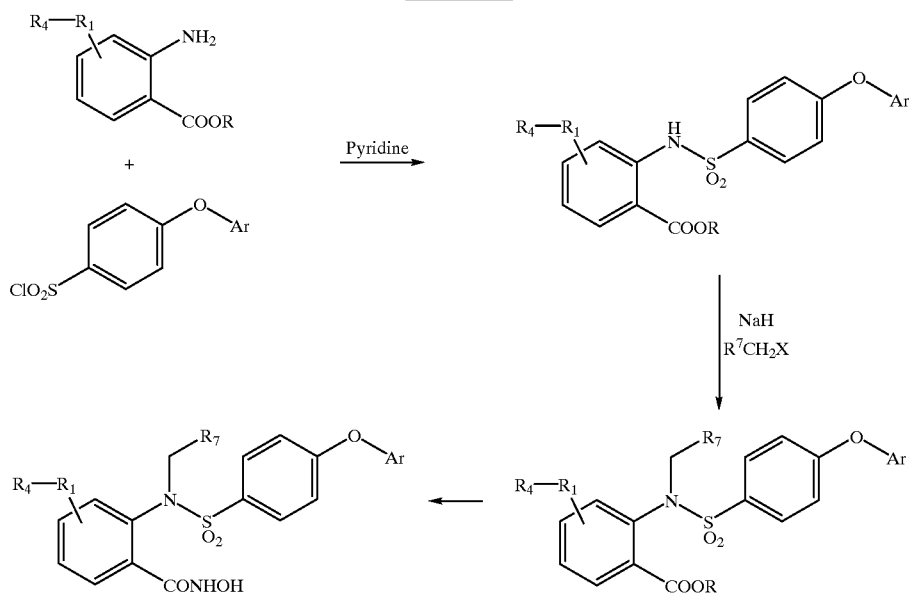
Alternatively, the biaryl ethers may be prepared from the corresponding boronic acids or via the sulfonyl phenols as shown in Scheme XX.
in Scheme XXI. Aryl or alkyl ethers may be prepared in this manner.
Scheme XX.
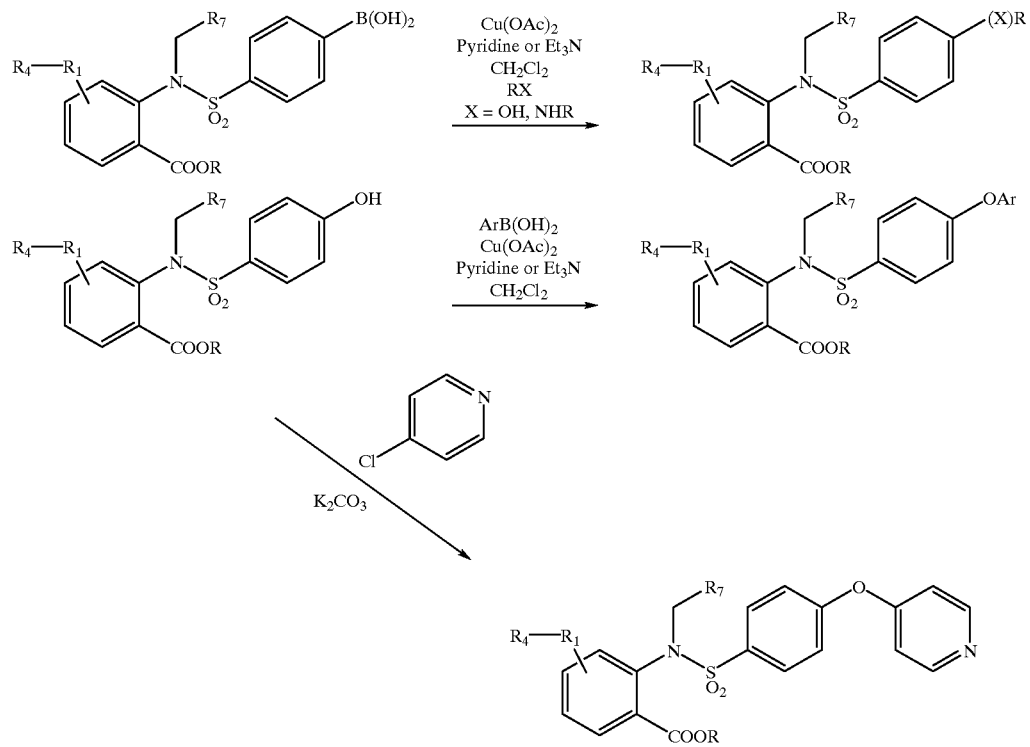
Aryl ethers may also be prepared via displacement of the fluorine from a para-fluorobenzene sulfonamide, as shown Scheme XXI.

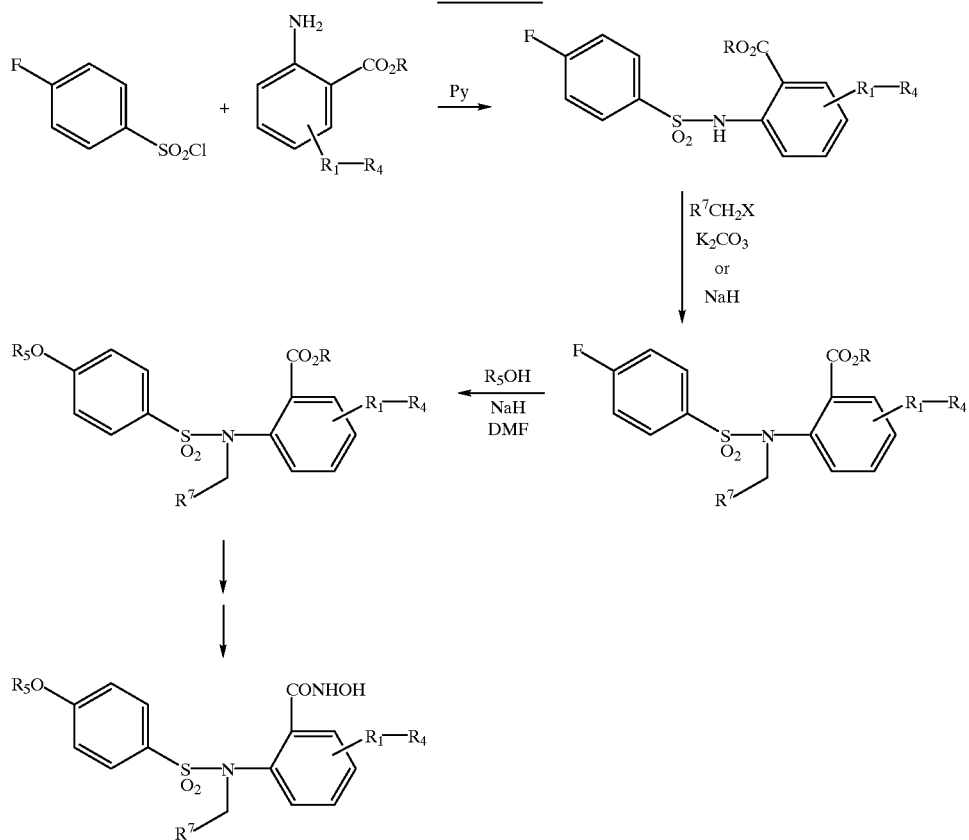

The procedure for the solid-phase synthesis of the compounds of the invention is illustrated in Scheme XXII. Thus, reaction of the resin-linked hydroxylamine, 4, with the pentafluorophenyl ester, 6, gives the resin-linked hydroxamic acid, 7. Sulfonylation of this compound followed by Mitsunobu type alkylation of the sulfonamide then gives compound 9 which is next cleaved from the resin by treatment with trifluoroacetic acid.

Scheme XXII.

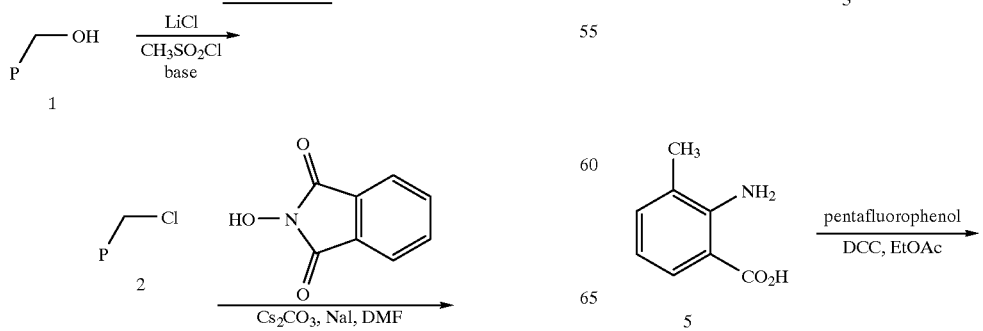

-continued

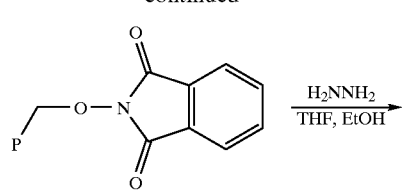

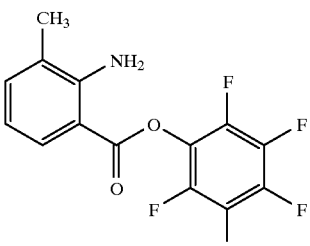

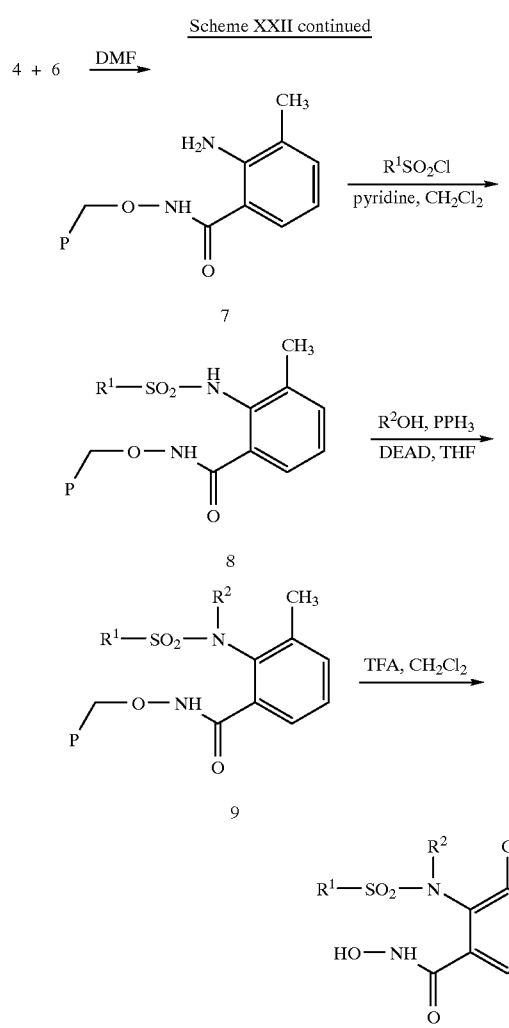

The following specific examples are included for illustrative purposes and are not to be construed as limiting to this disclosure in any way. Other procedures useful for the preparation of the compounds of this invention will be apparent to those skilled in the art of synthetic organic chemistry.

EXAMPLE 1

2-(4-Methoxy-benzenesulfonylamino)-benzoic acid methyl ester

To a solution of 2.00 g (0.013 mol) of methyl anthilt dissolved in 20 mL of chloroform was added 3.2 mL (0.039 mol) of pyridine followed by 2.733 g (0.013 mol) of p-methoxybenzenesulfonyl chloride. The reacon mixture was stirred at room temperature for 5 h and then washed with 3N HCl and water. The organics were then dried over $Na_2SO_4$, filtered and concentrated in vacuo. The resulting white solid was washed with ether and dried in vacuo to provide 3.7 g (87%) of the desired sulfonamide. CI Mass Spec: 322 (M+H).

EXAMPLE 2

3-Chloro-2-(4-methoxybenzenesulfonylamino)-benzoic acid methyl ester

In the same manner as described in Example 1, 4.07 g (0.022 mol) of methyl-3-chloro-anthranilate provided 0.932 g (12%) of the desired sulfonamide as a white solid.

EXAMPLE 3

2-(4-Methoxy-benzenesulfonylamino)-3-methyl-benzoic acid methyl ester

In the same manner as described in Example 1, 6.24 g (0.038 mol) of methyl-3-methyl-anthranilate provided 6.21 g (49%) of the desired sulfonamide as a white solid. Electrospray Mass Spec 336.2 (M+H).

EXAMPLE 4

2-(4-Methoxy-benzenesulfonylamino)-4-methyl-benzoic acid

To a room temperature solution of 2-amino-4-methyl benzoic acid (1.93 g, 12.8 mmol) in 20 ml of dioxane:$H_2O$ (1:1) containing triethylamine (2.68 ml, 19.2 mmol), was added 4-methoxybenzenesulfonyl chloride (2.91 g, 14.1 mmol). The mixture was stired at rt for 18 hr. The resulting mixture was diluted with methylene chloride, washed with 1N HCl, $H_2O$, brine, dried and concentrated. The crude liquid was triturated with 16 ml of EtOAc: hexane (1:3) to afford 2.358 g of the desired product as a white solid (57%). Electrospray Mass Spec 322 (M+H).

EXAMPLE 5

2-(4-Methoxy-benzenesulfonylamino)-6-methyl-benzoic acid

In the same manner as described in Example 4, 1.93 g of 2-amino-6-methylbenzoic acid (12.8 mmol) gave 2.24 g (55%) of the desired sulfonamide product as a white solid after silica gel chromatography (2% MeOH-0.1% AcOH in $CH_2Cl_2$). Electrospray Mass Spec: 322 (M+H).

EXAMPLE 6

2-(4-Methoxy-benzenesulfonylamino)-3-methyl-benzoic acid

In the same manner as described in Example 4, 1.93 g of 2-amino-3-methylbenzoic acid (12.8 mmol) gave 2.07 g (50%) of the desired sulfonamide as a white solid after trituration with EtOAc: hexane (1:4). EI Spec: 321 (M$^+$).

EXAMPLE 7

2-(4-Methoxy-benzenesulfonylamino)-5-methyl-benzoic acid

In the same manner as described in Example 4, 1.93 g of 2-amino-5-methylbenzoic acid (12.8 mmol) gave 2.498 g

41

(61%) of the desired sulfonamide as a white solid after trituration with $CH_2Cl_2$: hexane (1:2). Electrospray Mass Spec: 320 (M−H).

EXAMPLE 8

2-[Benzyl-(4-methoxy-benzenesulfonyl)-amino]-benzoic acid benzyl and methyl esters To a solution of 1.00 g (3.12 mmol) of the product of Example 1 in 45 mL of DMF was added 0.37 mL (3.12 mmol) of benzyl bromide and 3.23 g (0.023 mol) of potassium carbonate. The reaction was heated to reflux for 24 h and an additional 1.11 mL of benzyl bromide was added and the reaction mixture was heated to reflux for another 48 h, then cooled to room temperature and diluted with 400 mL of water. The resulting mixture was extracted with ether and the combined organic layers were then washed with water and brine, dried over $MgSO_4$, filtered and concentrated in vacuo. The residue was chromatographed on silica gel eluting with EtOAc/Hex (1:10) to provide 0.60 g (40%) of the benzyl ester (CI Mass Spec: 488 (M+H)), which gave white crystals on trituration with ether, and 0.57 g (44%) of the methyl ester (CI Mass Spec: 412 (M+H)).

EXAMPLE 9

2-[Benzyl-(4-methoxy-benzenesulfonyl)-amino]-3-chloro-benzoic acid methyl ester

To a solution of 0.90 g (2.532 mmol) of the product of Example 2 in 10 mL of DMF was added 0.127 g (3.165 mmol) of 60% sodium hydride. The resulting mixture was stirred for 30 min at room temperatue and then 0.38 mL (3.165 mmol) of benzyl bromide was added. This reaction mixture was stirred overnight at room temperature, poured into water and then extracted with ether. The combined organics were washed with water and brine, dried over $MgSO_4$, filtered and concentrated in vacuo to provide a white solid which was recrystallized from EtOAc/liexanes to provide 0.44 g (39%) of the desired product as white crystals. CI Mass Spec: 446 (M+H).

EXAMPLE 10

5-Bromo-2-(4-methoxy-benzenesulfonylamino)-3-methyl-benzoic acid methyl ester

To a solution of 1.00 g (2.985 mmol) of the product of Example 3 in 100 mL of $CHCl_3$ was added 0.531 g (2.985 mmol) of N-bromosuccinimide and 0.025 g of AIBN. The resulting mixture was heated to reflux for 18 h and then an additional 0.411 g of NBS and 0.013 g of AIBN were added to the reaction. After refluxing the reaction for another 5 h the reaction mixture was cooled to room temperature, washed with sodium sulfite solution and water, dried over $MgSO_4$, filtered and concentrated in vacuo. The residue was triturated with ether-hexanes to provide 0.62 g (50%) of the desired product as a white solid. EI Mass Spec 413 ($M^+$).

EXAMPLE 11

2-[Benzyl-(4-methoxy-benzenesulfonyl)-amino]-5-bromo-3-methyl-benzoic acid methyl ester In the same manner as described in Example 9, 0.463 g (1.118 mmol) of the product of Example 10 provided 0.514 g (91%) of the desired product as a colorless oil after chromatography on silica gel eluting with EtOAc/Hexanes (1:10). CI Mass Spec: 504 (M+H).

EXAMPLE 12

2-[Benzyl-(4-methoxy-benzenesulfonyl)-amino]-4-methyl-benzoic acid benzyl ester

To a solution of 1.82 g (5.66 mmol) of the product of Example 4 in 20 ml DMF, was added NaH (60% suspension in oil, 498 mg, (12.5 mmol). The resulting mixture was stirred for 15 minutes and benzyl bromide (4.84 g, 0.028 mol) was then added. The mixture was heated to 80–84° with stirnng for 18 hr under $N_2$. The motion was then cooled to room temperature, diluted with ether, washed with $H_2O$ and brine, dried over $MgSO_4$ and concentrated in vacuo. The residue was triturated with EtOAc to afford 2.2 g (77%) of the desired product as a white solid. Electrospray Mass Spec: 502 (M+H).

EXAMPLE 13

2-[Benzyl-(4-methoxy-benzenesulfonyl)-amino]-6-methyl-benzoic acid benzyl ester

In the same manner as described in Example 12, 1.45 g (4.5 mmol) of the product of Example 5 gave 1.18 g (52%) of the desired product as a white solid after silica gel chromatography eluting with EtOAc:hexane (1:9). Electrospray Mass Spec: 502 (M+H).

EXAMPLE 14

2-[Benzyl-(4-methoxy-benzenesulfonyl)-amino]-3-methyl-benzoic acid benzyl ester

In the same manner as described in Example 12, 1.6 g (5.00 mmol) of the product of Example 6 gave 1.269 g (50%) of the desired product as a white solid after silica gel chromatography eluting with EtOAc:Hexane (1:9). CI Mass Spec: 502 (M+H).

EXAMPLE 15

2-[Benzyl-(4-methoxy-benzenesulfonyl)-amino]-5-methyl-benzoic acid benzyl ester

In the same manner as described in Example 12, 1.821 g (5.66 mmol) of the product of Example 7 gave 2.13 g (75%) of the desired product as a white solid after silica gel chromatogrrphy eluting with EtOAc:Hexane (1:5). Electrospray Mass Spec: 502 (M+H).

EXAMPLE 16

2-[Benzyl-(4-methoxy-benzenesulfonyl)-amino]-benzoic acid

To a mixture of 0.60 g (0.123 mmol) of benzyl ester and 0.57 g (0.139 mmol) of methyl ester of Example 8 dissolved in 30 mL of methanol and30 mL of THF was added 30 mL of 1N NaOH solution. The reaction mixture was stirred at room temperature for 48 h and the organics were removed in vacuo. The resulting mixture was acidified with 10% HCl and extracted with EtOAc. The combined organics were washed with water and brine, dried over $MgSO_4$, filtered and concentrated in vacuo. The resulting residue was triturated with hexanes and filtered to provide 0.87 g (84%) of the desired carboxylic acid as a white solid. CI Mass Spec: 398 (M+H).

EXAMPLE 17

2-[Benzyl-(4-metboxy-benzenesulfonyl)-amino]-3-chloro-benzoic acid

In the same manner as described in Example 16, 0.404 g (0.907 mmol) of the product of Example 9 provided 0.327 g (84%) of the desired carboxylic acid as a white solid. Electrospray Mass Spec 432 (M+H).

EXAMPLE 18

2-[Benzyl-(4-methoxy-benzenesulfonyl)-amino]-5-bromo-3-methyl-benzoic acid

To a solution of 0.444 g (0.88 lmmol) of the product of Example 11 in 20 mL of MeOH/THF (1:1) was added 9.3 mL 1N NaOH and the mixture heated at reflux for 18 h. The mixture was cooled to room temperature and the organic removed in vacuo. The remaining solution was acidified with 10% HCl and extracted with EtOAc. The extract was washed with water and brine, dried over $MgSO_4$, filtered and concentrated in vacuo. The residue provided 0.364 g (84%) of the desired carboxylic acid as a white solid after trturation with ether. CI Mass Spec: 490 (M+H).

EXAMPLE 19

2-[Benzyl-(4-methoxy-benzenesulfonyl)-amino]-4-methyl-benzoic acid

To a solution of the product of Example 12 in 30 mL of methanol was added 7.5 mL (0.038 mol) of 5N sodium hydroxide solution and the resulting mixture was heated to reflux for 66 h. The reaction was then cooled to room tempeature and the organics were removed in vacuo. The resulting mixture was acidified with 10% HCl and extracted with EtOAc. The combined organics were washed with water and brine, dried over $MgSO_4$, filtered and concentrated in vacuo. The resulting residue was triturated with ether and filtered to provide 0.984 g (79%) of the desired carboxylic acid as a white solid. Electospray Mass Spec: 427 (M+H).

EXAMPLE 20

2-[Benzyl-(4-methoxy-benzenesulfonyl)-amino]-6-methyl-benzoic acid

In the same manner as described in Example 19, 1.043 g (2.08 mmol) of the product of Example 13 provided 0.547 g (64%) of the desired carboxylic acid as a white solid after recrystallization from EtOAc/Hexanes. Electrospray Mass Spec: 412 (M+H).

EXAMPLE 21

2-[Benzyl-(4-methoxy-benzenesulfonyl)-amino]-3-methyl-benzoic acid

In the same manner as described in Example 19, 0.935 g (1.864 mmol) of the product of Example 14 provided 0.551 g (72%) of the desired carboxylic acid as a white solid after trituration with hexanes. Electrospray Mass Spec: 412 (M+H).

EXAMPLE 22

2-[Benzyl-(4-methoxy-benzenesulfonyl)-amino]-5-methyl-benzoic acid

In the same manner as described in Example 19, 1.931 g (3.85 mmol) of the product of Example 15 provided 1.19 g (70%) of the desired carboxylic acid as a white solid after trituration with $CH_2Cl_2$/hexanes (2:1). Electrospray Mass Spec: 412 (M+H).

EXAMPLE 23

2-[Benzyl-(4-methoxy-benzenesulfonyl)-amino]-N-hydroxy-benzamide

To a solution of 0.50 g (1.26 mmol) of the product of Example 16 in 12.5 mL of dichloromethane was added 0.095 mL of DMF followed by 0.22 mL of oxalyl chloride and the resulting reaction mixture was stirred at room temperature for 1 h.

In a separate flask, 1.05 mL (7.55 mmol) of triethylamine was added to a 0° C. mixture of 0.35 g (5.04 mmol) of hydroxylamine hydrochloride in 5.5 mL of THF and 1.4 mL of water. After this mixture had stirred for 15 min at 0° C., the acid chloride solution was added to it in one portion and the resulting solution was allowed to warm to room temperature with stirring overnight. The reaction mixture was then acidified to pH3 with 10% HCl and extracted with EtOAc. The combined organic layers were dried over $Na_2SO_4$, filtered and concentrated in vacuo. The crude residue was triturated with ether to provide 0.43 g (83%) of the desired hydroxamic acid as a white solid. CI Mass Spec: 413 (M+H).

EXAMPLE 24

2-[Benzyl-(4-methoxy-benzenesulfonyl)-amino]-3-chloro-N-hydroxy-benzamide

In the same manner as described in Example 23, 0.280 g (0.649 mmol) of the product of Example 12 gave 0.161 g (56%) of the desired hydroxamic acid as a white solid. Electrospray Mass Spec: 446 (M+H).

EXAMPLE 25

2-[Benzyl-(4-methoxy-benzenesulfonyl)-amino]-5-bromo-N-hydroxy-3-methyl-benzamide In the same manner as described in Example 23, 0.303 g (0.618 mmol) of the product of Example 18 gave 0.164 g (53%) of the desired hydroxamic acid as a white solid. Electrospray Mass Spec: 505 (M+H).

EXAMPLE 26

2-[Benzyl-(4-methoxy-benzenesulfonyl)-amino]-N-hydroxy-4-methyl-benzamide

In the same manner as described in Example 23, 1.20 g (2.91 mmol) of the product of Example 19 gave 0.984 g (79%) of the desired hydroxamic acid as a white solid after trituration with ether. Electrospray Mass Spec: 427 (M+H).

EXAMPLE 27

2-[Benzyl-(4-methoxy-benzenesulfonyl)-amino]-N-hydroxy-6-methyl-benzamide

In the same manner as described in Example 23, 0.537 g (1.30mmol) of the product of Example 20 gave 0.443 g (80%) of the desired hydroxamic acid as a white solid after trituration with $CH_2Cl_2$/Hexanes (1:4). Electrospray Mass Spec: 427 (M+H).

EXAMPLE 28

2-[Benzyl-(4-methoxy-benzenesulfonyl)-amino]-N-hydroxy-3-methyl-benzamide

In the same manner as described in Example 23, 0.398 g (0.967 mmol) of the product of Example 21 gave 0.348 g (84%) of the desired hydroxamic acid as a white solid after trituation with $CH_2Cl_2$/Hexanes (1:4). Electrospray Mass Spec: 427 (M+H).

EXAMPLE 29

2-[Benzyl-(4-methoxy-benzenesulfonyl)-amino]-N-hydroxy-5-methyl-benzamide

In the same manner as described in Example 23, 1.00 g (2.43 mmol) of the product of Example 22 gave 0.761 g (73%) of the desired hydroxamic acid as a white solid after trituration with CH$_2$Cl$_2$/Hexanes (1:4). Electrospray Mass Spec: 427 (M+H).

EXAMPLE 30

2-Amino-3-hydroxy-benzoic acid methyl ester

To a solution of 1.0 g (6.53 mmol) of 3-hydroxyanthranilic acid in 15 mL of methanol was added 5.0 mL of BF$_3$-methanol complex and the resulting solution was heated to reflux for 24 h. After cooling to room temperatue the reaction mixture was poured into saturated sodium carbonate solution and then extracted with ether. The combined organics were washed with water and brine, dried over sodium sulfate, filtered and concentrated in vacuo to provide 0.90 g (83%) of the desired product as a brown solid. Electrospray Mass Spec: 167.8 (M+H)+

EXAMPLE 31

3-Hydroxy-2-(4-methoxy-benzenesulfonylamino)-benzoic acid methyl ester

To a solution of 0.748 g (4.48 mmol) of the product of Example 30 in 10.0 mL of pyridine was added 0.928 g (4.48 mmol) of p-methoxybenzenesulfonyl chloride. The reaction mixture was stirred for 24 h at room temperature and then diluted with chloroform and washed with 5% HCl solution and water. The organic layer was then dried over MgSO$_4$, filtered and concentrated in vacuo. The residue was triturated with ether-hexanes and the resulting solid was filtered and dried to provide 0.86 g (57%) of the desired product as a tan solid. Electrospray Mass Spec: 338.2 (M+H)+

EXAMPLE 32

2-[Benzyl-(4-methoxy-benzenesulfonyl)-amino]-3-benzyloxy-benzoic acid methyl ester In the same manner as described in Example 9, 0.50 g (1.17 mmol) of the product of Example 31 provided 0.60 g (100%) of the desired product as a colorless oil. Electrospray Mass Spec: 518.2 (M+H)+

EXAMPLE 33

2-[Benzyl-(4-methoxy-benzenesulfonyl)-amino]-3-benzyloxy-benzoic acid

In the same manner as descrbed in Example 18, 0.25 g (0.484 mmol) of the product of Example 32 provided 0.22 g (91%) of the desired product as a white solid. Electrospray Mass Spec: 504.2 (M+H)+

EXAMPLE 34

2-[Benzyl-(4-methoxy-benzenesulfonyl)-amino]-3-benzyloxy-N-hydroxy-benzamide

In the same manner as described in Example 23, 0.19 g (0.382 mmol) of the product of Example 33 provided 0.16 (81%) of the desired product as a white solid. Electrospray Mass Spec: 519.2 (M+H)+

EXAMPLE 35

3-(tert-Butyl-dimethyl-silanyloxy)-2-(4-methoxy-benzenesulfonylamino)-benzoic acid methyl ester To a solution of 0.139 g (0.412 mmol) of the product of Example 31 in 2.0 mL of DMF was added 0.70 g (1.03 mmol) of imidazole and 0.075 g (0.495 mmol) of t-butyldimethylsilyl chloride. The reaction mixture was then srtied at room temperature for 3h and then diluted with 75 mL of ether. The resulting mixture was washed with water and brine, dried over MgSO$_4$, filtered and concentrated in vacuo to provide 0.179 g (96%) of the desired product as a white solid. Electrospray Mass Spec: 452.2 (M+H)+

EXAMPLE 36

2-[Benzyl-(4-methoxy-benzenesulfonyl)-amino]-3-(tert-butyl-dimethyl-silanyloxy)-benzoic acid methyl ester In the same manner as described in Example 9, 0.114 g (0.253 mmol) of the product of Example 35 provided 0.088 (64%) of the desired product as a colorless oil. Electrospray Mass Spec: 542.3 (M+H)+

EXAMPLE 37

2-[Benzyl-(4-methoxy-benzenesulfonyl)-amino]-3-hydroxy-benzoic acid methyl ester To a solution of 4.42 g (8.17 mmol) of the product of Example 36 in 50 mL of THF was added 16.3 mL (16.3 mmol) of a 1M solution of Bu$_4$NF/THF. The reaction mixture was stirred at room tempeture for 0.5 h and then diluted with ether and washed with 5% HCl solution, water and brine. The resulting solution was dried over MgSO$_4$, filtered and concentrated in vacuo. The residue was triturated with ether to provide 2.81 g (81%) of the desired product as a white solid. Electrospray Mass Spec: 428.3 (M+H)+

EXAMPLE 38

2-[Benzyl-(4-methoxy-benzenesulfonyl)-amino]-3-tert-butoxycarbonylmethoxy-benzoic acid methyl ester To a solution of 0.40 g (0.94 mmol) of the product of Example 37 in 10 mL of DMF was added 0.047 g (1.171 mmol) of a 60% suspension of sodium hydride in minena oil. The resulting mixture was stirred at room temperature for 0.5 h and then 0.277 mL (1.873 mmol) of t-butylbromoacetate was added in one portion. Th reaction mixture was stirred for an additional 18 h and then diluted with ether, washed with water and brine, dried over MgSO$_4$, filtered and concentrated in vacuo. The residue was triturated with ether-hexanes to provide 0.423 g (83%) of the desired product as a white solid. Electrospray Mass Spec: 524.3 (M+H)+

EXAMPLE 39

2-[Benzyl-(4-methoxy-benzenesulfonyl)-amino]-3-(2,2,2-trifluoro-ethoxy)-benzoic acid methyl ester In the same manner as described in Example 38, 0.40 g (0.937 mmol) of the product of Example 37 and 0.185 mL (1.873 mmol) of 2-iodo-1,1,1-trifluoroethane provided 0.231 g (48%) of the desired product as a colorless oil. Electrospray Mass Spec: 510.3 (M+H)+

EXAMPLE 40

2-[Benzyl-(4-methoxy-benzenesulfonyl)-amino]-3-(2-methoxy-ethoxymethoxy)-benzoic acid methyl ester In the same manner as described in Example 38, 0.40 g (0.937 mmol) of the product of Example 37 and 0.134 mL (1.171 mmol) of MEM-Cl provided 0.454 g (94%) of the desired product as a colorless oil. Electrospray Mass Spec: 516.2 (M+H)+

EXAMPLE 41

2-[Benzyl-(4-methoxy-benzenesulfonyl)-amino]-3-(4-methoxycarbonyl-benzyloxy)-benzoic acid methyl ester In the same manner as described in Example 38, 0.275 g (0.644 mmol) of the product of Example 37 and 0.295 g (1.288 mmol) of methyl 4-(bromomethyl)benzoate provided 0.322 g (87%) of the desired product as a white solid. Electrospray Mass Spec: 576.2 (M+H)+

EXAMPLE 42

2-[Benzyl-(4-methoxy-benzenesulfonyl)-amino]-3-(3-ethoxycarbonyl-propoxy)-benzoic acid methyl ester In the same manner as described in Example 38, 0.50 g (1.171 mmol) of the product of Example 37 and 0419 mL (2.927 mmol) of ethyl 4-bromobutyrate provided 0.530 g (84%) of the desired product as a colorless oil. Electrospray Mass Spec: 542.3 (M+H)+

EXAMPLE 43

2-[Benzyl-(4-methoxy-benzenesulfonyl)-amino]-3-(4-methoxycarbonyl-butoxy)-benzoic acid methyl ester In the same manner as described in Example 38, 050 g (1.171 mmol) of the product of Example 37 and 0.419 mL (2.927 mmol) of methyl 5-bromovalerate provided 0.477 g (75%) of the desired product as a white solid. Electrospray Mass Spec: 542.3 (M+H)+

EXAMPLE 44

2-[Benzyl-(4-methoxy-benzenesulfonyl)-amino]-3-isopropoxy-benzoic acid methyl ester To a solution of 0.20 g (0.468 mmol) of the product of Example 37 dissolved in 5.0 mL of DMF was added 0.26 mL (2.81 mmol) of 2-bromopropane and 1.16 g (8.43 mmol) of potassium carbonate. The reaction mixture was then heated to 80 degrees for 18 h, cooled to room temperature, diluted with ether and washed with water and brine, dried over MgSO$_4$, filtered and concentrated in vacuo. The residue was chromatographed on silica gel eluting with EtOAc-Hexanes (1:3) to provide 0.198 g (90%) of the desired product as a colorless oil. Electrospray Mass Spec: 470.3 (M+H)+

EXAMPLE 45

2-[(4-Methoxy-benzenesulfonyl)-pyridin-3-ylmethyl-amino]-3-(pyridin-3-ylmethoxy)-benzoic acid methyl ester To a solution of 0.40 g (1.187 mmol) of the product of Example 31 dissolved in 5.0 mL of DMF was added 0.409 g (2.492 mmol) of 3-picolyl chloride hydrochloride and 1.03 g (7.477 mmol) of potassium carbonate. The reaction mixture was then stirred at room temperature for 18 h, diluted with water and extracted with ether. The organics were then extracted with 6N HCl solution and the aqueous acid layer was then basified with 6N NaOH solution and then extrrcted with ether. The resulting ether layer was dried over sodium sulfate, filtered and concentrated in vacuo to provide 0.34 g (55%) of the desired product as a brown oil. Electrospray Mass Spec: 520.2 (M+H)+

EXAMPLE 46

2-[Benzyl-(4-methoxy-benzenesulfonyl)-amino]-3-carboxymethoxy-benzoic acid

In the same manner as described in Example 18, 0.314 g (0.580 mmol) of the product of Example 38 provided 0.262 g (96%) of the desired product as a white solid. Electrospray Mass Spec: 472.1 (M+H)+

EXAMPLE 47

2-[Benzyl-(4-methoxy-benzenesulfonyl)-amino]-3-(2,2,2-trifluoroethoxy)-benzoic acid In the same manner as described in Example 18, 0.20 (0.393 mmol) of the product of Example 39 provided 0.168 g (87%) of the desired product as a white solid. Electrospray Mass Spec: 496.1 (M+H)+

EXAMPLE 48

2-[Benzyl-(4-methoxy-benzenesulfonyl)-amino]-3-(2-methoxy-ethoxymethoxy)-benzoic acid In the same manner as described in Example 18, 0.363 g (0.705 mmol) of the product of Example 40 provided 0.336 (95%) of the desired product as a white foam. Electrospray Mass Spec: 502.2 (M+H)+

EXAMPLE 49 benzyloxy)-benzoic acid

In the same manner as described in Example 18, 0.283 g (0.492 mmol) of the product of Example 41 provided 0.245 g (91%) of the desired product as a white solid. Electrospray Mass Spec: 548.1 (M+H)+

EXAMPLE 50

2-[Benzyl-(4-methoxy-benzenesulfonyl)-amino]-3-(3-carboxy-propoxy)-benzoic acid

In the same manner as described in Example 18, 0.363 g (0.671 mmol) of the product of Example 42 provided 0.260 g (78%) of the desired product as a white solid. Electrospray Mass Spec: 498.1 (M–H)–

EXAMPLE 51

2-[Benzyl-(4-methoxy-benzenesulfonyl)-amino]-3-(4-carboxy-butoxy)-benzoic acid

In the same manner as described in Example 18, 0.323 g (0.597 mmol) of the product of Example 43 provided 0.243 (79%) of the desired product as a white solid. Electrospray Mass Spec: 512.1 (M–H)–

EXAMPLE 52

2-[Benzyl-(4-methoxy-benzenesulfonyl)-amino]-3-isopropoxy-benzoic acid

In the same manner as described in Example 18, 0.348 g (0.742 mmol) of the product of Example 44 provided 0.284 g (84%) of the desired product as a white solid. Electrospray Mass Spec: 456.3 (M+H)+

EXAMPLE 53

2-[(4-Methoxy-benzenesulfonyl)-pyridin-3-ylmethyl-amino]-3-(pyridin-3-ylmethoxy)-benzoic acid To a solution of 0.311 g (0.599 mmol) of the product of Example 45 in 6.0 mL of THF-MeOH (1:1) was added 0.050 g (1.197 mmol) of lithium hydroxide monohydrate. The reaction mix was heated to reflux for 24 h and then concentrated in vacuo. The residue was washed with THF and filtered. The filtrate was concentrated in vacuo to provide 0.277 g (91%) of the lithium salt of the title compound as a brown foam. Electrospray Mass Spec: 506.2 (M+H)+

EXAMPLE 54

2-[Benzyl-(4-methoxy-benzenesulfonyl)-amino]-N-hydroxy-3hydroxycarbamoylmethoxy-benzamide In the same manner as described in Example 23, 0.110 g (0.234 mmol) of the product of Example 46 provided 0.085 g (75%) of the desired product as a white solid. Electrospray Mass Spec: 502.2 (M+H)+

EXAMPLE 55

2-[Benzyl-(4-methoxy-benzenesulfonyl)-amino]-N-hydroxy-3-(2,2,2-trifluoroethoxy)-benzamide In the same manner as described in Example 23, 0.131 (0.265 mmol) of the product of Example 47 provided 0.092 g (68%) of the desired product as a white solid. Electrospray Mass Spec: 511.1 (M+H)+

EXAMPLE 56

2-[Benzyl-(4-methoxy-benzenesulfonyl)-amino]-N-hydroxy-3-(2-methoxy-ethoxymethoxy)-benzamide In the same manner as described in Example 23, 0.296 (0.591 mmol) of the product of Example 48 provided 0.228 g (75%) of the desired product as a brown glass. Electrospray Mass Spec: 517.2 (M+H)+

EXAMPLE 57

2-[Benzyl-(4-methoxy-benzenesulfonyl)-amino]-3-[4-(hydroxyaminocarbonyl)-benzyloxy]-N-hydroxy-benzamide In the same manner as described in Exanple 23, 0.207 g (0.378 mmol) of the product of Example 49 provided 0.20 g (92%) of the desired product as a white solid. Electrospray Mass Spec: 576.0 (M−H)−

EXAMPLE 58

2-[Benzyl-(4-methoxy-benzenesulfonyl)-amino]-N-hydroxy-3-(3-hydroxycarbamoyl-propoxy)-benzamide In the same manner as described in Example 23, 0.224 g (0.449 mmol) of the product of Example 50 provided 0. 195 g (82%) of the desired product as a white solid. Electrospray Mass Spec: 530.1 (M+H)+

EXAMPLE 59

2-[Benzyl-(4-methoxy-benzenesulfonyl)-amino]-N-hydroxy-3-(4-hydroxycarbamoyl-butoxy)-benzamide In the same manner as described in Example 23, 0.20 g (0.390 mmol) of the product of Example 51 provided 0.208 g (98%) of the desired product as a tan solid. Electrospray Mass Spec: 544.1 (M+H)+

EXAMPLE 60

2-[Benzyl-(4-methoxy-benzenesulfonyl)-amino]-N-hydroxy-3-isopropoxy-benzamide

In the same manner as described in Example 23, 0.245 g (0.540 mmol) of the product of Example 52 provided 0.222 g (88%) of the desired product as a white solid. Electrospray Mass Spec: 471.2 (M+H)+

EXAMPLE 61

N-Hydroxy-2-[(4-methoxy-benzenesulfonyl)-pyridin-3-ylmethyl-amino]-3-methyl-benzamide To a solution of 0.65 mL (1.29 mmol) of a 2M solution of oxalyl chloride in $CH_2Cl_2$ at 0° C. was added 0.10 mL (1.29 mmol) of DMF and the mixture was stirred at 0° C. for 15min, then let warm to room temperature and stired for an additional 1 h. A solution of 0.220 g (0.43 mmol) of the product of Example 53, in 1 mL of DMF, was then added to the reaction mixture and the reaction was stirred for 1 h at room temperature.

In a separate flask, 1.35 mL (9.675 mmol) of triethylamine was added to a 0° C. mixture of 0.448 g (6.45 mmol) of hydroxylamine hydrochloride in 6.8 mL of THF and 1.8 mL of water. After this mixture had stirred for 15 min at 0° C., the acid chloride solution was added to it in one portion and the resulting solution was allowed to warm to room tempature with stirring overnight. The reaction mixture next was diluted with $CH_2Cl_2$ and washed with water and saturated sodium bicarbonate solution. The organic layer was dried over $Na_2SO_4$, filtered and concentrated in vacuo. The crude residue was tritrated with ether to provide 0.124 g (55%) of the desired hydroxamic acid as a white solid. Electrospray Mass Spec: 521.2 (M+H)+.

EXAMPLE 62

2-(4-Methoxy-benzenesulfonylamino)-3,5-dimethyl-benzoic acid methyl ester

In the same manner as described in Example 31, 7.00 g (0.039 mol) of methyl 3,5-dimethylanthranilate provided 11.5 g (84%) of the desired product as a white solid. Electrospray Mass Spec: 350.3 (M+H)+.

EXAMPLE 63

2-(4-Fluoro-benzenesulfonylamino)-3,5-dimethyl-benzoic acid methyl ester

In the same manner as described in Example 31, 2.00 g (0.011 mol) of methyl 2,5-dimethylanthranilic acid and 2.17 g (0.011 mol) of 4-fluorobenzenesulfonyl chloride provided 3.09 g (82%) of the desired product as a white solid. Electrospray Mass Spec: 338.3 (M+H)+.

EXAMPLE 64

2-[Benzyl-(4-methoxy-benzenesulfonyl)-amino]-3,5-dimethyl-benzoic acid methyl ester In the same manner as described in Example 9, 1.00 g (0.2.865 mmol) of the product of Example 62 provided 1.065 g (85%) of the desired product as a white solid. Electrospray Mass Spec: 440.3 (M+H)+.

EXAMPLE 65

2-[Benzyl-(4-fluoro-benzenesulfonyl)-amino]-3,5-dimethyl-benzoic acid methyl ester In the same manner as described in Example 9, 1.00 g (0.2.865 mmol) of the product of Example 63 provided 1.084 g (85%) of the desired product as a white solid. Electrospray Mass Spec: 428.3 (M+H)+.

EXAMPLE 66

2-[Benzyl-(4-methoxy-benzenesulfonyl)-amino]-3,5-dimethyl-benzoic acid

In the same manner as described in Example 18, 0.94 g (2.141 mmol) of the product of Example 64 provided 0.827 g (91%) of the desired product as a white solid. Electrospray Mass Spec: 426.3 (M+H)+.

EXAMPLE 67

2-[Benzyl-(4-fluoro-benzenesulfonyl)-amino]-3,5-dimethyl-benzoic acid

In the same manner as described in Example 9, 0.963 g (2.255 mmol) of the product of Example 65 provided 0.486 g (52%) of the desired product as a white solid. Electrospray Mass Spec: 414.3 (M+H)+.

EXAMPLE 68

2-[Benzyl-(4-methoxy-benzenesulfonyl)-amino]-N-hydroxy-3,5-dimethyl-benzamide

In the same manner as described in Example 23, 0.683 g (1.607 mmol) of the product of Example 66 provided 0.436 g (62%) of the desired product as a white solid. Electrospray Mass Spec: 441.3 (M+H)+.

EXAMPLE 69

2-[Benzyl-(4-fluoro-benzenesulfonyl)-amino]-N-hydroxy-3,5-dimethyl-benzamide

In the same manner as described in Example 23, 0.423 g (1.024 mmol) of the product of Example 67 provided 0.364 g (83%) of the desired product as a white solid. Electrospray Mass Spec: 429.3 (M+H)+.

EXAMPLE 70

2-[Benzyl-(4-butoxy-benzenesulfonyl)-amino]-3,5-dimethyl-benzoic acid butyl ester To a solution of the product of Example 65 in 10 mL of DMF was added 0.429 mL (4.684 mmol) of n-butanol and 0.187 g (4.684 mmol) of 60% sodium hydride. The reaction mixture was stired for 18 h at room temperature and the quenched with 5% HCl solution. The resulting mixture was extracted with ether and the combined organics were washed with water, dried over MgSO$_4$, filtered and concentrated in vacuo. The residue was chromatographed on silica eluting with EtOAc-Hexanes (1:10) to provide 0. 134 g (24%) of the desired product as a red oil. Electrospray Mass Spec: 524.4 (M+H)+.

EXAMPLE 71

2-[Benzyl-(4-butoxy-benzenesulfonyl)-amino]-3,5-dimethyl-benzoic acid

In the same manner as described in Example 18, 0.134 g (0.256 mmol) of the product of Example 70 provided 0.115 g (97%) of the desired product as a white solid. Electrospray Mass Spec: 468.3 (M+H)+.

EXAMPLE 72

2- [Benzyl-(4-butoxy-benzenesulfonyl)-amino]-N-hydroxy-3,5-dimethyl-benzamide

In the same manner as described in Example 23, 0.139 g (0.298 mmol) of the product of Example 71 provided 0.105 g (73%) of the desired product as a yellow foam. Electrospray Mass Spec: 483.3 (M+H)+.

EXAMPLE 73

2-[Benzyl-(4-benzyloxy-benzenesulfonyl)-amino]-3,5-dimethyl-benzoic acid

To a solution of 0.50 g (1.171 mmol) of the product of Example 65 in 10 mL of DMF was added 0.485 mL (4.684 mmol) of benzyl alcohol and 0.187 g (4.684 mmol) of 60% sodium hydride. The eaction mixture was stirred for 18 h at room temperature and the quenched with 5% HCl solution. The resulting mixture was extracted with ether and the combined organics were washed with water, dried over MgSO$_4$, filtered and concentrated in vacuo. The residue was dissolved 10 mL of MeOH-THF (1:1) and 4.7 mL of 1N sodium hydroxide solution was added. The resulting mixture was heated to reflux for 18 h and then cooled to room temperature, acidified with 5% HCl and extracted with EtOAc. The combined organics were washed with water and brine, dried over MgSO$_4$, filtered and concentrated in vacuo. Triturion of the residue with edter provided 0.432 g (74%) of the desired product as a white solid. Electrospray Mass Spec: 502.3 (M+H)+.

EXAMPLE 74

2-[Benzyl-(4-benzyloxy-benzenesulfonyl)-amino]-N-hydroxy-3,5-dimethyl-benzamide

In the same manner as described in Example 23, 0.366 (0.731 mmol) of the product of Example 73 provided 0.347 g (92%) of the desired product as a white solid. Electrospray Mass Spec: 517.2 (M+H)+.

EXAMPLE 75

2-[Benzyl-(4-methoxy-benzenesulfonyl)-amino]-5-hex-1-ynyl-3-methyl-benzoic acid methyl ester To a solution of 0.324 g (0.643 mmol) of the product of Example 11 in 2.0 mL of DMF and 2.0 mL of triethylamine was added 0.088 mL (0.771 mmol) of 1-hexyne, 9 mg (0.013 mmol) of bis(triphenylphosphine)palladium(II)dichloride and 1.2 mg of copper(I)iodide. The reaction mixture was then heated to 65 degrees for 5 h and an additional 0.22 mL of 1-hexyne was added to the reaction. The motion was then heated to zeflux for 6 h and then cooled to room tempemaure and diluted with ether. The organics were washed with water and brine, dried over MgSO$_4$, filtered and concentrated in vacuo. The residue was chromatographed on silica eluting with EtOAc-Hex (1:10) to provide 0.198 g (61%) of the desired product as a yellow oil. Electrospray Mass Spec: 506.3 (M+H)+.

EXAMPLE 76

2-[Benzyl-(4-methoxy-benzenesulfonyl)-amino]-5-hex-1-ynyl-3-methyl-benzoic acid

In the same manner as described in Example 18, 0.165 g (0.327 mmol) of the product of Example 75 provided 0.123 g (77%) of the desired product as a tan solid. Electrospray Mass Spec: 492.2 (M+H)+.

EXAMPLE 77

2-[Benzyl-(4-methoxy-benzenesulfonyl)-amino]-5-hex-1-ynyl-N-hydroxy-3-methyl-benzamide In the same manner as described in Example 23, 0.115 g (0.234 mmol) of the product of Example 76 provided 0.097 g (82%) of the desired product as a tan foam. Electrospray Mass Spec: 507.3 (M+H)+.

EXAMPLE 78

2-[Benzyl-(4-methoxy-benzenesulfonyl)-amino]-5-ethynyl-3-methyl-benzoic acid methyl ester To a solution of 0.277 g (0.50 mmol) of the product of Example 11 in 2.0 mL of DMF and 2.0 mL of triethylamine was added 0.39 mL (0.2.748 mmol) of trimetylsilyl acetylene, 19 mg (0.027 mmol) of bis(triphenylphosphine) palladium(II)dichloride and 2.6 mg of copper(I)iodide. The reaction mixture was then heated to 65 degrees for 2 h and then cooled to room temperature and diluted with ether. The organics were washed with 5% Hcl solution, water and brine, dried over MgSO$_4$, filtered and concentrated in vacuo. The residue was dissolved in 5 mL of THF, 1 mL of 1M tetrbutylammonium fluoride-THF solution was added and the reaction was stirred at room temperatue for 1 h, then diluted with ether, washed with 5% HCl solution, water and brine, dried over MgSO$_4$, filtered and concentrated in vacuo. The residue was chromatographed on silica eluting with EtOAc-Hex (1:10) to provide 0.197 g (80%) of the desired product as a white foam. Electrospray Mass Spec: 450.3 (M+H)+.

EXAMPLE 79

2-[Benzyl-(4-methoxy-benzenesulfonyl)-amino]-5-ethynyl-3-methyl-benzoic acid In the same manner as described in Example 18, 0.177 g (0.394 mmol) of the product of Example 78 provided 0.161 g (94%) of the desired product as a tan solid. Electrospray Mass Spec: 436.2 (M+H)+.

EXAMPLE 80

2-[Benzyl-(4-methoxy-benzenesulfonyl)-amino]-5-ethynyl-N-hydroxy-3-methyl-benzamide In the same manner as described in Example 23, 0.136 g (0.313 mmol) of the product of Example 79 provided 0.116 g (82%) of the desired product as a tan foam. Electrospray Mass Spec: 451.3 (M+H)+.

EXAMPLE 81

2-[(4-Methoxy-benzenesulfonyl)-pyridin-3-ylmethyl-amino]-3-methyl-benzoic acid methyl ester To a solution of 1.00 g (2.985 mmol) of the product of Example 3 in 7.5 mL of DMF was added 0.514 g (3.134 mmol) of 3-picolyl chloride hydrochloride and 1.30 g (9.50 mmol) of potassium carbonate. The rection was stirred for 18 h at room temre and then an additional 0.051 g of 3-picolyl chloride hydrochloride and 0.130 g of potassium carbonate was added and the reaction was steeed for 18 h at room temperature. The reaction was then diluted with water and extracted with ether. The combined organic layers were extrated with 6N HCl solution and the aqueous acid layer was then basified with 6N NaOH solution and then extracted with ether. The resulting ether layer was dried over sodium sulfate, filtered and concentrated in vacuo. Trituration of the residue with ether provided 1.058 g (83%) of the desired product as a white solid. Electrospray Mass Spec: 427.3 (M+H)+.

EXAMPLE 82

2-[(4-Methoxy-benzenesulfonyl)-pyridin-3-ylmethyl-amino]-3-methyl-benzoic acid To a solution of 0.924 g (2.169 mmol) of the product of Example 81 in 10 mL of THF-water (1:1) was added 0.091 g of lithium hydroxide monohydrate. The reaction mixture was heated to reflux for 48 h then cooled to room temeratue and washed with ether. The aqueous layer was then concentrated in vacuo to provide 0.894 g (100%) of the lithium salt of the tide compound as a white solid. Electrospray Mass Spec: 413.2 (M+H)+

EXAMPLE 83

N-Hydroxy-2-[(4-methoxy-benzenesulfonyl)-pyridin-3-ylmethyl-amino]-3-methyl-benzamide To a solution of 1.98 mL (3.966 mmol) of a 2M solution of oxalyl chloride in CH$_2$Cl$_2$ at 0° C. was added 0.307 mL (3.966 mmol) of DMF and the mixture was stirred at 0° C. for 15 min, then let warm to room temperature and stined for an additional 1 h. A solution of 0.829 g (1.983 mmol) of the product of Example 82, in 1 mL of DMF, was then added to the reaction mixture and the reaction was stifed for 1 h at room temperature.

In a separate flask, 4.14 mL (0.030 mol) of tdethylamine was added to a 0° C. mixture of 1.378 g (0.020 mol) of hydroxylamine hydrochloride in 19.5 mL of THF and 5.6 mL of water. After this mixture had stirred for 15 min at 0° C., the acid chloride solution was added to it in one portion and the resulting solution was allowed to warm to room temperatue with stirng overnight Ie reaction mixture next was diluted with CH$_2$Cl$_2$ and washed with water and saturated sodium bicarbonate solution. The organic layer was dried over Na$_2$SO$_4$, filtered and concentrated in vacuo. The crude residue was titurated with EtOAc-ether to provide 0.414 g (51%) of the tide compound as a white solid.

To a room tempeture solution of 0.403 g (0.976 mmol) of the hydroxamic acid in 10 ml of CH$_2$Cl$_2$—MeOH (30:1) was added 0.27 mL of a 4M HCl-ether solution. The reaction mixture was stiimd for 0.5 h and the resulting precipitate was collected by filtration and died in vacuo to provide 0.439 g (100%) of the hydrochloride salt of the title compound as a white solid. Electrospray Mass Spec: 428.2 (M+H)+.

EXAMPLE 84

2-[(4-Methoxy-benzenesulfonyl)-pyridin-3-ylmethyl-amino]-benzoic acid

To a solution of 0.958 g (2.985 mmol) of the product of Example 1 in 7.5 mL of DMF was added 0.514 g (3.134 mmol) of 3-picolyl chloride hydrochloride and 1.30 g (9.50 mmol) of potassium carbonate. The reaction was steeed for 18 h at room temprature and then an additional 0.051 g of 3-picolyl chloride hydrochloride and 0.130 g of potassium carbonate was added and the reaction was stied for 18 h at room temperature. The reaction was then diluted with water and extracted with ether. The combined organic layers were extracted with 6N HCl solution and the aqueous acid layer was then basified with 6N NaOH solution and then extracted with ether. The resulting ether layer was dried over sodium sulfate, filtered and concentrated in vacuo. Trituration of the residue with ether provided 0.843 g (69%) of the sodium salt of the title compound as a pink solid.

To a solution of 0.830 g (2.015 mmol) of the above product in 10 mL of THF-water (1:1) was added 0.093 g of lithium hydroxide monohydrate. The reaction mixture was heated to reflux for 48 h then cooled to room temperature. The reaction mixture was then concentrated in vacuo to provide 0.813 g (100%) of the lithium salt of the tide compound as a white solid. Electrospray Mass Spec: 399.2 (M+H)+

EXAMPLE 85

N-Hydroxy-2-[(4-methoxy-benzenesulfonyl)-pyridin-3-ylmethyl-amino]-benzamide

In the same manner as described in Example 83, 0.618 g (1.530 mmol) of the product of Example 84 provided 0.450 g (62%) of the hydrochloride salt of the title compound as a tan solid Electrospray Mass Spec: 414.2 (M+H)+

EXAMPLE 85

2-[(4-Methoxy-benzenesulfonyl)-pyridin-3-ylmethyl-amino]-3,5-dimethyl-benzoic acid methyl ester In the same manner as described in Example 81, 1.00 g (2.865 mmol) of the product of Exalmpe 62 provided 0.932 g (74%) of the desired product as a tan solid. Electrospray Mass Spec: 441.3 (M+H)+

EXAMPLE 87

2-[(4-Methoxy-benzenesulfonyl)-pyridin-3-ylmethyl-amino]-3,5-dimethyl-benzoic acid In the same manner as descried in Example 82, 0.810 g (1.841 mmol) of the product of Example 86 provided 0.753 g (96%) of the desired product as a tan foam. Electrospray Mass Spec: 427.3 (M+H)+

EXAMPLE 88

N-Hydroxy-2-[(4-methoxy-benzenesulfonyl)-pyridin-3-ylmethyl-amino]-3,5-dimethyl-benzamide In the same manner as described in Example 83, 0.645 g (1.514 mmol) of the product of Example 87 provided 0.377 g (62%) of the hydrochloride salt of the title compound as a white solid. Electrospray Mass Spec: 442.3 (M+H)+

EXAMPLE 89

5-Bromo-2-[(4-methoxy-benzenesulfonyl)-pyridin-3-ylmethyl-amino]-3-methyl-benzoic acid methyl ester In the same manner as described in Example 81, 1.00 g (2.415 mmol) of the product of Example 10 provided 0.961 g (79%) of the desired product as a tan solid. Electrospray Mass Spec: 505.2 (M+H)+

EXAMPLE 90

5-Bromo-2-[(4-metboxy-benzenesulfonyl)-pyridin-3-ylmethyl-amino]-3-methyl-benzoic acid In the same manner as described in Example 82, 0.861 g (1.708 mmol) of the product of Example 89 provided 0.837 (100%) of the lithium salt of the tide compound as a tan solid. Electrospray Mass Spec: 491.1 (M+H)+

EXAMPLE 91

5-Bromo-N-hydroxy-2-[(4-methoxy-benzenesulfonyl)-pyridin-3-ylmethyl-amino]-3-methyl-benzamide In the same manner as described in Example 83, 0.767 g (1.546 mmol) of the product of Example 90 provided 0.407 g (56%) of the hydrochloride salt of the tile compound as a white solid. Electrospray Mass Spec: 506.2 (M+H)+

EXAMPLE 92

3-(4-Methoxy-benzenesulfonylamino)-naphthalene-2-carboxylic acid

In the same maaer as described in Example 4, 2.5 g (13.4 mmol) of 3-amino-2-naphthoic acid gave 2.49 g (52%) of the desired sulfonamide as a tan solid after trituration with EtOAc/hexane. Electrospray Mass Spec: 358 (M+H)+

EXAMPLE 93

3-[Benzyl-(4-methoxy-benzenesulfonyl)-amino]-naphthalene-2-carboxylic acid

In the same manner as described in Example 12, 1.2 g (3.36 mmol) of the product of Example 92 gave a brown oil which was dissolved in dioxane (20 mL) and treated with aqueous 2N sodium hydroxide. The resulting solution was heated at 80° C. for 3 days. Addition of 1N aqueous hydrochloric acid, extraction with EtOAc, drying with $MgSO_4$ and concentration in vacuo, followed by silica gel chromatography (hexane/EtOAc/HOAc) gave the desired carboxylic acid as a white solid (0.81 g, 54%). Electrospray Mass Spec: 448 (M+H)+

EXAMPLE 94

3-[Benzyl-(4-methoxy-benzenesulfonyl)-amino]-naphthalene-2-carboxylic acid hydroxyamide In the same manner as described in Example 23, 200 mg (0.45 mmol) of the product of Example 94 gave 0.155 g (75%) of the desired hydroxamic acid as a white powder. Electrospray Mass Spec: 463 (M+H)+

EXAMPLE 95

3-Methoxy-2-(4-methoxy-benzenesulfonylamino)-benzoic acid

In the same mer as described in Example 4, 2.14 g (12.8 mmol) of 2-amino-3-methoxybenzoic acid gave 2.08 g (48%) of the desired sulfonamide as a beige solid after trituration with $CH_2Cl_2$:hexane (1:2). CI Mass Spec 338.0 (M+H).

EXAMPLE 96

4-Chloro-2-(4-methoxy-benzenesulfonylamino)-3-methyl-benzoic acid methyl ester

In the same manner as described in Example 1, 0.5 g (2.5 nmol) of methyl 3-methyl-4-chloro anthranilate provided 0.56 g (61%) of the desired sulfonamide as a white solid after trituration with ether. Electrospray Mass Spec 370.2 (M+H).

EXAMPLE 97

2-[Benzyl-(4-methoxy-benzenesulfonyl)-amino]-3-methoxy-benzoic acid benzyl ester In the same manner as described in Example 12, 1.73 g (5.14 mmol) of the product of Example 95 gave 2.01 g (75%) of the desired product as a white solid after silica gel chromatography eluting with $CH_2Cl_2$. CI Mass Spec 518.1 (M+H).

EXAMPLE 98

2-[Benzyl-(4-methoxy-benzenesulfonyl)-amino]-4-chloro-3-methyl-benzoic acid methyl ester In the same manner as described in Example 9, 0.5 g (1.35 mmol) of the product of Example 96 provided 0.566 g (80%) of the desired product as a white solid after trituration with hexane. Electrospray Mass Spec 460.2(M+H).

EXAMPLE 99

2-[Benzyl-(4-methoxy-benzenesulfonyl)-amino]-3-methoxy-benzoic acid

In the same manner as described in Example 19, 1.86 g (3.6 mmol) of the product of Example 97 provided 1.39 g (90%) of the desired carboxylic acid as a white solid after trituration with $CH_2Cl_2$:hexane (1:4). CI Mass Spec 428.1 (M+H).

EXAMPLE 100

2-[Benzyl-(4-methoxy-benzenesulfonyl)-amino]-4-chloro-3-methyl-benzoic acid

In the same manner as described in Example 19, except a mixture of MeOH and ThF was used instead of MeOH, 0.506 g (1.1 mmol) of the product of Example 98 provided 0.454 g (93%) of the desired carboxylic acid as a white solid after triion with ether. Electrospray Mass Spec 446.1(M+H).

EXAMPLE 101

2-[Benzyl-(4-methoxy-benzenesulfonyl)-amino]-N-hydroxy-3-methoxy-benzamide

In the same manner as described in Example 23, 1.25 g (2.91 mmol) of the product of Example 99 gave 1.11 g (86%) of the desired hydroxamic acid as a white solid. CI Mass Spec 443.1 (M+H).

EXAMPLE 102

2-[Benzyl-(4-methoxy-benzenesulfonyl)-amino]-4-chloro-N-hydroxy-3-methyl-benzamide In the same manner as described in Example 23, 0.4 g (0.9 mmol) of the product of Example 100 provided 0.273 g (66%) of the desired hydroxamic acid as a white solid after silica gel chromatography eluting with EtOAc:hexane:acetic acid (1.0:1.5:0.5). Electrospray Mass Spec 461.2(M+H).

EXAMPLE 103

2-[(4-Methoxy-benzenesulfonyl)-(3-methoxy-benzyl)-amino]-3,5-dimethyl-benzoic acid methyl ester To a solution of 0.699 g (2.0 mmol) of the product of Example 62 in 5 mL of DMF was added 0.096 g (2.4 mmol) of 60% sodium hydride. The resulting mixture was stirred for 30 min at room temperature and then 0.376 g (2.4 mmol) of m-methoxybenzyl chloride and 0.089 g (0.24 mmol) of tetrabutylammonium iodide were added. The reaction mixture was stirred for 18 hr at room temperature, poured into water and then extracted with ether. The combined organics were washed with water and brine, dried over $MgSO_4$, filtered and concentad in vacuo. The crude solid was triturated with hexane to provide 0.768 g (82%) of the desired product as white solid. Electrospray Mass Spec 470.3 (M+H).

EXAMPLE 104

2-[(4-Methoxy-benzenesulfonyl)-(2,3,4,6-pentafluoro-benzyl)-amino]-3,5-dimethyl-benzoic acid methyl ester In the same manner as described in Example 9, 0.699 g (2.0 mmol) of the product of Example 62 and 0.626 g (2.4 mmol) of pentafluorobenzyl bromide provided 1.04 g (98%) of the desired product as a white solid after trituration with hexane and preparative TLC eluting with $CH_2Cl_2$. Electrospray Mass Spec 530.1 (M+H).

EXAMPLE 105

2-[(4-Methoxy-benzenesulfonyl)-propyl-amino]-3,5-dimethyl-benzoic acid methyl ester In the same manner as described in Example 9, 0.699 g (2.0 mmol) of the product of Example 62 and 0.295 g (2.4 mmol) of 1-bromopropane provided 0.691 g (88%) of the desired product as a yellow gum after preparative TLC eluting with 1:3 EtOAc:hexane. Electrospray Mass Spec 392.2(M+H).

EXAMPLE 106

2-[(2-Bromo-benzyl)-(4-methoxy-benzenesulfonyl)-amino]-3,5-dimethyl-benzoic acid methyl ester In the same manner as described in Example 9, 0.699 g (2.0 mmol) of the product of Example 62 and 0.6 g (2.4 mmol) of 2-bromobenzyl bromide provided 0.761 g (73%) of the desired product as a white solid after trituration with ether. Electrospray Mass Spec 518.1(M+H).

EXAMPLE 107

2-[(3-Bromo-benzyl)-(4-methoxy-benzenesulfonyl)-amino]-3,5-dimethyl-benzoic acid methyl ester In the same manner as described in Example 9, 0.699 g (2.0 mmol) of the product of Example 62 and 0.6 g (2.4 nunol) of m-bromobenzyl bromide provided 0.954 g (92%) of the desired product as a white solid after trituration with ether. Electrospray Mass Spec 518.1 (M+H).

EXAMPLE 108

2-[(4-Bromo-benzyl)-(4-methoxy-benzenesulfonyl)-amino]-3,5-dimethyl-benzoic acid methyl ester In the same manner as described in Example 9, 0.699 g (2.0 mmol) of the product of Example 62 and 0.6 g (2.4 mmol) of p-bromobenzyl bromide provided 0.896 g (86%) of the desired product as a white solid after trituration with hexane/ether. Electrospray Mass Spec 518.1 (M+H).

EXAMPLE 109

2-[(4-Methoxy-benzenesulfonyl)-(3-methoxy-benzyl)-amino]-3,5-dimethyl-benzoic acid To a solution of 0.610 g (1.3 mmol) of the product of Example 103 in 6.5 mL methanol and 6.5 mL of THF was added 6.5 mL of 1N NaOH solution. The reaction mixture was refluxed for 18 hr and the organics were removed in vacuo. The resulting mixture was diluted with water, acidified with 3N HCl and extracted with EtOAc. The combined organics were washed with water and brine, dried over $MgSO_4$, filtered and concentrated in vacuo. The resulting residue was triturated with ether and filtered to provide 0.417 g (79%) of the desired carboxylic acid as a white solid. Electrospray Mass Spec 456.3(M+H).

EXAMPLE 110

2-[(4-Methoxy-benzenesulfonyl)-(2,3,5,6-tetrafluoro-4-methoxy-benzyl)-amino]-3,5-dimethyl-benzoic acid In the same manner as described in Example 1109, 0.737 g (1.39 mmol) of the product of Example 104 provided 0.49 g (67%) of N-p-methoxy tetrafluroabenzyl derivative of the desired carboxylic acid after trituration with ether. Electmspray Mass Spec 528.1 (M+H).

EXAMPLE 111

2-[(4-Methoxy-benzenesulfonyl)-propyl-amino]-3,5-dimethyl-benzoic acid

In the same amn as described in Example 109, 0.602 g (1.54 mmol) of the product of Example 105 provided 0.461 g (79%) of the desired carboxylic acid as a white solid after trituration with ether/hexane. Electrospray Mass Spec 378.2 (M+H).

EXAMPLE 112

2-[(2-Bromo-benzyl)-(4-methoxy-benzenesulfonyl)-amino]-3,5-dimethyl-benzoic acid In the same manner as described in Example 109, 0.518 g (1.0 mmol) of the product of Example 106 provided 0.4 g (79%) of the desired carboxylic acid as a white solid after trituration with ether. Electrospray Mass Spec 504.0 (M+H).

EXAMPLE 113

2-[(3-Bromo-benzyl)-(4-methoxy-benzenesulfonyl)-amino]-3,5-dimethyl-benzoic acid In the same manner as described in Example 109, 0.894 g (1.725 mmol) of the product of Example 107 provided 0.61 g (70%) of the desired carboxylic acid after trituration with ether. Electrospray Mass Spec 506.0 (M+H).

EXAMPLE 114

2- [(4-Bromo-benzyl)-(4-methoxy-benzenesulfonyl)-amino]-3,5-dimethyl-benzoic acid In the same manner as described in Example 109, 0.836 g (1.61 mmol) of the product of Example 108 provided 0.584 g (72%) of the desired carboxylic acid as a white solid after trturation with ether. Electrospray Mass Spec 504 (M+H).

EXAMPLE 115

N-Hydroxy-2-[(4-methoxy-benzenesulfonyl)-(3-methoxy-benzyl)-amino]-3,5-dimethyl-benzamide In the same manner as described in Example 23, 0.364 g (0.8 mmol) of the product of Example 109 provided 0.245 g (65%) of the desired hydroxamic acid as a white solid after trituration with ether. Electrospray Mass Spec 471.3(M+H).

EXAMPLE 116

N-Hydroxy-2-[(4-methoxy-benzenesulfonyl)-(2,3,5,6-tetrafluoro-4-methoxy-benzyl)-amino]-3,5-dimethyl-benzamide In the same manner as described in Example 23, 0.369 g (0.7 mmol) of the product of Example 110 provided 0.253 g (67%) of the desired hydroxamic acid as a white solid after trituation with ether. Electrospray Mass Spec 543.1(M+H).

EXAMPLE 117

N-Hydroxy-2-[(4-methoxy-benzenesulfonyl)-propyl-amino]-3,5-dimethyl-benzamide

In the same manner as described in Example 23, 0.377 g (1.0 mmol) of the product of Example 111 provided 0.294 g (75%) of the desired hydroxamic acid as a white solid after trituration with ether. Electrospray Mass Spec 393.2(M+H).

EXAMPLE 118

2-[(2-Bromo-benzyl)-(4-methoxy-benzenesulfonyl)-amino]-N-hydroxy-3,5-dimethyl-benzamide In the same manner as described in Example 23, 0.353 g (0.7 mmol) of the product of Example 112 provided 0.205 g (56%) of the desired hydroxamic acid as a white solid after trituration with ether. Electrospray Mass Spec 519.1 (M+H).

EXAMPLE 119

2-[(3-Bromo-benzyl)-(4-methoxy-benzenesulfonyl)-amino]-N-hydroxy-3,5-dimethyl-benzamide In the same manner as described in Example 23, 0.546 g (1.08 mmol) of the product of Example 113 provided 0.397 g (71%) of the desired hydroxamic acid as a white solid after trituration with ether. Electrospray Mass Spec 517.0(M–H).

EXAMPLE 120

2-[(4-Bromo-benzyl)-(4-methoxy-benzenesulfonyl)-amino]-N-hydroxy-3,5-dimethyl-benzamide In the same manner as described in Example 23, 0.521 g (1.03 mmol) of the product of Example 114 provided 0.333 g (62%) of the desired hydroxamic acid as a white solid after trituration with ether. Electrospray Mass Spec 517.0(M–H).

EXAMPLE 121

N-Benzyl-4-methoxy-benzenesulfonamide

To a solution of 5.358 g (0.05 mole) of benzylamine and 7.755 g (0.06 mole) of N,N-diisopropylethylamine in 80 mL of $CH_2Cl_2$ at room temperatue was added slowly 11.365 g (0.055 mole) of 4-methoxybenzenesulfonyl chloride. The resulting mixture was stirred for 18 hr at room temperature and diluted with water. The organic layer was separated, washed with $NaHCO_3$, water, brine, dried over $MgSO_4$, filtered and concentrated. The residue was boiled in $CH_2Cl_2$:Hexane (1:4), cooled and filtered to provide 11.79 g (85%) of the desired product as a cream solid.

EXAMPLE 122

N-Benzyl-N-(2-cyano-6-trifluoromethyl-phenyl)-4-methoxy-benzenesulfonamide

To a solution of 3.05 g (11.0 mmol) of the product of Example 121 in 15 mL of DMF was added 0.484 g (12.1 mmol) of 60% sodium hydride. The resulting mixture was stirred for 30 min at room temperature and then 1.89 g (10.0 mmol) of 2-fluoro-3-(trifluoromethyl)benzonitrile in 2 mL of DMF was added. The reaction mixture was stirred at 90° C. for 18 hr, poured into water and extracted with ether. The combined organics were washed with water, brine, dried over $MgSO_4$, filtered and concentrated in vacuo. The crude solid was triturated with ether to provide 3.33 g (75%) of the desired product as a white solid. Electrospray Mass Spec 447.2(M+H).

EXAMPLE 123

2-[Benzyl-(4-methoxy-benzenesulfonyl)-amino]-3-trifluoromethyl-benzamide

To a solution of 1.78 g (4.0 mmol) of the product of Example 122 in 30 mL of n-propanol was added 8 mL of 5N NaOH solution. The resulting mixture was refluxed for 66 h and concentrated. The residue was stirred in water and filtered to provide 1.725 g (93%) of the desired amide as a white solid. Electrospray Mass Spec 465.2(M+H).

EXAMPLE 124

2-[Benzyl-(4-methoxy-benzenesulfonyl)-amino]-3-trifluoromethyl-benzoic acid

To a suspension of 0.192 g (0.41 mmol) of the product of Example 123 in 2.5 mL of dry $CH_3CN$ was added 0.068 g(0.58 mmol) of nitrosonium tetrafluoroborate. The resulting mixture was stirred for 1 h and then added 0.040 g(0.34 mmol) of the same reagent and stirred for additional 1 h. The reaction was quenched with water and filtered to provide 0.141 g (74%) of the desired carboxylic acid as a white solid. Electrospray Mass Spec 466.2(M+H).

EXAMPLE 125

2-[Benzyl-(4-methoxy-benzenesulfonyl)-amino]-N-hydroxy-3-trifluoromethyl-benzamide In the same manner as described in Example 23, 0.17 g (0.365 mmol) of the product of Example 124 provided 0.79 g (45%) of the desired hydroxamic acid as a cream solid. Electrospray Mass Spec 481.1 (M+H).

EXAMPLE 126

2-[(4-Metboxy-benzenesulfonyl)-methyl-amino]-3,5-dimethyl-benzoic acid methyl ester In the same manner as described in Example 9, 0.30 g (0.860 mmol) of the product of Example 62 and 0.08 mL (1.289 mmol) of iodomethaie provided 0.3 g (96%) of the desired product as a white solid. Electrospray Mass Spec 364.3(M+H).

EXAMPLE 127

2-[Ethyl-(4-methoxy-benzenesulfonyl)-amino]-3,5-dimethyl-benzoic acid methyl ester In the same manner as described in Example 9, 0.30 g (0.860 mmol) of the product of Example 62 and 0.103 mL (1.289 mmol) of iodoethane provided 0.324 g (100%) of the desired product as a white solid. Electrospray Mass Spec 378.2(M+H).

EXAMPLE 128

2-[(4-Methoxy-benzenesulfonyl)-methyl-amino]-3,5-dimethyl-benzoic acid

In the same manner as described in Example 18, 0.267 g (0.738 mrmol) of the product of Example 126 provided 0.23 g (89%) of the desired product as a white solid. Electrospray Mass Spec 350.1(M+H).

EXAMPLE 129

2-[Ethyl-(4-methoxy-benzenesulfonyl)-amino]-3,5-dimethyl-benzoic acid

In the same manner as described in Example 18, 0.254 g (0.674 mmol) of the product of Example 127 provided 0.207 g (84%) of the desired product as a white solid. Electrospray Mass Spec 364.2(M+H).

EXAMPLE 130

N-Hydroxy-2-[(4-methoxy-benzenesulfonyl)-methyl-amino]-3,5-dimethyl-benzamide

In the same manner as described in Example 23, 0.194 g (0.557 mmol) of the product of Example 128 provided 0.140 g (69%) of the desired product as a white solid. Electrospray Mass Spec 365.3(M+H).

EXAMPLE 131

2-[Ethyl-(4-methoxy-benzenesulfonyl)-amino]-N-hydroxy-3,5-dimethyl-benzamide

In the same manner as described in Example 23, 0.175 g (0.482 mmol) of the product of Example 129 provided 0.142 g (78%) of the desired product as a white solid. Electrospray Mass Spec 379.2(M+H).

EXAMPLE 132

2-Amino-5-bromo-3-methyl-benzoic acid

To a mixture of 1.5 g (10 mmol) of 3-methyl-2-amino benzoic acid in 50 mL of glacial acetic acid was added 1.6 g (10 mmol) of Iromine and the resulting mixture was stirred at room temperature for 5 h. The reaction mixture was then poured into water and the precipitated solid was filtered, washed with water and air dried to provide 2.2 g (95%) of the desired product as a brown solid. m.p.245° C. Electrospray Mass Spec 232 (M+H).

EXAMPLE 133

2-Amino-5-bromo-3-methyl-benzoic acid methyl ester

To 20 mL of 50% $BF_3$:MeOH complex was added 2.3 g (10 mmol) of the product of Example 132 and the mixture was heated to reflux for 48 h. The reaction mixture was then cooled to room temperature, concentrated in vacuo, diluted with ice water and neutralized with 1N NaOH solution. The resulting mixture was extracted with chloroform, and the combined organics were washed with water, dried over $MgSO_4$, filtered and concentrated in vacuo to provide 2.3 g (93%) of the desired product as a brown semi-solid. Electrospray Mass Spec 246 (M+H).

Example 134

5-Bromo-2-(4-methoxy-benzenesulfonylamino)-3-methyl-benzoic acid methyl ester

To a stirred solution of 24.5 g (100 mmol) of the product of Example 133 in 100 mL of pyrdine was added 21.0 g (100 mmol) of p-methoxybenzenesulfonyl chloride and the resulting mixture was heated to 80° C. for 24 h. The reaction mixture was then quenched with ice cold water and acidified with concentrated HCl. The resulting mixture was extracted with chloroform, washed with water, dried over MgSO$_4$, filtered and concentrated in vacuo. The residue was triteretd with diethyl ether, filtered and dried to provide 35 g (84%) of the desired product as a brown solid. Electrospray Mass Spec 416, (M+H).

EXAMPLE 135

3-Bromo-2-(4-methoxy-benzenesulfonylamino)-5-methyl-benzoic acid methyl ester

To a solution of 2.4 g (10 mmol) of methyl 2-amino-3-bromo-5-methyl benzoate in 20 mL of pyridine was added 2.1 g (10 mmol) of p-methoxybenzenesulfonyl chloride. The reaction mixture was then heated to 70° C. for 16 h and then poured into ice water and acidified with concentrated hydrochloric acid to pH2. The resulting mixture was extracted with chloroform, washed with water, dried over anhydrous MgSO$_4$, filtered and conntrated in vacuo. The residue was triturated with ether, filtered and dried to provide 3.8 g (92%) of the desired product as a brown solid. m.p. 113° C. Electrospray Mass Spec: 416 (M+H).

EXAMPLE 136

3-Bromo-2-[(4-methoxy-benzenesulfonyl)-pyridin-3-ylmethyl-amino]-5-methyl-benzoic acid methyl ester To a sired solution of 2.0 g (4.8 nmnol) of the product of Example 135 in 20 mL of DMF was added 1.0 g (10 mmol) of K$_2$CO$_3$ and 1.1 g (7.2 mmol) of 3-picolyl chloride hydrochloride. The reaction niixture was stirred for 48 h at room tempera and then diluted with water. The resulting mixture was extracted with chloroform and the combined organic layers were washed with water, dried over MgSO$_4$, filtered and concentraed in vacuo. The residue was purified by chromatography on silica gel eluting with ethyl acetate. hexane (1:1) to provide 2.90 g (82%) of the desired product as a brown oil. Electrospray Mass Spec: 508 (M+H).

EXAMPLE 137

3-Bromo-2-[(4-methoxy-benzenesulfonyl-pyridin-3-ylmethyl)-amino]-5-methyl-benzoic acid In the same manner as described in Example 16, 1.01 g (2 mmol) of the product of Example 136 provided 0.90 g (91%) of the desired product as a white powder after neutraliation of the reaction mixture with acetic acid and extraction with ethyl acetate. m.p.198° C. Electrospray Mass Spec: 494 (M+H).

EXAMPLE 138

3-Bromo-N-hydroxy-2-[(4-methoxy-benzenesulfonyl)-pyridin-3-ylmethyl-amino]-5-methyl-benzamide In the same manner as described in Example 23, 0.986 g (2 mmol) of the product of Example 137 provided 0.61 g (60%) of the title product. The corresponding hydrochloride salt was prepared in quantitative yield by bubbling HCl gas through a methanolic solution of the free base, followed by concentrating the reaction mixture in vacuo to provide a yellow spongy solid. m.p.87° C. Electrospray Mass Spec: 509 (M+H).

EXAMPLE 139

2-(4-Methoxy-benzenesulfonylamino)-3-methyl-5-thiophen-2-yl-benzoic acid methyl ester To a solution of 3.0 g (7.2 mmol) of the product of Example 134 in 200 mL of degassed toluene was added 3.54 g (10 mmol) of 2-thienyl tdbutyltin and 0.50 g of tetmis (triphenylphosphine)palladium and the resulting mixture was refluxed for 16 h. The reaction mixture was then filtered through celite and the filtrate was concentrated in vacuo. The residue was chromatographed on silica gel eluting with 30% ethylacetate:hexane to provide 2.5 g (83%) of the desired product as a gray solid. m.p.91° C. Electrospray Mass Spec: 417 (M+H).

EXAMPLE 140

2-[(4-Methoxy-benzenesulfonyl)-pyridin-3-ylmethyl-amino]-3-methyl-5-thiophen-2-yl-benzoic acid methyl ester In the same manner as described in Example 136, 0.832 g (2.0 mmol) of the product of Example 139 provided 0.920 g of the desired product as a brown oil. Electrospray Mass Spec: 509 (M+H).

EXAMPLE 141

2-[(4-Methoxy-benzenesulfonyl)-pyridin-3-ylmethyl-amino]-3-methyl-5-thiophen-2-yl-benzoic acid In the same manner as described in Example 18, 0.800 g (1.5 mmol) of the product of Example 140 provided 0.70 g (94%) of the desired product as a white solid. m.p.191° C. Electrospray Mass. Spec: 495 (M+H).

EXAMPLE 142

2-(4-Methoxy-benzenesulfonylamino)-5-methyl-3-thiophen-2-yl-benzoic acid methyl ester In the same manner as described in Example 39, 3.0 g (7.2 mmol) of the product of Example 135 provided 2.0 g (66%) of the desired product as a gray solid after chromatography on silica gel eluting with 30% ethyl acetate:hexane. m.p.141° C. Electrospray Mass Spec: 418 (M+H).

EXAMPLE 143

2-[(4-Methoxy-benzenesulfonyl)-pyridin-3-ylmethyl-amino]-5-methyl-3-thiophen-2-yl-benzoic acid methyl ester In the same manner as described in Example 136, 2.0 g (4.8 mmol) of the product of Example 142 provided 2.1 g (87%) of the desired product as a brown oil after chromatography on silica gel eluting with 50% ethyl acetate:hexane. Electrospray Mass Spec: 509 (M+H).

Example 144

2-[(4-Methoxy-benzenesulfonyl)-pyridin-3-ylmethyl-amino]-5-methyl-3-thiophen-2-yl-benzoic acid In the same manner as described in Example 16 starting with 1.5 g (2.9 mmol) of the product of Example 143 provided 1.3 g (86%) of the desired product as a white powder after neutralization of the reaction mixture with acetic acid and extraction with ethyl acetate. m.p.67° C. Electrospray Mass Spec: 495 (M+H).

EXAMPLE 145

N-Hydroxy-2-[(4-methoxy-benzenesulfonyl)-pyridin-3-ylmethyl-amino]-5-methyl-3-thiophen-2-yl-benzamide In the same manner as described in Example 23, 1.0 gm (2.02 mmol) of the product of Example 144 provided 0.70 g (63%) of the desired product. The corresponding hydrochloride salt was prepared in quantitative yield by bubbling HCl gas through a methanolic solution of the free base, followed by concentrating the reaction mixture in vacuo to provide a yellow spongy solid. m.p.94° C. Electrospray Mass Spec: 547 (M+H).

EXAMPLE 146

2-[(4-Methoxy-benzenesulfonyl)-methyl-amino]-3,5-dimethyl-benzoic acid methyl ester In the same manner as described in Example 9, 0.30 g (0.860 mmol) of the product of Example 62 was alkylated with methyl iodide to give 0.30 g (96%) of the desired product as a white solid. Electrospray Mass Spec: 364 (M+H).

EXAMPLE 147

2-[Ethyl-(4-methoxy-benzenesulfonyl)-amino]-3,5-dimethyl-benzoic acid methyl ester In the same manner as described in Example 9, 0.30 g (0.860 mmol) of the product of Example 62 was alkylated with ethyl iodide to give 0.324 g (100%) of the desired product as a white solid. Electrospray Mass Spec: 378 (M+H).

EXAMPLE 148

2-[(4-Methoxy-benzenesulfonyl)-methyl-amino]-3,5-dimethyl-benzoic acid

In the same manner as described in Example 18, 0.267 g (0.738 mmol) of the product of Example 146 gave 0.23 g (89%) of the desired product as a white solid. Electrospray Mass Spec: 350 (M+H).

EXAMPLE 149

2-[Ethyl-(4-methoxy-benzenesulfonyl)-amino]-3,5-dimethyl-benzoic acid

In the same manner as described in Example 18, 0.254 g (0.674 mmol) of the product of Example 147 gave 0.207 g (84%) of the desired product as a white solid. Electrospray Mass Spec: 364 (M+H).

EXAMPLE 150

N-Hydroxy-2-[(4-methoxy-benzenesulfonyl)-methyl-amino]-3,5-dimethyl-benzamide

In the same manner as described in Example 23, 0.194 g (0.557 mmol) of the product of Example 148 gave 0.140 g (69%) of the desired product as a pink solid. Electrospray Mass Spec: 365 (M+H).

EXAMPLE 151

2-[Ethyl-(4-methoxy-benzenesulfonyl)-amino]-N-hydroxy-3,5-dimethyl-benzamide

In the same manner as described in Example 23, 0.175 g (0.482mnol) of the product of Example 149 gave 0.142 g (78%) of the desired product as a white solid. Elec pray Mass Spec: 379 (M+H).

EXAMPLE 152

3,4,5-Trimethoxy-2-(4-methoxy-benzenesulfonylamino)-benzoic acid methyl ester

In the same manner as described in Example 31, 2.0 g (8.289 mmol) of methyl-3,4,5-trimethylanthranilate gave 1.945 (57%) of the desired product as a white solid. Electrospray Mass Spec: 412 (M+H).

EXAMPLE 153

3,4,5-Trimethoxy-2-[(4-methoxy-benzenesulfonyl)-pyridin-3-ylmethyl-amino]-benzoic acid methyl ester In the same manner as described in Example 45, 0.60 g (1.46 mmol) of the product of Example 152 gave 0.716 g (98%) of the desired product as a brown oil. Electrospray Mass Spec: 503 (M+H).

EXAMPLE 154

2-[Benzyl-(4-methoxy-benzenesulfonyl)-amino]-3,4,5-trimethoxy-benzoic acid methyl ester In the same manner as described in Exampk 9, 0.60 g (1.46 mmol) of the product of Example 152 gave 0.669 g (92%) of the desired product as a white solid. Electrospray Mass Spec: 502 (M+H).

EXAMPLE 155

2-[Benzyl-(4-methoxy-benzenesulfonyl)-amino]-3,4,5-trimethoxy-benzoic acid

In the same manner as described in Example 18, 0.594 g (1.186 mmol) of the product of Example 154 gave 0.532 g (92%) of the desired product as a white solid. Electay Mass Spec: 488 (M+H).

EXAMPLE 156

2-[Benzyl-(4-methoxy-benzenesulfonyl)-amino]-N-hydroxy-3,4,5trimethoxy-benzamide In the same manner as described in Example 23, 0.463 g (0.951 mmol) of the product of Example 155 gave 0.353 g (74%) of the desired product as a white solid. Electrospray Mass Spec: 503 (M+H).

EXAMPLE 157

3,4,5-Trimethoxy-2-[(4-methoxy-benzenesulfonyl)-pyridin-3-ylmethyl-amino]-benzoic acid In the same manner as described in Example 53, 0.640 g (1.275 mrol) of the product of Example 153 gave 0.631 g (100%) of the desired product as a tan foam. Eiectrospray Mass Spec: 489 (M+H).

EXAMPLE 158

N-Hydroxy-3,4,5-trimethoxy-2-[(4-methoxy-benzenesulfonyl)-pyridin-3-ylmethyl-amino]-benzamide In the same manner as described in Example 61, 0.549 g (1.109 mmol) of the product of Example 157 gave 0.395 g (71%) of the desired product as a brown foam. Electrospray Mass Spec: 504 (M+H).

EXAMPLE 159

12-(4-Methoxy-benzenesulfonyl)-11,12-dihydro-6H-dibenz[b,f][1,4]oxazocine-1-carboxylic acid methyl ester To a solution of 0.350 g (1.039 mmol) of the product of Example 31 in 35 mL of DMF was added 0.104 g (2.596 mmol) of 60% sodium hydride and the solution was stirred at room temperature for 15 minutes. To the resulting mixture was then added 0.384 g (1.454 mmol) of a,a'-dibromo-o-xylene and the reaction mixture was then heated to 80° C. for 18 h, cooled to room temperature, diluted with ether and washed with water. The combined organic layers were dried over MgSO$_4$, filtered and concentrated in vacuo. The resulting residue was chromatographed on silica gel eluting with EtOAc/hexanes (1:3) to provide 0.358 g (79%) of the desired product as a white solid. Electrospray Mass Spec: 440 (M+H).

EXAMPLE 160

6-(4-Methoxy-benzenesulfonyl)-3,4,5,6-tetrahydro-2H -1,6-benzoxazocine-7-carboxylic acid methyl ester In the same manner as described in Example 159, 0.400 g (1.187 mmol) of the product of Example 31 and 0.198 mL (1.662 mmol) of 1,4-dibromobutane provided 0.139 g (30%) of the desired product as a white solid. Electrospray Mass Spec: 392 (M+H).

EXAMPLE 161

5-(4-Methoxy-benzenesulfonyl)-2,3,4,5-tetrahydro-[1,5]benzoxazepine-6-carboxylic acid methyl ester In the same manner as described in Example 159, 0.300 g (0.890 mmol) of the product of Example 31 and 0.127 mL (1.246 mmol) of 1,3-dibromopropane provided 0.156 g (46%) of the desired product as a colorless oil. Electrospray Mass Spec: 378 (M+H).

EXAMPLE 162

5-(4-Methoxy-benzenesulfonyl)-2,3,4,5-tetrahydro-1,5-benzoxazepine-6-carboxylic acid In the same manner as described in Example 18, 0.174 g (0.462 mmol) of the product of Example 161 provided 0.133 g (79%) of the desired product as a white solid. Electrospray Mass Spec: 364 (M+H).

EXAMPLE 163

12-(4-Methoxy-benzenesulfonyl)-11,12-dihydro-6H-dibenz[b,f][1,4]oxazocine-1-carboxylic acid In the same manner as described in Example 18, 0.306 g (0.697 mmol) of the product of Example 159 provided 0.261 g (88%) of tie desired product as a white solid. Electrospray Mass Spec: 426 (M+H).

EXAMPLE 164

6-(4-Methoxy-benzenesulfonyl)-3,4,5,6-tetrahydro-2H-1,6-benzoxazocine-7-carboxylic acid In the same manner as described in Example 18, 0.125 g (0.320 mmol) of the product of Example 160 provided 0.106 g (88%) of the desired product as a white solid Electrospray Mass Spec: 378 (M+H).

EXAMPLE 165

5-(4-Methoxy-benzenesulfonyl)-2,3,4,5-tetrahydro-1,5-benzoxazepine-6-carboxylic acid hydroxyamide In the same manner as described in Example 23, 0.107 g (0.295 mmol) of the product of Example 162 provided 0.100 g (90%) of the desired product as a white solid. Electrospray Mass Spec: 379 (M+H).

EXAMPLE 166

12-(4-Methoxy-benzenesulfonyl)-11,12-dihydro-6H-dibenz[b,f][1,4]oxazocine-1-carboxylic acid hydroxyamide In the same manner as described in Example 23, 0.230 g (0.541 mmol) of the product of Example 163 provided 0.192 g (81%) of the desired product as a white solid. Elecray Mass Spec: 441 (M+H).

EXAMPLE 167

6-(4-Methoxy-benzenesulfonyl)-3,4,5,6-tetrahydro-2H-1,6-benzoxazocine-7-carboxylic acid hydroxyamide In the same manner as described in Example 23, 0.081 g (0.215 nmnol) of the product of Example 164 provided 0.074 g (88%) of the desired product as a white solid. Electrospray Mass Spec: 393 (M+H).

EXAMPLE 168

2-[Benzyl-(4-methoxy-benzenesulfonyl)-amino]-3-nitro-benzoic acid methyl ester

To a solution of 29.5 g (0.092mol) of the product of Example 1 suspended in 131 mL of acetic anhydride at 0° C. was dropwise added a mixture of 17.5 mL of acetic anhydride, 22.5 mL of 70% nitric acid and 15.75 mL of acetic acid over 1 hour. The reaction was stirred at 0° C. for an additional 2 h and then poured into ice water. The precipitate was filtered and washed with ether. The filtrate was transferred to a separatory funnel and the layers were separated. The aqueous layer was washed with chloroform and the combined organics were dried over MgSO$_4$, filtered and concentred in vacuo. The residue was chromatographed on silica gel eluting with EtOAc/Hexanes (1:10) to provide 1.03 g of the nitro-sulfonamide as a yellow solid.

0.250 g (0.683 mmol) of the sulfonamide reacted with sodium hydride and benzyl bromide in the same manner as described in Example 9 to provide 0.215 g (69%) of the desired product as a pale yellow solid. Electrospray Mass Spec: 457 (M+H).

EXAMPLE 169

2-[Benzyl-(4-methoxy-benzenesulfonyl)-amino]-3-nitro-benzoic acid

In the same manner as described in Example 18, 0.199 g (0.436 mmol) of the product of Example 168 provided 0.172 g (89%) of the desired product as a pale yellow solid. Electrospray Mass Spec: 443 (M+H).

EXAMPLE 170

2-[Benzyl-(4-methoxy-benzenesulfonyl)-amino]-N-hydroxy-3-nitro-benzamide

In the same manner as described in Example 23, 0.136 g (0.308 mmol) of the product of Example 169 provided 0.106 g (75%) of the desired product as a tan foam. Electropray Mass Spec: 458 (M+H).

EXAMPLE 171

2-[Benzyl-(4-methoxy-benzenesulfonyl)-amino]-3-[3-(tert-butyl-dimethyl-silanyloxy)-propoxy]-benzoic acid methyl ester In the same manner as described in Example 38, 0.35 g (0.820 mmol) of the product of Example 37 and 0.290 g (1.147 mmol) of 1-t-butyldimethylsilyloxy-3-bromopropane provided 0.355 g (72%) of the desired product as a colorless oil. Electrospray Mass Spec: 600 (M+H).

EXAMPLE 172

2-[Benzyl-(4-methoxy-benzenesulfonyl)-amino]-3-(3-hydroxy-propoxy)-benzoic acid

In the same manner as described in Example 18, 0.310 g (0.518 mmol) of the product of Example 171 provided 0.188 g (77%) of the desired product as a white foam. Electrpray Mass Spec: 470 (M–H).

EXAMPLE 173

2-[Benzyl-(4-methoxy-benzenesulfonyl)-amino]-3-[3-(tert-butyl-dimethyl-silanyloxy)-propoxy]-benzoic acid To a solution of 0.145 g (0.308 mmol) of the product of Example 172 in 5.0 mL of DMF was added 0.105 g (1.539 mmol) of iidazle and 0.111 g (0.739 mmol) of t-butyidimethylsilyl chloride. The reaction was stirred at room temperature for 18 h and then 0.40 mL of 1N sodium hydroxide solution was added and the resulting mixture was sired for 1 h. The reaction mixture was then diluted with water, acidified with 5% HCl solution and extted with EtOAc. The combined organics were washed with water, dried over $MgSO_4$, filtered and concentrated in vacuo. The residue was chromatographed on silica gel eluting with EtOAc/Hexanes to provide 0.089 g (50%) of the desired product as a white foam. Electrospray Mass Spec: 586 (M+H).

EXAMPLE 174

2-[Benzyl-(4-methoxy-benzenesulfonyl)-amino]-N-hydroxy 3-(3-hydroxy-propoxy)-benzamide In the same manner as described in Example 23, 0.073 g (0.125 mmol) of the product of Example 173 provided 0.038 g (62%) of the desired product as a white solid. Electrospray Mass Spec: 487 (M+H).

EXAMPLE 175

N-Hydroxy-2-[(4-methoxybenzenesulfonyl)-pyridin-3-ylmethyl-amino]-3-methyl-5-thiophen-2-yl benzamide In the same manner as described in Example 23, 0.600 g (1.2 mmol) of the product of Example 141 provided 0.520 g (79%) of the desired product after chromatography on silica gel eluting with 5% MeOH:Ethyl acetate. The corresponding hydrochloride salt was prepared in quantitative yield by bubbling HCl gas through a methanolic solution of the free base, followed by concentrating the reaction mixture in vacuo to provide a yellow spongy solid. m.p.106° C. Electrospray Mass Spec: 547 (M+H).

EXAMPLE 176

3-Cyano-2-(4-methoxybenzenesulfonylamino)-5-methylbenzoic acid

To a solution of 4.0 g (10 mmol) of the product of Example 135 in 60 ml of pyridine was added 2.0 g (22 mmol) of copper (I) cyanide and the mixture was refluxed for 48 h. The reaction mixture was then cooled to room tempera and poured over cold water. The resulting mixture was stirred for sixteen hours and carefully acidified with concentted HCl solution. The resulting precipitate was filtered and washed with water, dissolved in chloroform, filtered and concentrated. The residue was triturated with ether, filtered and dried to provide 2.5 g (72%) of the desired product as a white solid. m.p. 162° C.; Electrospray Mass Spec 347 (M+H).

EXAMPLE 177

2-[Benzyl-(4-methoxybenzenesulfonylamino)-3-cyano-5-methylbenzoic acid

To a solution of 1.5 g (4.3 mmol) of the product of Example 176 in 200 mL of acetone was added 4 g of $K_2CO_3$ and 5 ml of benzylbromide and the mixture was refluxed for 8 hours. The reaction mixture was then filtered and the acetone was removed in vacuo. The residue was dissolved in chloroform and washed well with water. The organic layer was then dried over $MgSO_4$, filtered and concentrated in vacuo. The resulting residue chromatographed on silica gel luting with 30% Ethyl acetateexane to give 1.8 g (79%) of the desired product as a brown oil. Electrospray Mass Spec 527 (M+H).

EXAMPLE 178

2-[Benzyl-(4-methoxybenzenesulfonylamino)-3-cyano-5-methyl-benzoic acid

To a solution of 1.5 g (2.8 mmol) of the product of Example 177 in 100 mL of ThF:MeOH (1:1) was added 10 mL of 10N NaOH. The reaction mixture was stired at room temperature for 8 h and then concentrated in vacuo. The residue was neutlized with concentrated HCl and the resulting separated solid was dissolved in chloroform and washed well with water. The organic layer was dried over $MgSO_4$, filtered and concentrated. The resulting solid was triturated with ether and filtered to provide 1.1 g (91%) of the desired product as a brown solid. Electrospray Mass Spec 437 (M+H).

EXAMPLE 179

2-[Benzyl-(4-methoxybenzenesulfonylamino)-N-hydroxy-3-cyano-5-methyl-benzamide

In the same manner as described in Example 23, 1.0 g (2.3 mmol) of the product of Example 178 provided 0.70 g (67%) of the desired product as a white solid. m.p. 175° C.; Electrospray Mass Spec 452 (M+H).

EXAMPLE 180

5-Cyano-2-(4-methoxybenzenesulfonylamino)-3-methyl-benzoic acid

To a solution of 4.0 g (10 mmol) of the product of Example 10 in 60 mL of pyridi was added 2.0 g (22 mmol) of copper (I) cyanide and the resulting mixture was refluxed for 48 h. The reaction mixture was then cooled to room temperature, poured over cold water, stirred for 16 h and then carefully acidified with concentrated HCl solution. The resulting solid was filtered and washed with water, dissolved in chloroform, dried over $MgSO_4$, filtered and concentrated in vacuo. The residue was triturated with ether, filtered and dried to provide 2.0 g (58%) of the desired product as a white solid. m.p. 175° C.; Electrospray Mass Spec 347 (M+H).

EXAMPLE 181

2-[Benzyl-(4-methoxybenzenesulfonylamino)-5-cyano-3-methylbenzoic acid

In the same manner as described in Example 177, 4.5 g (13 mmol) of the product of Example 180 and 5 mL of benzylbromide provided 3.5 g (51%) of the desired product as brown solid after trituration with ether. m.p. 123° C.; Electrospray Mass Spec 527 (M+H).

EXAMPLE 182

2-[Benzyl-(4-methoxybenzenesulfonylamino)-5-cyano-3-methyl-benzoic acid

In the same manner as described in Example 178, 3.0 g (5.7 mmol) of the product of Example 215 provided 2.2 g (88%) of the desired product as a brown semi-solid. Electrospray Mass Spec 437 (M+H).

EXAMPLE 183

3-Furan-2-yl-2-(4-methoxybenesulfonylamino)-5-methyl-benzoic acid methyl ester

To a solution 4.1 g (10 mmol) of the product of Example 135 in 300 mL of degassed toluene was added 6.0 g (16 mmol) of 2-(tributylstannyl)furan and 500 mg of tetrakis (triphenylphosphine)palladium(0) and the resulting mixture was heated to reflux for 24 h. The reaction mixture was then cooled, filtered through celite and concentrated in vacuo. The resulting residue was triturated with either to provide 3.5 g (87%) of the desired product as a grey solid. m.p. 133° C.; Electrospray Mass Spec 402 (M+H).

EXAMPLE 184

3-Furan-2-yl-2-[(4-methoxybenzenesulfonyl)-pyridin-3-ylmethylamino]-5-methyl-benzoic acid methyl ester To a solution of 3.0 g (7.4 mmol) of the product of Example 183 in 25 mL of DMF was added 1.64 g (10 mmol) of 3-picolyl chloride hydrochloride and 4.0 g of $K_2CO_3$ and the resulting mixture was stirred for 72 h at room temperature. The reaction mixture was then poured over water, extracted with chloroform and washed well with water. The organic layer was dried over anhydrous $MgSO_4$, filtered and concentratedin vacuo. The residue was chromatographed on silica gel eluting with 50% ethyl acetate/hexane to provide 2.5 g (68%) of the desired product as a brown oil. Electrospray Mass Spec 493 (M+H).

EXAMPLE 185

3-Furan-2-yl-2-[(4-methoxybenzenesulfonyl)-pyridin-3-ylmethylamino]-5-methyl-benzoic acid In the same manner as descibed in Example 24 2.0 g (4.0 mmol) of the product of Example 184 provided 1.5 g (79%) of the desired product as a brown solid. m.p. 82° C.; Electrospray Mass Spec 479 (M+H).

EXAMPLE 186

3-Furan-2-yl-N-hydroxy-2-[(4-methoxybenzenesulfonyl)-pyridin-3-ylmethylamino]-5-methyl-benzamide In the same manner as described in Example 23, 1.0 g (2.01 mmol) of the product of Example 185 provided 0.60 g (58%) of the desired product as a white solid after chroatography on silica gel eluting with ethyl acetate/methanol (95:5) m.p. 160° C.; Electrosray Mass Spec 494 (M+H).

EXAMPLE 187

2-[(4-Methoxybenzenesulfonyl)-methylamino]-3-methyl-benzoic acid methyl ester

To a solution of 1.0 g (2.985 mmol) of the product of Example 3 in 10 mL of DMF was added 0.149 g (3.731 mmol) of 60% sodium hydride. The resulting mixture was stirred for 30 minutes at room temperature and then 0.28 mL (4.478 mmol) of iodomethane was added. The reaction was then stirred for 18 h, and next diluted with ether. The organics were washed with water, dried over $MgSO_4$, filtered and concentrated in vacuo to provide a white solid. The solid was washed with ether/hexanes (1:1) to give 0.788 g (76%) of the desired product as a white solid. Electrospray Mass Spec: 350.1 (M+H).

EXAMPLE 188

3-Bromomethyl-2-[(4-methoxybenzenesulfonyl)-methylamino]-benzoic acid methyl ester To a solution of 0.723 g (2.072 mmol) of the product of Example 187 in 70 mL of carbon tetrachloride was added 0.406 g (2.279 mmol) of N-bromosuccinimide and 0.14 g of dibenzoyl peroxide. The resulting mixture was heated to reflux for 18 h and then cooled to room temperature, washed with sodium bisulfite solution and water, dried over $MgSO_4$, filtered and concentrated in vacuo. The residue was titurad with ether/hexanes (1:1) and then filtered to provide 0.504 g (57%) of the desired product as a white solid. Electrspray Mass Spec: 428 (M+H).

EXAMPLE 189

3-Diethylaminomethyl-2-[(4-methoxybenzenesulfonyl)-methylamino]benzoic acid methyl ester To a solution of 0.25 g (0.584 nmol) of the product of Exmple 188 in 2.0 mL of DMF was added 0.242 g (1.752 mrol) of potassium carbonate, 0.066 mL (0.643 mmol) of diethylamine and 2 mg of tetrabutylanmonium iodide. The reaction mixture was then stirred at room temperature for 5 h, diluted with water and extracted with ether. The organics were then extracted with 6N HCl solution and the aqueous acid layer was then basified with 6N NaOH solution and then extracted with ether. The resulting ether layer was died over sodium sulfate, filtered and concentrated in vacuo to provide 0.19 g (78%) of the desired product as a colorless oil. Electrospray Mass Spec: 421.3 (M+H)$^+$

EXAMPLE 190

3-Diethylaminomethyl-2-[(4-methoxybenzenesulfonyl)-methylamino]benzoic acid

To a solution of 0.158 g (0.376 mmol) of the product of Example 189 in 4.0 mL of THF/water/MeOH (1:1:0.5) was added 0.032 g (0.752 mmol) of lithium hydroxide amonohydrate and the resulting mixture was then heated to reflux for 18 h, cooled to room temperature and concentrated in vacuo. The residue was washed with THF and filtered, and the filtrate was then concentrated and dried in vacuo to provide 0.132 g (85%) of the lithium salt of the tide compound as a white foam. Electrospray Mass Spec: 407.2 (M+H)+

EXAMPLE 191

3-Diethylaminomethyl-N-hydroxy-2-[(4-methoxybenzenesulfonyl)-methylamino]benzamide In the same manner as described in Example 61, 0.110 g (0.267 mmol) of the product of Example 190 provided 0.125 g (100%) of the hydrochloride salt of the tide comod as a brown foam. Electrospray Mass Spec: 422.1 (M+H)+.

EXAMPLE 192

2-[(4-methoxybenzenesulfonyl)-methylamino]-3-(4-methylpiperazin-1-ylmethyl)-benzoic acid methyl ester In the same manner as described in Example 189, 0.500 g (1.168 mmol) of the product of Example 188 and 0.143 mL (1.285 mmol) of N-methylpiperazine provided 0.368 g (70%) of the desired product as a tan solid. Electrospray Mass Spec: 448.0 (M+H)+

EXAMPLE 193

2-[(4-methoxybenzenesulfonyl)-methylamino]-3-(4-methylpiperazin-1-ylmethyl)-benzoic acid In the same manner as described in Example 190, 0.310 g (0.693 mmol) of the product of Example 192 provided 0.305 g (100%) of the lithium salt of the tide compound as a white foam Electrospray Mass Spec: 432.1 (M–H)−

EXAMPLE 194

N-Hydroxy-2-[(4-methoxybenzenesulfonyl)-methylamino]-3-(4-methylpiperazin-1-ylmethyl)-benzamide In the same manner as described in Example 61, 0.150 g (0.334 mmol) of the product of Example 193 provided 0.174 g (100%) of the hydrochloride salt of the title compound as a brown solid. Electrospray Mass Spec: 448.9 (M+H)+

EXAMPLE 195

2-[Benzyl-(4-methoxybenzenesulfonyl)amino]-3-(1-ethoxycarbonyl-1-methylethoxy-benzoic acid methyl ester To a solution of 0.250 g (0.585 mm01) of the product of Example 37, in 10 mL of DMF was added 2.42 g (17.56 mmol) of potassium carbonate and 0.86 mL (5.854 mmol) of ethyl 2-bromoisobutyrate. The resulting mixture was heated to 80° C. for 18 h and then cooled to room temperature and diluted with ether. The organics were washed with water, dried over $MgSO_4$, filtered and concentrated in vacuo to provide 0.186 g (59%) of the desired product as a white solid. Electrospray Mass Spec: 442.2 (M+H)+·

EXAMPLE 196

2-[Benzyl-(4-methoxybenzenesulfonyl)amino]-3-(1-ethoxycarbonyl-1-methylethoxy-benzoic acid In the same manner as described in Example 9, 0.147 g (0.272 mmol) of the product of Example 195 provided 0.107 g (79%) of the desired product as a white solid. Electrospray Mass Spec: 500.2 (M+H)+

EXAMPLE 197

2-[Benzyl-(4-methoxybenzenesulfonyl)amino]-3-(1-ethoxycarbonyl-N-hydroxy-1-methylethoxy-benzamide In the same manner as described for Example 23, 0.085 g (0.170 mmol) of the product of Example 196 provided 0.052 g (58%) of the desired product as a white solid. Electrospray Mass Spec: 530.1 (M+H)+

EXAMPLE 198

3-Bromo-2[-(4-methoxybenzenesulfonyl)amino]-benzoic acid methyl ester

To 0.096 g (0.5 mmol) of 4-methoxyphenylsulphonamide in 3 mL of DMF was added in one portion 0.020 g (0.50 mmol) of 60% sodium hydride and the reaction was stirre at 25° C. for 15 min. Then, 0.135 g (0.58 mmol) of methyl 3-bromo-2-fluorobenzylate was added to the solution in one portion and the resulting mixture was heated at 90° C. (bath temperature) for 18 h. The reaction was cooled to room temperature, acidified with 1N HCl and extracted with ethyl acetate. The combined organic layers were dried over magnesium sulfate, filtered and concentrated in vacuo. The residue was chromatographed on silica eluting with 30%–50% ethyl acetate/hexane to provide 0.037 g (19%) of the desired product. $^1HNMR(CDCl_3)$: 8 ppm (s, 1H, NH), 6.8–7.8 ppm (m, 7H, Ar), 3.9 ppm (s, 1H, OMe), 3.7 ppm (s, 1H, OMe).

EXAMPLE 199

3-Bromo-2-[benzyl-(4-methoxybenzenesulfonyl) amino]-benzoic acid methyl ester

To a solution of 0.413 g (1.03 mmol) of the product of Example 198 in 10 mL of DMF was added 0.062 g (1.55 mmol) of 60% sodium hydride. Stirring was continued for 15 min at 25° C. and 0.125 mL (1.442 mmol) of benzyl bromide was then added and the mixture was stird for 18 h at 55° C. The reaction was cooled to room temperature and the reaction mixture was poured into 200 mL water and 50 mL 1N HCl. The aqueous layer was then extracted with dichlromethane (100 mL) and ethyl acetate (100 mL). The combined organic layers were dried over magnesium sulfate, filtered and concentrated in vacuo. The residue was chromatographed on silica eluting with 10%–20% ethyl acetate/hexane to provide 0.390 g (77%) of the desired product. Electrospray Mass Spec 490.0 (M+H)

EXAMPLE 200

3-Bromo-2-[benzyl-(4-methoxybenzenesulfonyl) amino]-benzoic acid

In the same manner as described in Example 16, 0.390 g (0.80 mmol) of the product of Example 199 provided 0.180 g (84%) of the desired carboxylic acid as a white solid. $^1HNMR(CDCl_3)$: 9–10 ppm (br, 1H, COOH), 7–8 ppm (m, 12H, Ar), 4.5 ppm (m, 2H, —$CH_2$—), 3.9 ppm (s, 1H, OMe).

EXAMPLE 201

3-Bromo-2-[benzyl-(4-methoxybenzenesulfonyl) amino]-N-hydroxy-benzamide

In the same manner as described in Example 23, 0.177 g (0.372 mmol) of the product of Example 200 gave 0.155 g (85%) of the desired hydroxamic acid as a white solid. Electrospray Mass Spec: 491.0 (M+H).

EXAMPLE 202

5-Bromo-2-[(4-methoxy-benzenesulfonyl)-methyl-amino]-3-methyl-benzoic acid methyl ester In the same manner as described in Example 9, 27.0 g (65 mmol) of the product of Example 10 and 4.87 ml (78 mmol) of methyl iodide provided 22.06 g (86%) of the desired product as a white solid after trituration with ether. Electrospray Mass Spec 430 (M+H).

EXAMPLE 203

5-(2-tert-Butoxycarbonyl-vinyl)-2-[(4-methoxy-benzenesulfonyl)-methyl-amino]-3-methyl-benzoic acid methyl ester A mixture of 1.28 g (3.0 mmol) of the product of Example 202, 1.31 ml (9.0 mmol) of t-butylacrylate, 33.75 mg (0.15 mmol) of palladium diacetate, 1.0 g (3.15 mmol) of t-butyl ammonium bromide and 1.24 g (9.0 mmol) of $K_2CO_3$ in 10 ml of DMF was stifled at 85° C. for 6 h. The reaction mixture was poured into water and extracted with ethyl acetate. The combined organics were washed with water and brine, dried over $MgSO_4$, filtered and concentrated in vacuo. The resulting residue was dissolved in 20 ml of dichloromethane and stired with 1.0 g of celite and 1.0 g of silica gel for 20 min, filtered and concentnted in vacuo. The resulting residue was chromatographed on silica gel eluting with ETOAc/Hexane (1:5) to provide 1.26 g (88%) of the desired product as a white solid. Electrospray Mass Spec 476(M+H).

EXAMPLE 204

5-(2-Carboxy-vinyl)-2-[(4-methoxy-benzenesulfonyl)-methyl-amino]-3-methyl-benzoic acid methyl ester To a solution of 237.8 mg (0.5 mmol) of the product of Example 203 in 2 ml dichlocomethane, was added lml of trifluoroacetic acid and the reaction was stirre at room temperature for 2 h. The resulting mixture was concentrated in vacuo to provide 200 mg (95%) of the desired product as a white solid after trituration with hexane/ether (2:1). Electrospray Mass Spec 418(M–H).

EXAMPLE 205

2-[(4-Methoxy-benzenesulfonyl)-methyl-amino]-3-methyl-5-[2-(methyl-octyl-carbamoyl)-vinyl]-benzoic acid methyl ester A mixture of 182.6 mg (0.43 mmol) of the product of Example 204, 183 mg of molecular sieves and 105.8 mg (0.65 mmol) of 1,1'-dicyclohexylcarbodiimidazole in 4 ml THF was stirred for 1 h under nitrogen. A solution of N-methyloctylamine in 0.5 ml THF was then added to the reaction and the mixture was stirred for 18 hr at room temperature. The resulting mixture was filtered and the filtrate was diluted with ethyl acetate, washed with water and brine, dried over $MgSO_4$, filtered and concentrated in vacuo. The residue was chromatographed on silica gel eluting with EtOAc/Hexane (1:1) to provide 200 mg (84%) of the desired product as a colorless oil. Electrospray Mass Spec 545(M+H).

EXAMPLE 206

2-[(4-Methoxy-benzenesulfonyl)-methyl-amino]-3-methyl-5-[2-(methyl-octyl-carbamoyl)-vinyl]-benzoic acid In the same manner as described in Example 18, 188 mg (0.35 mmol) of the product of Example 205 provided 170 mg (93%) of the desired carboxylic acid as a white solid after trituration with Hexane/EtOAc (2:1). Electrospray Mass Spec 575(M+HCOOH—H).

EXAMPLE 207

N-Hydroxy-2-[(4-methoxy-benzenesulfonyl)-methyl-amino]-3-methyl-5-[2-(methyl-octyl-carbamoyl)-vinyl]-benzamide In the same manner as described in Example 23, 154 mg (0.29 mmol) of the product of Exauple 206 provided 45 mg (28%) of the desired hydroxamic acid as an off white solid. Electrospray Mass Spec 546(M+H).

EXAMPLE 208

5-(2-tert-Butoxycarbonyl-ethyl)-2-[(4-methoxy-benzenesulfonyl)-methyl-amino]-3-methyl-benzoic acid methyl ester A mixture of 340 mg (0.71 mmol) of the product of Example 203 and 35 mg of 10% palladium on carbon in 15 ml of ethanol was hydrogenated on a Parr shaker for 2 hr. The resulting mixture was filtered through Celite and Magnesol to provide 325 mg (95%) of the desired product as a colorless gum. Electrospray Mass Spec 478(M+H).

EXAMPLE 209

5-(2-Carboxy-ethyl)-2-[(4-methoxy-benzenesulfonyl)-methyl-amino]-3-methyl-benzoic acid methyl ester In the same manner as described in Example 204, 206 mg (0.43 mmol) of the product of Example 208 provides 181 mg (100%) the desired product as colorless gum. Electrospray Mass Spec 420(M–H).

EXAMPLE 210

2-[(4-Methoxy-benzenesulfonyl)-methyl-amino]-3-methyl-5-[2-(methyl-octyl-carbamoyl)-ethyl]-benzoic acid methyl ester In the same maimer as described in Example 205, 286 mg (0.68 mmol) of the product of Example 209 provides 362 mg (97%) of the desired product as a colorless gum. Electrospray Mass Spec 547(M+H).

EXAMPLE 211

2-[(4-Methoxy-benzenesulfonyl)-methyl-amino]-3-methyl-5-[2-(methyl-octyl-carbamoyl)-ethyl]-benzoic acid In the same manner as described in Example 18, 340 mg (0.62 mmol) of the product of Example 210 provided 304 mg (92%) of the desired carboxylic acid as a pale yellow crystalline solid. Electrospray Mass Spec 533(M+H).

EXAMPLE 212

N-Hydroxy-2-[(4-methoxy-benzenesulfonyl)-methyl-amino]-3-methyl-5-[2-(methyl-octyl-carbamoyl)-ethyl]-benzamide To a slurry of 300 mg (0.56 mmol) of the product of Example 211 and 106 mg (0.78 mmol) of 1-hydroxybenzotriazole in 5 ml DMF was added 183 mg (0.95 mmol) of 1-(3-dimethylaminopropyl)-3- ethylcarbodiimide hydrochloride and the reaction was stirred for 30 min at room temperature. Hydroxylamine hydrochloride (227 mg, 3.26 mmol) and 0.68 ml (4.89 mmol) of triethylamine and the reaction was sired for 18 hr. The resulting mixture was diluted with water and extracted with dichloromethane. The combined organics were washed with water and brine, dried over $MgSO_4$, filtered and concentrated in vacuo. The residue was chromatographed on silica gel with 2% $MeOH/CH_2Cl_2$ as the eluant to provide 190 mg (62%) of the desired hydroxamic acid as an off white solid. Electrospray Mass Spec 548(M+H).

EXAMPLE 213

5-(2-Dimethylcarbamoyl-vinyl)-2-[(4-methoxy-benzenesulfonyl)-methyl-amino]-3-methyl-benzoic acid methyl ester In the same manner as described in Example 203, 428.3 mg (1.0 mmol) of the roduct of Example 202 and 0.309 ml (3.0 mmol) of N,N-dimethylacrylamide provided 418 mg (93%) of the desired product as a colorless gum. Electrospray Mass Spec 447(M+H).

EXAMPLE 214

5-(2-Dimethylcarbamoyl-vinyl)-2-[(4-methoxy-benzenesulfonyl)-methyl-amino]-3-methyl-benzoic acid In the same manner as described in Example 18, 418 mg (0.94 mmol) of the product of Example 213 provided 303 mg (75%) of the desired carboxylic acid as a white solid. Electrospray Mass Spec 477 (M+HCOOH—H).

EXAMPLE 215

5-(2-Dimethylcarbamoyl-vinyl)-N-hydroxy-2-[(4-methoxy-benzenesulfonyl)-methyl-amino]-3-methyl-benzamide In te same manner as described in Example 212, 303 mg (0.70 mmol) of the product of Example 214 provided 268 mg (85%) of the desired hydroxamic acid as a white solid. Electrospray Mass Spec 448(M+H).

EXAMPLE 216

N-Ethyl-N-pyridin-4-ylmethyl-acrylamide

To a 0° C. solution of 0.835 ml (6.0 mmol) of 4-(ethylaminomethyl) pyridine and 1.05 ml (7.5 mmol) of triethylamine in 10 ml dichloomethane, was dropwise added 0.406 ml (5.0 mmol) of acryloyl chloride. The reaction mixture was warmed to room temperature and stilred for 18 hr. The resulting nmxture was washed with water and brne, dried over $MgSO_4$, filtered and concentrated in vacuo. The residue was chromatographed on silica gel with 3% MeOH/$CH_2Cl_2$ as the eluant to provide 651 mg (68%) of the desired product as a yellow gum. Electrospray Mass Spec 191(M+H).

EXAMPLE 217

5-[2-(Ethyl-pyridin-4-ylmethyl-carbamoyl)-vinyl]-2-[(4-methoxy-benzenesulfonyl)-methyl-amino]-3-methyl-benzioc acid methyl ester In the same manner as described in Example 203, 342.6 mg (0.80 mmol) of the product of Example 202 and 456.6 mg (2.4 mmol) of the product of Example 216 provided 405 mg (94%) of the desired product as a yellow gum. Electrospray Mass Spec 538(M+H).

EXAMPLE 218

5-[2-(Ethyl-pyridin-4-ylmethyl-carbamoyl)-vinyl]-2-[(4-methoxy-benzenesulfonyl)-methyl-amino]-3-methyl-benzoic acid To a solution of 405 mg (0.75 numol) of the product of Example 217 in 8 ml of THF:MeOH:$H_2O$ (2:1:1) was added 126.4 mg (3.01 mmol) of lithium hydroxide monohydrate. The reaction mixture was heated to reflux for 18 hr and then concentrated in vacuo. The residue was diluted with water, neutralized with 3N HCl and extracted with dichloromethane. The combined organics were washed with water and brine, dried over $MgSO_4$, filtered and concentrated in vacuo to provide 222 mg (56%) of the desired carboxylic acid as a beige solid. Electrospray Mass Spec 524(M+H).

EXAMPLE 219

5-[2-(Ethyl-pyridin-4-ylmethyl-carbamoyl)-vinyl]-N-hydroxy-2-[(4-methoxy-benzenesulfonyl)-methyl-amino]-3-methyl-benzamide In the same manner as described in Example 212, 214 mg (0.408 mmorl) of the product of Example 218 provided 156 mg (71%) of the desired hydroxamic acid, which was then dissolved in 2 ml of $CH_2Cl_2$ and Red with 0.32 ml (0.32 mmol) of 1M HCl/$Et_2O$. The resulting mixture was stirred for 1 hr at room tempure and concentrated in vacuo to provide 150 mg (64%) of the desired hydroxamic acid hydrochloride as a beige solid. Electrospray Mass Spec 539(M+H).

EXAMPLE 220

5-(2-tert-Butoxycarbonyl-vinyl)-2-[(4-methoxy-benzenesulfonyl)-pyridin-3-ylmethyl-amino]-3-methyl-benzoic acid methyl ester In the same manner as described in Example 203, 1.08 g (2.13 inmol) of the product of Example 89 provided 771 mg (65%) of the desired product as a brown oil. Electrospray Mass Spec 553(M+H).

EXAMPLE 221

5-(2-Carboxy-vinyl)-2-[(4-methoxy-benzenesulfonyl)-pyridin-3-ylmethyl-amino]-3-methyl-benzoic acid methyl ester In the same manner as described in Example 204, 750 mg (1.36 mmol) of the product of Example 220 provided 500 mg (60%) of the desired product. Electrospray Mass Spec 541(M+HCOOH—H)

EXAMPLE 222

2-[(4-Methoxy-benzenesulfonyl)-pyridin-3-ylmethyl-amino]-3-methyl-5-[2-(methyl-octyl-carbamoyl)-vinyl]-benzoic acid methyl ester In the manner as described in Example 205, 270 mg (0.54 mmol) of the product of Example 221 provided 162 mg (48%) of the desired product as a colorless gum. Electrospray Mass Spec 622(M+H).

EXAMPLE 223

2-[(4-Methoxy-benzenesulfonyl)-pyridin-3-ylmethyl-amino]-3-methyl-5-[2-(methyl-octyl-carbamoyl)-vinyl]-benzoic acid In the same manner as described in Example 218, 386 mg (0.62 mmol) of the product of Example 222 provided 274 mg (73%) of the desired carboxylic acid as a white crystalline solid. Electrospray Mass Spec 652(M+HCOOH—H).

EXAMPLE 224

N-Hydroxy-2-[(4-methoxy-benzenesulfonyl)-pyridin-3-ylmethyl-amino]-3-methyl-5-[2-(methyl-octyl-carbamoyl)-vinyl]-benzamide In the same manner as described in Example 219, 261 mg (0.43 mmol) of the product of Example 223 provided 211 mg (75%) of the desired product as a beige solid. Electrospray Mass Spec 623(M+H).

EXAMPLE 225

5-(2-Dimethylcarbamoyl-vinyl)-2-[(4-methoxy-benzenesulfonyl)-pyridin-3-ylmethyl-amino]-3-methyl-benzoic acid methyl ester In the same manner as described in Example 203, 550.4 mg (1.0 mmol) of the product of Example 89 and 297.4 mg (3.0 mmol) of N,N-dimethylacrylamide provided 419 mg (80%) of the desired product as a white solid. Electrospray Mass Spec 524(M+H).

EXAMPLE 226

5-(2-Dimethylcarbamoyl-vinyl)-2-[(4-methoxy-benzenesulfonyl)-pyridin-3-ylmethyl-amino]-3-methyl-benzoic acid In the same manner as described in Example 218, 404 mg (0.77 mmol) of the product of Example 225 provided 250 mg (64%) of the desired carboxylic acid as a pale yellow solid. Electrospray Mass Spec 508(M–H).

EXAMPLE 227

5-(2-Dimethylcarbamoyl-vinyl)-N-hydroxy-2-[(4-methoxy-benzenesulfonyl)-pyridin-3-ylmethyl-amino]-3-methyl-benzamide In the same manner as described in Example 219, 230 mg (0.45 mmol) of the product of Example 226 provided 54 mg (20%) of the desired product as a yellow solid. Electrospray Mass Spec 525(M+H).

EXAMPLE 228

5-[2-(Ethyl-phenyl-carbamoyl)-vinyl]-2-[(4-methoxy-benzenesulfonyl)-pyridin-3-ylmethyl-amino]-3-methyl-benzoic acid methyl ester In the same manner as described in Example 203, 550.4 mg (1.0 mmol) of the product of Example 89 and 425 mg (2.43 mniol) of N-ethylacryianilide provided 392 mg (65%) of the desired product as a brown solid. Electrospray Mass Spec 600(M+H).

EXAMPLE 229

5-[2-(Ethyl-phenyl-carbamoyl)-vinyl]-2-[(4-methoxy-benzenesulfonyl)-pyridin-3-ylmethyl-amino]-3-methyl-benzoic acid In the same manner as described in Example 218, 582 mg (0.97 mmol) of the product of Example 228 provided 404.7 mg (71%) of the desired carboxylic acid as a mustard solid. Electrospray Mass Spec 584(M–H).

EXAMPLE 230

5-[2-(Ethyl-phenyl-carbamoyl)-vinyl]-N-hydroxy-2-[(4-methoxy-benzenesulfonyl)-pyridin-3-ylmethyl-amino]-3-methyl-benzamide In the same manner as described in Example 219, 402 mg (0.69 mmol) of the product of Example 229 provided 190 mg (43%) of the desired product as a beige solid. Electrospray Mass Spec 601(M+H).

EXAMPLE 231

5-(2-Diallylcarbamoyl-vinyl)-2-[(4-methoxy-benzenesulfonyl)-pyridin-3-ylmethyl-amino]-3-methyl-benzoic acid methyl ester In the same manner as described in Example 203, 550.4 mg (1.0 mmol) of the product of Example 89 and 453.6 mg (3.0 mmol) of N,N-diallylacrylamide provided 309 mg (53%) of the desired product as a yellow gum. Electrospray Mass Spec 576(M+H).

EXAMPLE 232

5-(2-Diallylcarbamoyl-vinyl)-2-[(4-methoxy-benzenesulfonyl)-pyridin-3-ylmethyl-amino]-3-methyl-benzoic acid In a same manner as described in Example 218, 276 mg (0.48 mmol) of the product of Example 231 provided 149 mg (55%) of the desired carboxylic acid as a beige solid. Electrospray Mass Spec 562(M+H).

EXAMPLE 233

5-(2-Diallylcarbamoyl-vinyl)-N-hydroxy-2-[(4-methoxy-benzenesulfonyl)-pyridin-3-ylmethyl-amino]-3-methyl-benzamide In the same manner as described in Example 219, 188 mg (0.34 mmol) of the product of Example 232 provided 134 mg (65%) of the desired product as a brown solid Electrospray Mass Spec 577(M+H).

EXAMPLE 234

5-Bromo-2-(dimethylamino-methyleneamino)-3-methyl-benzoic acid tert-butyl ester

A mixture of 5.0 g (21.7 mmol) of the product of Example 132 and 20.8 ml (86.9 mmol) of N,N-dimethylformamide di-t-butylacetal in 30 ml of toluene was heated to reflux for 2 hr. The reaction mixture was cooled to room tenperature, washed with water and brine, dried over $MgSO_4$ and concentrated in vacuo to provide 3.61 g (49%) of the desired product as an yellow oil. Electrospray Mass Spec 341(M+H).

EXAMPLE 235

2-Amino-5-bromo-3-methyl-benzoic acid tert-butyl ester

A mixture of 3.52 g (10.3 mmole) of the product of Example 234 and 6.12 g (44.94 mmol) of zinc chloride in 50 ml of absolute ethanol was heated to reflux for 18 hr. The reaction mixture was concentrated in vacuo and the residue was diluted with $CH_2Cl_2$ and washed with water and brine, dried over $MgSO_4$, filtered and concentrated in vacuo to provide 2.48 g (84%) of the desired product as a pale brown liquid. Electrospray Mass Spec 286(M+H).

EXAMPLE 236

5-Bromo-2-(4-methoxy-benzenesulfonylamino)-3-methyl-benzoic acidtert-butyl ester In the same manner as described in Example 1, 2.48 g (8.66 mmol) of the product of Example 235 provided 3.41 g (86%) of the desired product as a pale yellow oil. Electrospray Mass Spec 402(M-t-bu-H).

EXAMPLE 237

5-Bromo-2-[(4-methoxy-benzenesulfonyl)-pyridin-3-ylmethyl-aminol]-3-methyl-benzoic acid tert-butyl ester In the same manner as described in Example 81, 3.15 g (6.9 mmol) of the product of Example 235 provided 2.6 g (69%) of the desired product as a white solid. Electrospray Mass Spec 547(M+H).

EXAMPLE 238

2-[(4-Methoxy-benzenesulfonyl)-pyridin-3-ylmethyl-amino]-3-methyl-5-(3-morpholin-4-yl-3-oxo-propenyl)-benzoic acid tert-butyl ester In the same manner as described in Example 203, 547.5 mg (1.0 mmol) of the product of Example 237 and 423 mg (3.0 mmol) of N-acryloylmorpholine provided 542 mg (89%) of the desired product as a pale yellow gum. Electrospray Mass Spec 608(M+H).

EXAMPLE 239

2-[(4-Methoxy-benzenesulfonyl)-pyridin-3-ylmethyl-amino]-3-methyl-5-(3-morpholin-4-yl-3-oxo-propenyl)-benzoic acid In the same manner as described in Example 204, 492 mg (0.809 mmol) of the product of Example 238 provided 464 mg (86%) of the desired product as a pale yellow solid. Electrospray Mass Spec 552(M+H).

EXAMPLE 240

N-Hydroxy-2-[(4-methoxy-benzenesulfonyl pyridin-3-ylmethyl-amino]-3-methyl-5-(3-morpholin-4-yl-3-oxo-propenyl)-benzamide In the same manner as described in Example 219, 150 mg (0.27 mmol) of the product of Example 239 provided 114 mg (25%) of the desired product as a cream solid. Electrospray Mass Spec 567(M+H).

EXAMPLE 241

2'-Formyl-4-[(4-methoxy-benzenesulfonyl)-pyridin-3-ylmethyl-amino]-5-methyl-biphenyl-3-carboxylic acid methyl ester To 5 ml of degassed ethylene glycol dirncthyl ether, was added 505.4 mg (1.0 mmol) of the product of Example 89, 165 mg (1.1 mmol) of 2-formylbenzene boronic acid, 58 mg (0.05 mmol) of tetrakis(triphenylphosphine)palladium and 1 ml (2.0 mmol) of 2M aqueous Na$_2$CO$_3$ and the mixture ws heated to reflux under nitrogen for 18 hr. The reaction was cooled to room temperature, diluted with ethyl acetate, washed with water and brine, dried over MgSO$_4$, filtered and concentrated in vacuo. The residue was chromatographed on silica gel with EtOAc/Hexane (1:1) as eluant to provide 499 mg (94%) of the desired product as an yellow solid. Electrospray Mass Spec 531 (M+H).

EXAMPLE 242

2'-Formyl-4-[(4-methoxy-benzenesulfonyl)-pyridin-3-ylmethyl-amino]-5-methyl-biphenyl-3-carboxylic acid In the same manner as described in Example 218, 478 mg (0.9 mmol) of the product of Example 241 provided 392 mg (84%) of the desired carboxylic acid as a pale yellow solid. Electrospray Mass Spec 515 (M–H).

EXAMPLE 243

2'-(Hydroxyimino-methyl)-4-[(4-methoxy-benzenesulfonyl)-pyridin-3-ylmethyl-amino]-5-methyl-biphenyl-3-carboxylic acid hydroxyamide In the same manner as described in Example 219, 380 mg (0.74 mmol) of the product of Example 242 provided 310 mg (53%) of the desired product as a cream solid. Electrospray Mass Spec 547 (M+H).

EXAMPLE 244

3'-Formyl-4-[(4-methoxy-benzenesulfonyl)-pyridin-3-ylmethyl-amino]-5-methyl-biphenyl-3-carboxylic acid methyl ester In the same manner as described in Example 241, 505.4 mg (1.0 mmol) of the product of Example 89 and 165 mg (1.1 mmol) of 3-formylbenzeneboronic acid provided 530 mg (100%) of the desired product as a pale yellow crystal. Electrospray Mass Spec 531 (M+H).

EXAMPLE 245

3'-Formyl-4-[(4-methoxy-benzenesulfonyl)-pyridin-3-ylmethyl-amino]-5-methyl-biphenyl-3-carboxylic acid In the same manner as described in Example 218, 500 mg (0.96 nmnol) of the product of Example 244 provided 214 mg (43%) of the desired carboxylic acid as a white solid. Electrospray Mass Spec 515 (M–H).

EXAMPLE 246

3'-(Hydroxyimino-methyl)-4-[(4-methoxy-benzenesulfonyl)-pyridin-3-ylmethyl-amino]-5-methyl-biphenyl-3-carboxylic acid hydroxyamide In the same manner as described in Example 219, 196 mg (0.38 mmol) of the product of example 245 provided 176 mg (80%) of the desired product as a cream solid. Electrospray Mass Spec 547 (M+H).

EXAMPLE 247

4'-Formyl-4-[(4-methoxy-benzenesulfonyl)-pyridin-3-ylmethyl-amino]-5-methyl-biphenyl-3-carboxylic acid methyl ester In the same manner as described in Example 241, 505.4 mg (1.0 mmol) of the product from Example 89 and 165 mg (1.1 mmol) of 4-formylbenzene boronic acid provided 519 mg (98%) of the desired product as a pale yellow solid. Electrospray Mass Spec 531 (M+H).

EXAMPLE 248

4'-Formyl-4-[(4-methoxy-benzenesulfonyl)-pyridin-3-ylmethyl-amino]-5-methyl-biphenyl-3-carboxylic acid In the same manner as described in Example 218, 486 mg (0.92 mmol) of the product of Example 247 provided 362 mg (76%) of the desired product as a white solid. Electrospray Mass Spec 515 (M–H).

EXAMPLE 249

4'-(Hydroxyimino-methyl)-4-[(4-methoxy-benzenesulfonyl)-pyridin-3-ylmethyl-amino]-5-methyl-biphenyl-3-carboxylic acid hydroxyamide In the same manner as described in Example 219, 320 mg (0.62 mmol) of the product of Example 248 provided 166 mg (49%) of the desired product as a cream solid. Electrospray Mass Spec 547 (M+H).

EXAMPLE 250

4-[(4-Methoxy-benzenesulfonyl)-pyridin-3-ylmethyl-amino]-5-methyl-2'-trifluoromethyl-biphenyl-3-carboxylic acid methyl ester In the same manner as described in Example 241, 505.4 mg (1.0 mmol) of the product of Example 89 and 244 mg (1.1 mmol) of 2-trifluoromethylbenzene boronic acid provided 559 mg (98%) of the desired product as a pale yellow gum. Electrospray Mass spec 571 (M+H).

EXAMPLE 251

4-[(4-Methoxy-benzenesulfonyl)-pyridin-3-ylmethyl-amino]-5-methyl-2'-trifluoromethyl-biphenyl-3-carboxylic acid In the same manner as desctibed in Example 218, 541 mg (0.95 mmol) of the product of Example 250 provided 475 mg (90%) of the desired carboxylic acid as a white solid. Electrospray Mass Spec 557 (M+H).

EXAMPLE 252

4-[(4-Methoxy-benzenesulfonyl)-pyridin-3-ylmethyl-amino]-5-methyl-2'-trifluoromethyl-biphenyl-3-carboxylic acid hydroxyamide In the same manner as described in Example 61, 447 mg (0.803 mmol) of the product of Example 251 provided the desired product, which was dissolved in 3 ml of dichlmethane and 3ml of methanol and treated with 0.76 ml (0.76rmol) of 1M HCl/Et$_2$O. The reacion mixture was stirred for 1 hr at room temperature and concentrated in vacuo to provide 373 mg (76%) of the desired product. as a beige solid. Electrospray Mass Spec 572 (M+H).

EXAMPLE 253

5-Furan-2-yl-2-[(4-methoxy-benzenesulfonyl)-pyridin-3-ylmethyl-amino]-3-methyl-benzoic acid methyl ester In the same manner as described in Exanple 241, 505.4 mg (1.0 mmol) of the product of Exaaaple 89 and 123 mg (1.1 mmol) of furan-2-boronic acid provided 432 mg (88%) of the desired product as a pale yellow solid. Electrospray Mass Spec 493 (M+H).

EXAMPLE 254

5-Furan-2-yl-2-[(4-metboxy-benzenesulfonyl)-pyridin-3-ylmethyl-amino]-3-methyl-benzoic acid In the same manner as described in Example 218, 419 mg (0.85 mmol) of the product of Example 253 provided 227 mg (47%) of the desired carboxylic acid as a white solid after trituration with ether. Electrospray Mass Spec 477 (M–H).

EXAMPLE 255

5-Furan-2-yl-N-hydroxy-2-[(4-methoxy-benzenesulfonyl)-pyridin-3-ylmethyl-amino]-3-methyl-benzamide In the same manner as described in Example 219, 220 mg (0.46 mmol) of the product of Example 254 provided 185 mg (76%) of the desired product as a cream solid. Electrospray Mass Spec 494 (M+H).

EXAMPLE 256

5-(3-Formyl-thiophen-2-yl)-2-[(4-methoxy-benzenesulfonyl)-pyridin-3-ylmethyl-amino]-3-methyl-benzoic acid methyl ester In the same manner as described in Example 241, 505.4 mg (1.0 mmol) of the product of Example 89 and 343.2 mg (2.2 mmol) of 3-formylthiophene-2-boronic acid provided 379 mg (71%) of the desired product as a pale yellow solid. Electrospray Mass Spec 537 (M+H).

EXAMPLE 257

5-(3-Formyl-thiophen-2-yl)-2-[(4-methoxy-benzenesulfonyl)-pyridin-3-ylmethyl-amino]-3-methyl-benzoic acid In the same manner as described in Example 218, 364 mg (0.68 mmol) of the product of Example 256 provided 229 mg (65%) of the desired carboxylic acid as a pale yellow solid. Electrospray Mass Spec 521 (M–H).

EXAMPLE 258

N-Hydroxy-5-[3-(hydroxyimino-methyl)-thiophen-2-yl]-2-[(4-methoxy-benzenesulfonyl)-pyridin-3-ylmethyl-amino]-3-methyl-benzamide In the same manner as described in Example 219, 220 mg (0.42 mmol) of the product of Example 257 provided 168 mg (68%) of the desired product as a cream solid. Electrospray Mass Spec 553 (M+H).

EXAMPLE 259

5-(5-Chloro-thiophen-2-yl)-2-[(4-methoxy-benzenesulfonyl)-pyridin-3-ylmethyl-amino]-3-methyl-benzoic acid methyl ester In the same manner as described in Example 241, 505 mg (1.0 mmol) of the product of Example 89 and 357 mg (2.2 mmol) of 5-chlorothiophene-2-boronic acid provided 332 mg (61%) of the desired product as an yellow solid. Electrospray Mass Spec 543 (M+H).

EXAMPLE 260

5-(5-Chloro-thiophen-2-yl)-2-[(4-methoxy-benzenesulfonyl)-pyridin-3-ylmethyl-amino]-3-methyl-benzoic acid In the same manner as described in Example 218, 312 mg (0.58 mmol) of the product of Example 259 provided 277 mg (91%) of the desired carboxylic acid as a pale yellow solid. Electrospray Mass Spec 527 (M–H).

EXAMPLE 261

5-(5-Chloro-thiophen-2-yl)-N-hydroxy-2-[(4-methoxy-benzenesulfonyl)-pyridin-3-ylmethyl-amino]-3-methyl-benzamide In the same manner as described in Example 219, 277 mg (0.524 mmol) of the product of Example 260 provided 135 mg (44%) of the desired product as a pale yellow solid. Electrospray Mass Spec 544 (M+H).

EXAMPLE 262

5-(5-Acetyl-thiophen-2-yl)-2-[(4-methoxy-benzenesulfonyl)-pyridin-3-ylmethyl-amino]-3-methyl-benzoic acid methyl ester In the same manner as described in Example 241, 505.4 mg (1.0 mmol) of the product of Example 89 and 374 mg (2.2 mmol) of 5-acetylthiophene-2-boronic acid provided 525 mg (95%) of the desired product as a cream colored solid. Electrospray Mass Spec 551 (M+H).

EXAMPLE 263

5-(5-Acetyl-thiophen-2-yl)-2-[(4-methoxy-benzenesulfonyl)-pyridin-3-ylmethyl-amino]-3-methyl-benzoic acid In the same manner as described in Example 218, 500 mg (0.9 mmol) of the product of Example 262 provided 390 mg (81%) of the desired carboxylic acid as a pale yellow solid. Electrospray Mass Spec 535 (M–H).

EXAMPLE 264

5-(5-Acetyl-thiophen-2-yl)-N-hydroxy-2-[(4-methoxy-benzenesulfonyl)-pyridin-3-ylmethyl-amino]-3-methyl-benzamide In the same manner as described in Example 219, 400 mg (0.75 mmol) of the product of Example 263 provided 226 mg (52%) of the desired product as a white solid. Electrospray Mass Spec 552 (M+H).

EXAMPLE 265

2-[Benzyl-(4-metboxy-benzenesulfonyl)-amino]-3-methyl-5-vinyl-benzoic acid methyl ester In the same manner as described in Example 139, 728 mg (1.44 mmol) of the product of Example 11 and 0.552 ml (2.0 mmol) of vinyltributyltin provided 430 mg (66%) of the desired product as a white solid. Electrospray Mass Spec 452 (M+H).

EXAMPLE 266

2-[Benzyl-(4-methoxy-benzenesulfonyl)-amino]-3-methyl-5-vinyl-benzoic acid

In the same manner as described in Example 18, 160 mg (0.35 mmol) of the product of Example 265 provided 133 mg (85%) of the desired carboxylic acid as a white solid. Electrospray Mass Spec 436 (M–H).

EXAMPLE 267

2-[Benzyl-(4-methoxy-benzenesulfonyl)-amino]-N-hydroxy-3-methyl-5-vinyl-benzamide In the same manner as described in Example 23, 120 mg (0.27 mmol) of the product of Example 266 provided 63.4 mg (51%) of the desired hydroxamic acid as a white solid. Electrospray Mass Spec 453 (M+H).

EXAMPLE 268

2-[Benzyl-(4-methoxy-benzenesulfonyl)-amino]-5-formyl-3-methyl-benzoic acid methyl ester To a solution of 2.21 g (4.89mmole) of the product of Example 265 in 20 ml of dioxane:H2O (3:1) was added 0.3 ml of a 2.5 weight % solution of osmium tetroxide in tbutanol and the reaction was stirred until the solution turned dark brown. Then 2.09 g (9.78 mmol) of sodium periodate was added portionwise over a period of 20 min. The resulting mixture was stirred for 1.5 hr, diluted with ether, washed with water and brine, dried over $MgSO_4$, filtered and concentrated in vacuo to provide 1.73 g (78%) of the desired product as a white solid after trituration with ether. Electrospray Mass Spec 454 (M+H).

EXAMPLE 269

4-[Benzyl-(4-methoxy-benzenesulfonyl)-amino]-5-methyl-isophthalic acid 3-methyl ester To a solution of 317 mg (0.7 mmol) of the product of Example 268 and 102 mg (1.05 mmol) of sulfamic acid in 40 ml of water:THF (3:1) was added 98 mg (1.08 mmol) of sodium chlorite. The resulting mixture stirred for 2 hr, diluted with ether, washed with water and brine, dried over $MgSO_4$, filtered and concentrated in vacuo to provide 325 mg (99%) of the desired carboxylic acid as a white solid. Electrospray Mass Spec 468 (M–H).

EXAMPLE 270

4-[Benzyl-(4-methoxy-benzenesulfonyl)-amino]-5-methyl-isophthalic acid

In the same manner as described in Example 18, 325 mg (0.7 mmol) of the product of exanmple 169 provided 224.3 mg (70%) of the desired product as a white solid. Electrospray Mass Spec 454 (M–H).

EXAMPLE 271

4-[Benzyl-(4-methoxy-benzenesulfonyl)-amino]-N(1),N(3)-dihydroxy-5-methyl-isophthalamide In the same manner as described in Example 23, 210 mg (0.46 mmol) of the product of Example 270 provided 160 mg (72%) of the desired product as a cream solid. Electrospray Mass Spec 486 (M+H).

EXAMPLE 272

4-[Benzyl-(4-methoxy-benzenesulfonyl)-amino]-N(1),N(3)-dihydroxy-5-methyl-isophthalamide di-sodium salt To a solution of 100 mg (0.206 mmol) of the product of Example 271 in 2 ml of methanol was added 0.412 ml (0.412 mmol) of 1N NaOH andthe reaction was stirred at room temperature for 2 hr. The reaction mixture was concentrated in vacuo, and the residue was triturated with ether to provide 109 mg (100%) of the desired product as a pale yellow solid Electrospray Mass Spec 486 (M+H).

EXAMPLE 273

2-(4-Methoxy-benzenesulfonylamino)-3-methyl-5-vinyl-benzoic acid methyl ester

In the same manner as described in Example 139, 700 mg (1.69 mmol) of the product of Example 10 and 0.73 ml (2.5 mmol) of vinyltributyltin provided 500 mg (82%) of the desired product as a white solid. Electrospray Mass Spec 362 (M+H).

EXAMPLE 274

5-Ethyl-2-(4-methoxy-benzenesulfonylamino)-3-methyl-benzoic acid methyl ester

In the same manner as described in Example 208, 479 mg (1.33 mmol) of the product of Example 273 provided 480 mg (100%) of the desired product as a white solid. Electrospray Mass Spec 364 (M+H).

EXAMPLE 275

5-Ethyl-2-[(4-methoxy-benzenesulfonyl)-pyridin-3-ylmethyl-amino]-3-methyl-benzoic acid methyl ester In the same manner as described in Example 81, 455 mg (1.25 mmol) of the product of Example 274 provided 544 mg (96%) of the desired product as a pale yellow oil. Electrospray Mass Spec 455 (M+H).

EXAMPLE 276

5-Ethyl-2-[(4-methoxy-benzenesulfonyl)-pyridin-3-ylmethyl-amino]-3-methyl-benzoic acid In the same manner as described in Example 218, 496 mg (1.09 mmol) of the product of Example 275 provided 345 mg (72%) of the desired carboxylic acid as a beige solid. Electrospray Mass Spec 441 (M+H).

EXAMPLE 277

5-Ethyl-N-hydroxy-2-[(4-methoxy-benzenesulfonyl)-pyridin-3-ylmethyl-amino]-3-methyl-benzamide In the same manner as described in Example 23, 320 mg (0.73 mmol) of the product of Exanple 276 provided 166 mg (50%) of the desired hydroxamic acid. The hydroxamic acid was then dissolved in 4 ml of dichloromethane and 0.1 ml of methanol and 0.4 ml (0.4 mmol) of 1M HCl/ether was added. The reaction mixture was stirred for 1 hr and concentrated in vacuo. The residue was triturated with ether to provide 177 mg (98%) of the desired product as a cream solid. Electrospray Mass Spec 456 (M+H).

EXAMPLE 278

2-[Benzyl-(4-methoxy-benzenesulfonyl)-amino]-5-hydroxymethyl-3-methyl-benzoicacid methyl ester To a mixture of 907 mg (2.0 mmol) of the product of Example 268 in 50 ml of MeOH:THF (4:1) was added sodium borohydride. The reaction was then stilred at room temperature for 30 min and concentrated in vacuo. The residue was dissolved in dichloromethane, washed with 5% HCl and brine, dried over $MgSO_4$, filtered and concentrated in vacuo to provide 872 mg (96%) of the desired product as a white crystalline solid. Electrospray Mass Spec 456 (M+H).

EXAMPLE 279

2-[Benzyl-(4-methoxy-benzenesulfonyl)-amino]-5-bromomethyl-3-methyl-benzoic acid methyl ester To a 0° C. solution of 1.08 g (2.37 mmol) of the product of Example 278 and 983 mg (2.96 mmol) of carbon tetrabromide in 24 ml of dichloromethane was added 933 mg (3.55 mmol) of triphenyl phosphine. The resulting mixture was stirred for 15 min and then concentrated in vacu. The residue was chromatographed on silica gel using EtOAc:Hexane (1:6) as eluant to provide 1.1 g (96%) of the desired product as a white crystalline solid. Electrospray Mass Spec 520 (M+H).

EXAMPLE 280

2-[Benzyl-(4-methoxy-benzenesulfonyl)-amino]-5-diethylaminomethyl-3methyl-benzoic acid methyl ester A solution of 518.4 mg (1.0 mmole) of the product of Example 279, 0.5 ml (4.8 mmol) of diethylamine and 0.172 ml (2.0 mmol) of pyridine in 10 ml of dichloromethane was stired at room temperature for 18 hr. The resulting mixture washed with water and brine, dried over $MgSO_4$, filtered and concentrated in vacuo. The residue was chromatographed on silica gel with 2% $MeOH/CH_2Cl_2$ as eluant to provide 425 mg (83%). Electrospray Mass Spec 511 (M+H).

EXAMPLE 281

2-[Benzyl-(4-methoxy-benzenesulfonyl)-amino]-5-diethylaminomethyl-3-methyl-benzoic acid In the same manner as described in Example 218, 400 mg (0.78 mmol) of the product of Example 280 provided 324 mg (85%) of the desired carboxylic acid as a white solid. Electrospray Mass Spec 497 (M+H).

EXAMPLE 282

2-[Benzyl-(4-methoxy-benzenesulfonyl)-amino]-5-diethylaminomethyl-N-hydroxy-3-methyl-benzamide In the same manner as described in Example 219, 324 mg (0.65 mmol) of the product of example 281 provided 162 mg (45% 0 of the desired product as a beige solid. Electrospray Mass Spec 512 (M+H).

EXAMPLE 283

2-[(4-Methoxy-benzenesulfonyl)-pyridin-3-ylmethyl-amino]-3-methyl-5-pyridin-3-yl-benzoic acid methyl ester In the same manner as described in Example 139, 505 mg (1.0 mmol) of the product of Example 89 and 515 mg (1.4 mmol) of 3-(tributylstannyl)pyridine provided 437 mg (87%) of the desired product as a pale yellow solid. Electrospray Mass Spec 504 (M+H).

EXAMPLE 284

2-[(4-Methoxy-benzenesulfonyl)-pyridin-3-ylmethyl-amino]-3-methyl-5-pyridin-3-yl-benzoic acid In the smae manner as described in Example 218, 422 mg (0.84 mmol) of the product of Example 283 provided 410 mg (100%) of the desired carboxylic acid as a cream solid. Electrospray Mass Spec 490 (M+H).

EXAMPLE 285

N-Hydroxy-2-[(4-methoxy-benzenesulfonyl)-pyridin-3-ylmethyl-amino]-3-methyl-5-pyridin-3-yl-benzamide In the same manner as described in Example 219, 420 ng (0.85 mmol) of the product of Example 284 provided 160 mg (33%) of the desired product as a pinkish solid. Electrospray Mass Spec 505(M+H).

EXAMPLE 286

2-Amino-3,6-dimethyl-benzoic acid benzyl ester

A mixture of 940 mg (5.73 mmol) of 2-amino-3,6-dimethylbenzoic acid, 0.750 ml (6.3 mmol) of benzyl bromide, 1.04 g (7.5mmole) of potassium carbonate and 40 mg (0.27mmole) of soium iodide in 20 ml of acetone was heated to reflux for 20 hr. The resulting mixture was then concentrated in vacuo and the residue was chromatoghed with EtOAc/Hexane (1:50) as eluant to provide 697 mg (48%) of the desired product as a yellow oil. Electrospray Mass Spec 256 (M+H).

EXAMPLE 287

2-(4-Methoxy-benzenesulfonylamino)-3,6-dimethyl-benzoic acidbenzyl ester

In the same manner as described in Example 1,971 mg (3.8 mmol) of the product of Example 286 provided 1.415 g (87%) of the desired product as a cream solid after trituration with Ether/Hexane(1:1). Electrospray Mass Spec 426 (M+H).

EXAMPLE 288

2-[Benzyl-(4-methoxy-benzenesulfonyl)-amino]-3,6-dimethyl-benzoic acid benzyl ester In the same manner as described in Example 9, 321 mg (0.754 mmol) of the product of Example 287 provided 356 mg (92%) of the desired product as a white solid after trituration with hexane. Electrospray Mass Spec 516 (M+H).

EXAMPLE 289

N-Benzyl-N-(2-hydroxymethyl-3,6-dimethyl-phenyl)-4-methoxy-benzenesulfonamide

To a slurry of 21 lmg (5.04 mmol) of lithium aluminum hydride in 6 ml of dry THF under nitrogen, was added dropwise a solution of 649 mg (1.26 mmol) of the product of Example 288 in 6 ml of dry THF. The reaction mixture was stirred for 3 hr and then sodium sulfate pentahydrate was slowly added until sizzling stopped and thick solid formed. The solid was filtered and the filtrate was concentrated in vacuo to provide 454 mg (87%) of the desired product as a white solid after trituration with hexane. Electrospray Mass Spec 412 (M+H).

EXAMPLE 290

N-Benzyl-N-(2-formyl-3,6-dimethyl-phenyl)-4-methoxy-benzenesulfonamide

To a solution of 438.7 mg of the product of Example 289 in 20 ml of acetone was added 5.33 ml (10.07 mmol) of Jones reagent and the reaction was stirred at room temperature for 18 hr. The resulting mixture was concentrated in vacuo and the residue was diluted with dichloromethane, washed with water and brine, dried over MgSO$_4$, filtered and concnentrated in vacuo. The residue was triturated with hexane to provide 396 mg (91%) of the desired product as a white solid. Electrospray Mass Spec 410 (M+H).

EXAMPLE 291

2-[Benzyl-(4-methoxy-benzenesulfonyl)-amino]-3,6-dimethyl-benzoic acid

In the same manner as described in Example 269, 378 mg (0.92 mmol) of the product of Example 290 provided 260 mg (66%) of the desired carboxylic acid as a white solid. Electrospray Mass Spec 426 (M+H).

EXAMPLE 292

2-[Benzyl-(4-methoxy-benzenesulfonyl)-amino]-N-hydroxy-3,6-dimethyl-benzamide

In the same manner as described in Example 23, 255 mg (0.6 mmol) of the product of Example 291 provided 206 mg (78%) of the desired product as a white solid. Electrospray Mass Spec 441 (M+H).

EXAMPLE 293

2-[(4-Methoxy-benzenesulfonyl)-pyridin-3-ylmethyl-amino]-3,6-dimethyl-benzoic acid benzyl ester In the same manner as described in Example 81, 1.415 g (3.33 mmol) of the product of example 287 provided 1.02 mg (59%) of the desired product as a white solid after trituration with ether. Electrospray Mass Spec 517 (M+H).

EXAMPLE 294

N-(2-Hydroxymethyl-3,6-dimethyl-phenyl)-4-methoxy-N-pyridin-3-ylmethyl-benzenesulfonamide In the same manner as described in Example 289, 993 mg (1.92 mmol) of the product of Example 293 provided 633 mg (80%) of the desired product as a yellow oil. Electrospray Mass Spec 413 (M+H).

EXAMPLE 295

N-(2-Formyl-3,6-dimethyl-phenyl)-4-methoxy-N-pyridin-3-ylmethyl-benzenesulfonamide In the same manner as described in Example 290, 633 mg (1.54 mmol) of the product of Example 294 provided 438 mg (787%) of the desired product as a yellow solid. Electrospray Mass Spec 411 (M+H).

EXAMPLE 296

2-[(4-Methoxy-benzenesulfonyl)-pyridin-3-ylmethyl-amino]-3,6-dimethyl-benzoic acid In the same manner as described in Example 269, 438 mg (1.07 mmol) of the product of Example 295 provided 345 mg (76%) of the desired carboxylic acid as an off white solid. Electrospray Mass Spec 425 (M−H).

EXAMPLE 297

N-Hydroxy-2-[(4-methoxy-benzenesulfonyl)-pyridin-3-ylmethyl-amino]-3,6-dimethyl-benzamide In the same manner as described in Example 252, 130 mg (0.31 mmol) of the product of Example 296 provided 100 mg (74%) of the desired hydroxamic acid. A sample of 235 mg (0.53 nmol) of this product provided 229 mg (90%) of the desired hydroxamic acid hydrochloride as a cream colored solid after trituration with ether. Electrospray Mass is Spec 442 (M+H).

EXAMPLE 298

2-(4-Methoxy-benzenesulfonylamino)-3-methyl-5-[3-(5-methyl-furan-2-yl)-isoxazol-5-yl]-benzo acid methyl ester To a solution of 146.6 mg (1.1 mmol) of N-chlorosuccinimide and 0.006 ml of pyridine in 3.0 ml of chloroform under nitrogen was added 348.2 mg (1.09 mmol) of 5-methyl-fiuran-2-caboxaldehyde oxime at room temperature. The reaction mixture was stirred for 30 min and 392 mg (1.09 mmol) of 5-ethynyl-2-(4-methoxybenzene-sulfonylamino)-3-methyl-benzoic acid methyl ester was added in one portion followed by the dropwise addition of 0.16 ml (1.15 mmol) of triethylamine over a period of 1 hr. The resulting mixture was stirred at room temperature for 18 hr, diluted with dichloromethane, washed with water and brine, dried over $MgSO_4$, filtered and concentrated in vacuo. The residue was chromatographed on silica gel with EtOAc/Hexane (1:9) as eluant to provide 313 mg (60%) of the desired product. as a white solid. Electrospray Mass Spec 483 (M+H).

EXAMPLE 299

2-[(4-Methoxy-benzenesulfonyl)-pyridin-3-ylmethyl-amino]-3-methyl-5-[3-(5-methyl-furan-2-yl)-isoxazol-5-yl]-benxoic acid methyl ester In the same manner as described in Example 81, 305 mg (6.3 mmol) of the product of Example 298 provided 240 mg (66%) of the desired product as a colorless gum. Electrospray Mass Spec 574 (M+H).

EXAMPLE 300

2-[(4-Methoxy-benzenesulfonyl)-pyridin-3-ylmethyl-amino]-3-methyl-5-[3-(5-methyl-furan-2-yl)-isoxazol-5-yl]-benzoic acid In the same manner as described in Example 218, 234 mg (0.408 mmol) of the product of Example 299 provided 149 mg (65%) of the desired carboxylic acid as a pale yellow solid. Electrospray Mass Spec 560 (M+H).

EXAMPLE 301

N-Hydroxy-2-[(4-methoxy-benzenesulfonyl)-pyridin-3-ylmethyl-amino]-3-methyl-5-[3-(5-methyl-furan-2-yl)-isoxazol-5-yl-benzamide In the same manner as described in Example 219, 141 mg (0.25 mmol) of the product of Example 300 provided 30 mg (19%) of the desired product as a brownish solid. Electrospray Mass Spec 575 (M+H).

EXAMPLE 302

2-[Benzyl-(4-ethoxy-benzenesulfonyl)-amino]-N-hydroxy-3,5-dimethyl-benzamide

The product of Example 65 (2.0 g, 4.68 mmol) is reacted with ethyl alcohol according to the procedure of Example 73 to give 0.461 g (21%) of the p-ethoxybenzene sulfonamide-ester.

The sulfonaride-ester (0.440 g, 0.941 mmol) is hydrolyzed according to the procedure of Example 18 to give 0.318 g (77%) of the carboxylic acid.

The carboxylic acid (0.290 g, 0.650 mmol) is converted into its acid chlorde followed by reaction with hydroxylamine according to the procedure of Example 23 to give 0.092 g (31%) of the hydroxamate. Electrospray Mass Spec: 455.3 (M+H)+.

EXAMPLE 303

2-[Benzyl-(4-propoxy-benzenesulfonyl)-amino]-N-hydroxy-3,5-dimethyl-benzamide

The product of Exanple 65 (1.0 g, 2.339 mmol) is reacted with n-propanol accoding to the procedure of Example 73 to give 0.456 g (46%) of the para-n-propoxybenzene sulfonamide-ester.

The sulfonamideester (0.486 g, 0.980 mmol) is hydrolyzed according to the procedure of Example 18 to give 0.217 g (49%) of the carboxylic acid.

The carboxylic acid (0.190 g, 0.419 mmol) is converted into its acid chloride followed by reaction with hydroxylamine according to the procedure of Example 23 to give 0.104 g (53%) of the hydroxamate. Electrospray Mass Spec: 469.0 (M+H)+.

EXAMPLE 304

2-[Benzyl-(4-isopropoxy-benzenesulfonyl)-amino]-N-hydroxy-3,5-dimethyl-benzamide The product of Example 65 (2.0 g, 4.68 mmol) is reacted with isopropanol according to the procedure of Example 73 to give 0.706 g (30%) of the para-n-propoxybenzene sulfonamide-ester.

The sulfonamide-ester (0.400 g, 0.827 mmol) is hydrolyzed according to the procedure of Example 18 to give 0.180 g (48%) of the carboxylic acid.

The carboxylic acid (0.113 g, 0.331 mmol) is converted into its acid chloride followed by reaction with hydroxylamine according to the procedure of Example 23 to give 0.056 g (36%) of the hydroxamate. Electrospray Mass Spec: 468.9 (M+H)+.

EXAMPLE 305

5-Bromo-2-(4-fluoro-benzenesulfonylamino)-3-methyl-benzoic acid

By following the procedure of Example 134 the product of Example 133 and 4-flurobenzenesulfonyl chloride provides 5-bromo-2-(4-fluoro-benzenesulfonylamino)-3methyl-benzoic acid as a yellow solid in 36% yield. Electrospray Mass Spec: 386.0 (M–H)–

EXAMPLE 306

Benzyl-(4-fluoro-benzenesulfonyl)-amino]-5-bromo-3-methyl-benzoic acid benzyl ester To a solution of 0.25 g (0.687 mmol) of the product of Example 305 in 5.0 mL of DMF was added 0.23 mL (1.923 mmol) of benzyl bromide and 0.06 g (1.511 mmol) of 60% sodium hydride. The reaction mixture was stirred for 18 h at room temperure and then diluted with ether, washed with water, dried over $MgSO_4$, filtered and concentreted in vacuo. The resulting residue was chromatographed on silica gel eluting with EtOAc/Hxanes (1:10) to provide 0.324 g (82%) of the product as a colorless oil. Electrospray Mass Spec: 568.1 (M+H)+.

EXAMPLE 307

2-[Benzyl-(4-benzyloxy-benzenesulfonyl)-amino]-5-bromo-3-methyl-benzoic acid

By following the procedure of Example 73, 0.284 g (0.493 mmol) of the product of Example 306 gives 0.185 g (66%) of the desired product as a white solid. Electrospray Mass Spec: 565.9 (M–H)–.

EXAMPLE 308

2-[Benzyl-(4-benzyloxy-benzenesulfonyl)-amino]-5-bromo-N-hydroxy-3-methyl-benzamide By following the procedure of Example 23, 0.168 g (0.297 mmol) of the product of Example 307 gives 0.131 g (76%) of the desired product as a white solid. Electrospray Mass Spec: 581.0 (M+H)+.

EXAMPLE 309

N-Hydroxy-2-[(4-methoxy-benzenesulfonyl)-methyl-amino]-3-morpholin-4-ylmethyl-benzamide Following the procedure of Example 189, the product of Example 188 (0.50 g, 1.168 mmol) and morpholine gives 0.325 g (64%) of the benzylic amine-ester.

Following the procedure of Example 190, 0.291 g (0.670 mmol) of the ester is then hydrolyzed to give 0.286 g (100%) of the carboxylic acid.

Following the procedure of Example 23, 0.229 g (0.536 mmol) of the carboxylic acid gives 0.186 g of the hydroxamic acid as a white solid. The hydroxamate is dissolved in 4 mL of dichloromeane and 0.2 mL of methanol and 0.85 mL of 1.0M HCl in ether is added. The reaction is stieed at room temperature for 1 h, diluted with ether and the resulting solid is collected by filtration and dried in vacuo to give 0.139 g of the hydroxamate-amine salt as a white solid. Electmspray Mass Spec: 435.9 (M+H)+.

EXAMPLE 310

N-Hydroxy-2-[(4-methoxy-benzenesulfonyl)-methyl-amino]-3-pyrrolidin-1-ylmethyl-benzamide Following the procedure of Example 189, the product of Example 188 (0.50 g, 1.168 mmol) and pyrrolidine gives 0.327 g (69%) of the benzylic amine-ester.

Following the procedure of Example 190, 0.307 g (0.734 mmol) of the ester is then hydrolyzed to give 0.302 g (100%) of the carboxylic acid.

Following the procedure of Example 309, 0.251 g (0.610 mmol) of the carboxylic acid gives 0.127 g of the hydroxamic acid-amine salt as a white solid. Electrospray Mass Spec: 419.9 (M+H)+.

EXAMPLE 311

N-Hydroxy-3-imidazol-1-ylmethyl-2-[(4-methoxy-benzenesulfonyl)-methyl-amino]-benzamide Following the procedure of Example 189, the product of Example 188 (0.75 g, 1.752 mmol) and imidazole gives 0.441 g (61%) of the benzylic amine-ester.

Following the procedure of Example 190, 0.435 g (1.048 mmol) of the ester is then hydrolyzed to give 0.308 g (72%) of the carboxylic acid.

Following the procedure of Example 309, 0.261 g (0.640 mmol) of the carboxylic acid gives 0.154 g of the hydroxamic acid-amine salt as a white solid. Electrospray Mass Spec: 416.9 (M+H)+.

EXAMPLE 312

5-Bromo-2-[(4-methoxy-benzenesulfonyl)-methyl-amino]-3-(4-methyl-piperazin-1-ylmethyl)-benzoic acid methyl ester To a solution of 3.0 g (7.01 mmol) of the product of Example 202 in 170 mL of carbon tetrachloride was added 1.56 g (8.76 mmmol) of N-bromosuccinimide and the mixture was heated to reflux while irradiated by a sunlamp for 3 h. The resulting mixture was cooled, washed with water, dried over MgSO$_4$, filtered and concentrated in vacuo.

To a solution of 0.477 g (0.941 mmol) of the resulting benzylic bromide in 5.0 mL of DMF was added 0.115 mL (1.035 nmiol) of N-methylpiperazine and 0.389 g (2.822 mmol) of potassium carbonate. The reaction mixture was then stirred overnight at room temperature and then diluted with ether, washed with water, dried over Na$_2$SO$_4$, filtered and concentrated in vacuo. The resulting residue was chromatographed on silica gel eluting with chloroform/methanol (9:1) to provide 0.29 g (59%) of the product as a brown oil. Electospray Mass Spec: 526.1 (M+H)+.

EXAMPLE 313

5-B romo-N-hydroxy-2-[(4-methoxy-benzenesulfonyl)-methyl-amino]-3-(4-methyl-piperazin-1-ylmethyl)-benza Following the prcedure of Example 190, 0.25 g (0.475 mmol) of the product of Example 312 gives 0.475 g (100%) of the desired carboxylate salt as a white solid.

Following the procedure of Example 309 the caiboxylate is converted into the corresponding hydroxamic acid-amine salt, isolated as a white solid. Electrospray Mass Spec: 527.1 (M+H)+.

EXAMPLE 314

5-Bromo-N-hydroxy-2-[(4-methoxy-benzenesulfonyl)-methylamino]-3-pyrrolidin-1-ylmethyl-benzamide Following the procedure of Example 312, the product of Example 202 and pyrrodine gives the benzylic amine-ester.

Following the procedure of Example 190 the ester is hydrolyzed to the corresponding carboxylate.

Following the procedure of Example 309 the carboxylate is converted into the corresponding hydroxamic acid-amine salt, isolated as a tan solid. Electrospray Mass Spec: 498.0 (M+H)+.

EXAMPLE 315

2-[(4-Methoxy-benzenesulfonyl)-(tert-butoxycarbonyl)-amino]-3-methyl-benzoic acid methyl ester To a solution of 2.5 g (7.463 mmol) of the product of Example 3 in 10 mL of DMF and 6.0 mL of pyridine was added 1.95 g (8.955 mmol) of di-t-butyl dicarbonate and 0.228 g (1.866 mmol) of 4-dimethylaminopyridine. The resulting mixture was stirred overnight at room care and then diluted with ether, washed with 5% HCl solution, water and 1N sodium hydroxide solution. The organics were then dried over MgSO$_4$, filtered and concentrated in vacuo. The residue was triturated with ether/hexanes (1:1) to give 3.2 g (98%) of the product as a white solid. Electrospray Mass Spec: 436.0 (M+H)+.

EXAMPLE 316

2-[(4-Methoxy-benzenesulfonyl)-(tert-butoxycarbonyl)-amino]-3-(pyrrolidin-1-ylmethyl)-benzoic acid methyl ester To a solution of 3.05 (7.011 mmol) of the product of Example 315 in 165 mL of carbon tetrachloride was added 1.498 g (8.414 mmol) of N-bromosuccinimide and the mixture was heated to reflux while irradiated by a sunlamp for 3 h. The resulting mixture was cooled, washed with water, dried over MgSO$_4$, filtered and concentrated in vacuo.

To a solution of the resulting benzylic bromide in 30.0 mL of DMF was added 0.644 mL (7.71 mmol) of pyirolidine and 2.90 g of potassium carbonate. The raction mixture was then stirred overnight at room temperature and then diluted with ether, washed with water, dried over $Na_2SO_4$, filtered and concentrated in vacuo. The resulting residue was chromatographed on silica gel eluting with chloroform/methanol (9:1) to provide 2.076 g (59%) of the product as a white solid. Electrospray Mass Spec: 505.2 (M+H)+.

EXAMPLE 317

2-(4-Methoxy-benzenesulfonylamino)-3-pyrrolidin-1-ylmethyl-benzoic acid methyl ester To a solution of the product of example 316 in 10 mL of dichloromethane was added 10.0 mL of trifluoroacetic acid. The resulting solution was stirred at room temperature for 1 h and then concentrated in vacuo. The resulting residue was diluted with ether washed with saturated sodium bicarbonate solution, dried over $Na_2SO_4$, filtered and concentrated in vacuo. The residue was then triturated with ether to provide 0.93 g (57%) of the product as a pale yellow solid. Electrospray Mass Spec: 405.1 (M+H)+.

EXAMPLE 318

2-[(4-Methoxy-benzenesulfonyl)-pyridin-3-ylmethyl-amino]-3-pyrrolidin-1-ylmethyl-benzoic acid methyl ester By following the procedure of Example 45, 0.80 g (1.98 mmol) of the product of Example 317 gives 0.804 g (82%) of the product as a brown solid. Electrospray Mass Spec: 496.5 (M+H)+.

EXAMPLE 319

2-[(4-Methoxy-benzenesulfonyl)-pyridin-3-ylmethyl-amino]-3-pyrrolidin-1-ylmethyl-benzoic acid To a solution of 0.754 g (1.523 mmol) of the product of Example 318 in 15 mL of THF/Methanol (1:1) was added 7.6 mL of 1.0N sodium hydroxide solution. The resulting mixture was heated to reflux for 15 h and then concentrated in vacuo. The residue was diluted with water, neutralized with 5% HCl solution and exited with dichloromethane. The organics were dried over $Na_2SO_4$, filtered and concentrated in vacuo to provide 0.496 g (67%) of the product as a tan solid. Electrospray Mass Spec: 482.5 (M+H)+.

EXAMPLE 320

N-Hydroxy-2-[(4-methoxy-benzenesulfonyl)-pyridin-3-ylmethyl-amino]-3-pyrrolidin-1-ylmethyl-benzamide By following the procedure of Example 61 the product of Example 319 gives 0.174 g of the hydroxamic acid as a tan solid. Electrospray Mass Spec: 497.5 (M+H)+.

EXAMPLE 321

3-Formyl-2-(4-methoxy-benzenesulfonylamino)-benzoic acid methyl ester

To a solution of 1.0 g (2.985 mmol) of the product of Example 3 in 100 mL of carbon tetrachloride was added 0.20 g of dibenzoyl peroxide and 1.168 g (6.568 mmol) of N-bromosuccinimide. The resulting mixture was refluxed for 18 h, cooled, washed with sodium bisulfite solution and water, dried over $MgSO_4$, filtered and concentrated in vacuo. The residue was diluted with 10 mL of THF and 10 mL of 1N sodium hydroxide solution and the mixture was stirred at room temperature for 3 h. The reaction mixture was then acidified with 5% HCl and extracted with ether. The organics were dried over $MgSO_4$, filtered and concentrated in vacuo. The residue was triturated with ether to provide 0.477 g (47%) of the product as a white solid. Electrospray Mass Spec: 350.1 (M+H)+.

EXAMPLE 322

3-Formyl-2-[(4-methoxy-benzenesulfonyl)-octyl-amino]-benzoic acid methyl ester

To a solution of 1.0 g (2.865 mmol) of the product of Example 321 in 7.5 mL of DMF was added 0.143 g (3.582 mmol) of 60% sodium hydride followed by 0.74 mL (4.30 mmol) of n-octyl bromide. The reaction was stirred overnight at room temperature then diluted with ether, washed with water, dried over $MgSO_4$, filtered and concentrated in vacuo. The resulting residue was chromatographed on silica gel eluting with EtOAc/hexanes (1:3) to provide 0.592 g (49%) of the product as a white solid. Electrospray Mass Spec: 462.1 (M+H)+.

EXAMPLE 323

3-Hydroxymethyl-2-[(4-methoxy-benzenesulfonyl)-octyl-amino]-benzoic acid methyl ester To a solution of 0.547 g (1.187 mmol) of the product of Example 322 in 10 mL of methanol and 3 mL of THF was added 0.045 g (1.187 mmol) of sodium borohydride. The reaction was stired for 2 h at room temperature and then concentrated in vacuo. The residue was diluted with ether and washed with 5% HCl and water, dried over $MgSO_4$, filtered and concentrated in vacuo to provide 0.549 g (100%) as a colorless oil. Electrospray Mass Spec: 464.2 (M+H)+.

EXAMPLE 324

2-[(4-Methoxy-benzenesulfonyl)-octyl-aminol-3-(4-methyl-piperazin-1-ylmethyl)-benzoic acid methyl ester To a solution of 0.515 g (1.112 mmol) of the product of Example 323 in dichloromethane was added 0.438 g (1.668 mmol) of triphenylphosphine and 0.461 g (1.390 mmol) of carbon tetrabromide. The mixture was stirred for 1 h at room temperature and then concentrated in vacuo. The residue was filtered through a pad of silica gel eluting with EtOAc/hexanes (1:10) to provide the benzylic bromide.

To a solution of the bromide in 6.0 mL of DMF was added 0.136 mL (1.224 mmol) of N-methylpiperazine and 0.491 g (3.559 mmol) of potassium carbonate. The resulting mixture was stirred at room temperature overnight, diluted with ether, washed with water, dried over $Na_2SO_4$, filtered and concentrated in vacuo to provide 0.57 g (94%) of the benzylic amine-ester as a white solid. Electrospray Mass Spec: 546.2 (M+H)+.

EXAMPLE 325

N-Hydroxy-2-[(4-methoxy-benzenesulfonyl)-octyl-amino] -3- (4-methyl-piperazin-1-ylmethyl)-benzamide Following the procedure of Example 18, 0.507 g (0.930 mmol) of the product of Example 324 is converted into the corresponding carboxylate.

Following the procedure of Example 61 the carboxylate gives 0.343 g of the hydroxamic acid as a brown solid. Electrospray Mass Spec: 547.7 (M+H)+.

EXAMPLE 326

3-Formyl-2-[(4-methoxy-benzenesulfonyl)-thiophen-3-ylmethyl-amino]-benzoic acid methyl ester Following the procedure of Example 322, 1.0 g (2.865 mmol) of the product of Example 321 is reacted with 3-bromomethyl thiophene to give 1.10 g (86%) of the product as a white solid after chromatography on silica gel eluting with EtOAc/Hexanes (1:3). Electrospray Mass Spec: 446.1 (M+H)+.

EXAMPLE 327

2-[(4-Methoxy-benzenesulfonyl)-thiophen-3-ylmethyl-amino]-3- (4-methyl-piperazin-1-ylmethyl)-benzoic acid Following the procedure of Example 323, 1.06 g (2.387 mmol) of the product of Example 326 is converted into the corresponding alcohol.

Following the procedure of Example 324 the alcohol is converted into the corresponding benzylic amine-ester.

Following the procedure of Example 319 then gives 0.52 g of the carboxylic acid as a white solid. Electrospray Mass Spec: 516.2 (M+H)+.

EXAMPLE 328

N-Hydroxy-2-[(4-methoxy-benzenesulfonyl)-thiophen-3-ylmethyl-amino]-3-(4-methyl-piperazin-1-ylmethyl)-benzamide To a solution of 0.475 g (0.922 mmol) of the product of Example 327 in 8.0 mL of DMF was added 0.149 g (1.107 mmol) of HOBT and 0.235 g (1.227 mmol) of EDC. The reaction was then stirred for 1 h at room temperature and 0.28 mL (4.612 mmol) of a 50% solution of hydroxylamine in water was added. The reaction was stirred overnight and then concentrated in vacuo. The residue was diluted with EtOAc, washed with water and sodium bicarbonate solution, dried over $Na_2SO_4$, filtered and concenteeted in. The residue was dissolved in 5.0 mL of dichloromethane and 1.8 mL of a 1N solution of HCl in ether was added. After 1 h the reaction was diluted with ether and the resulting solid was filtered and dried in vacuo to give 0.242 g of the product as a white solid. Electrospray Mass Spec: 531.5 (M+H)+.

EXAMPLE 329

N-Hydroxy-2-[[(4-methoxyphenyl)sulfonyl] (phenylmethyl)-amino]-3-[(4-methyl-1-piperazinyl) methyl]benzamide Following the procedure of Example 322, 1.25 g (3.582 mmol) of the product of Example 321 reacts with benzyl bromide to give the N-benzyl sulfonamide.

Following the procedures of Examples 327, and 328, the sulfonamide gives 0.204 g of the hydroxamic acid as a white solid. Electrospray Mass Spec: 525.4 (M+H)+.

EXAMPLE 330

2-(4-Methoxy-benzenesulfonylamino)-3-methyl-benzoic acid tert-butylester

To a solution of 15.0 g (0.047 mol) of the product of Example 6 in 45 mL of toluene was added 50 mL of N,N-imethylformamide di-t-butyl acetal and the mixture was then heated to reflux for 18 h. The reaction was then cooled to room temperature and croatographed on silica gel eluting with EtOAc/Hexanes (1:3) to give 8.94 g (51%) of the product as a white solid. Electrospray Mass Spec: 378.1 (M+H)+.

EXAMPLE 331

2-[(4-Methoxy-benzenesulfonyl)-methyl-amino]-3-methyl-benzoic acid tert-butyl ester Following the procedure of Example 187 2.5 g (6.631 mmol) of the product of Example 330 gives 2.59 g (100%) of the N-methyl sulfonamide as a white foam. Electospray Mass Spec: 392.4 (M+H)+.

EXAMPLE 332

(2S)-1-{3-tert-Butoxycarbonyl-2-[(4-methoxy-benzenesulfonyl)-methyl-amino]-benzyl}-pyrrolidine-2-carboxylic acid methyl ester Following the procedure of Example 316, using L-proline methyl ester hydrochloride instead of pyrrolidine, 2.30 g (5.882 mmol) of the product of Example 331 gives 1.45 g (48%) of the diester as a white solid. Electrospray Mass Spec: 519.5 (M+H)+.

EXAMPLE 333

(2S)-1-{3-Carboxy-2-[(4-methoxy-benzenesulfonyl)-methyl-amino]-benzyl}-pyrrolidine-2-carboxylic acid methyl ester To a solution of 1.39 g (2.678 mmol) of the product of Example 332 in 5.0 mL of dichloromethane was added 5.0 mL of trifluoroacetic acid. The reaction was stirred at room temperature for 2 h and then concentrated in vacuo. The residue was chromatographed on silica gel eluting with chlorofornmethanol (9:1) to give 1.24 g (100%) of the carboxylic acid as a white foam. Electrospray Mass Spec: 463.0 (M+H)+.

EXAMPLE 334

(2S)-1-{3-Hydroxycarbamoyl-2-[(4-methoxy-benzenesulfonyl)-methyl-amino]-benzyl}-pyrrolidine-2-carboxlic acid methyl ester Following the procedure of Example 61 1.305 g (2.262 mmol) of the product of Example 333 gives 0.285 g of the hydroxamic acid as a tan solid. Electrospray Mass Spec: 478.1 (M+H)+.

EXAMPLE 335

3-Formyl-2-[(4-methoxy-benzenesulfonyl)-pyridin-3-ylmethyl-amino]-benzoic acid methyl ester To a solution of 0.20 g (0.573 mmol) of the product of Example 321 in 2.5 mL of DMF was added 0.099 g (0.602 mmol) of 3-picolyl chloride hydrochloride and 0.249 g (1.805 mmol) of potassium carbonate. The reaction was stined for 18 h at room temperature and then the reaction was then diluted with water and extracted with ether. The combined organics were washed with water, dried over $Na_2SO_4$, filtered and concentrated in vacuo. The residue was triturated with ether to give 0.158 g (63%) of the product as tan crystals. Electrospray Mass Spec: 440.9 (M+H)+.

EXAMPLE 336

3-Hydroxymethyl-2-[(4-methoxy-benzenesulfonyl)-pyridin-3-ylmethyl-amino]-benzoic acid methyl ester To a solution of 0.10 g (0.227 mmol) of the product of Example 335 in 5 mL of methanol and 2.0 mL of THF was added 8.6 mg of sodium borohydride. The reaction was stirred for 1 h at room temperature and then concentrated in vacuo. The residue was diluted with dichloromethane, washed with water, and the organics were then dried over $Na_2SO_4$, filtered and concentrated in vacuo. The resulting tan solid was washed with ether and dried in vacuo to give 0.086 g (86%) of the alcohol. Electrospray Mass Spec: 442.9 (M+H)+.

EXAMPLE 337

2-[(4-Methoxy-benzenesulfonyl)-pyridin-3-ylmethyl-amino]-3-(tetrahydro-pyran-2-yloxymethyl)-benzoic acid methyl ester To a solution of 0.500 g of the product of Example 336 in 15 mL of dichloromethane was added 0.21 mL (2.262 mmol) of dihydropyran and 0.030 g of toluenesulfonic acid monohydrate. The reaction was stirred at room temperate for 24 h and then diluted with dichloromethane. The organics were washed with 1N sodium hydroxide solution and water, dried over $Na_2SO_4$, filtered and concentrated in vacuo. The residue was chromatographed on silica gel eluting with EtOAc to give 0.436 g (73%) of the ThP-ether as a brown foam. Electrospray Mass Spec: 527.2 (M+H)+.

EXAMPLE 338

2-[[(4-Methoxyphenyl)sulfonyl](3-pyridinylmethyl)amino]-3-[[(tetrahydro-2H-pyran-2-yl)oxy]methy] benzoic acid Following the procedure of Example 190 0.376 g (0.715 mmol) of the product of Example 337 gives 0.370 g (100%) of the carboxylate salt as a brown foam. Electrospray Mass Spec: 511.1 (M–H)–.

EXAMPLE 339

N-Hydroxy-2- ((4-methoxy-benzenesulfonyl)-pyridin-3-ylmethyl-amino]-3-(tetrahydro-pyran-2-yloxymethyl)-benzamide To a solution of 0.851 g (1.662 mmol) of the product of Example 338 in 10.0 mL of DMF was added 0.269 g (1.995 mmol) of HOBT (1-hydroxybenzotriazole) and 0.424 g (2.211 mmol) of 1-(3-dimethylaminopropyl)-3-ethylcarbodimide hydrochloride (EDC). The reaction was then stirred for 1 h at room temperature and 0.578 g (8.311 mmol) of hydroxylamine hydrochloride and 1.73 mL of triethylamine was added. The reaction was stired overnight and then concentrated in vacuo. The residue was diluted with ether, washed with water and sodium bicarbonate solution, dried over $Na_2SO_4$, filtered and concentrated in vacuo to provide 0.635 g (72%) of the hydroxamic acid as a tan foam. Electrosray Mass Spec: 528.1 (M+H)+.

EXAMPLE 340

N-Hydroxy-3-hydroxymethyl-2-[(4-methoxy-benzenesulfonyl)-pyridin-3-ylmethyl-amino]-benzamide To a solution of 0.352 g (0.668 mmol) of the product of Example 339 in 6.5 mL of dichloromethane and 1.3 mL of methanol was added 1.3 mL of a 1M solution of HCl in ether. The reaction was stirred at room temperature for 5 h and the resulting precipitate was collcted by filtration, washed with ether and dried in vacuo to give 0.320 g (100%) of the alcohol as a white solid. Electrospray Mass Spec: 444.2 (M+H)+.

EXAMPLE 341

2-[Benzyl-(4-methoxy-benzenesulfonyl)-amino]-3-(2-hydroxy-ethoxy)-benzoic acid methyl ester To a solution of 2.53 g (4.677 mmol) of the product of Example 38 in 20 mL of dichloromethane was added 5.0 mL of tifluoroacetic acid. The reaction was stirred at room tciaerpate for 3 h and then concentrated in vacuo. The residue was triturated with Ether/Hexanes (1:1) and the resulting white solid (2.063 g) was collected by filtration and dried in vacuo.

The carboxylic acid was then dissolved in 40 mL of dry THF cooled to 0° and 19.6 mL of a 1M solution of Borane/THF was added. The reaction was allowed to warm to room temperature and stirred for 18 h. The reaction was quenched with 10 mL of acetic acid-water (1:1), diluted with water and extracted with ether. The organics were died over $MgSO_4$, filtered and concentrated in vacuo. The residue was chromatographed on sicca gel eluting with EtOAc)Hexanes (1:1) to provide 1.845 g of the alcohol as a white solid. Electrospray Mass Spec: 472.2 (M+H)+.

EXAMPLE 342

2-[Benzyl-(4-methoxy-benzenesulfonyl)-amino]-3-(2-hydroxy-ethoxy)-benzoic acid

To a solution of the product of 1.459 g (3.098 mmol) of Example 341 in 30 mL of THF/Methanol (1:1) was added 15.5 mL of 1N sodium hydroxide solution and the reaction mixture was then heated to reflux overnight. The reaction was then cooled to room temperature, acidified with 5% HCl solution and extracted with ether. The combined organics were dried over $MgSO_4$, filtered and concentrated in vacuo. The residue was chnoatographed on silica gel eluting with EtOAc/hexanes (2:1) to provide 1.22 g of the carboxy-alcohol as a white solid. Electrospray Mass Spec: 456.1 (M–)–.

EXAMPLE 343

2-[Benzyl-(4-methoxy-benzenesulfonyl)-amino]-3-[2-(tert-butyl-dimethyl-silanyloxy)-ethoxy]-benzoic acid To a solution of 1.22 g (2.67 mmol) of the product of Example 342 in 6.0 ml of DMF was added 0.966 g (6.407 mmol) of t-butyldimethylsilyl chloride and 0.908 g (0.013 mol) of imidazole. The reaction was stirred for 5 h at room temperature and then diluted with water and 1N sodium hydroxide solution and stirred for an additional hour. The reaction was then acidified to pH5 and extracted with ether. The organics were dried over $MgSO_4$, filtered and concentrated in vacuo. The residue was chromatographed on silica gel eluting with EtOAc/bexanes (1:3) to provide 1.34 g (88%) of the carboxylic acid as a white solid. Electrospray Mass Spec: 570.0 (M+H)+.

EXAMPLE 344

2-[Benzyl-(4-methoxy-benzenesulfonyl)-amino]-3-[2-(tert-butyl-dimethyl-silanyloxy)-ethoxy]-N-hydroxy-benzamide Following the procedure of Example 328, 1.107 g (1.939 mmol) of the product of Example 343 gives 1.0 g (88%)of

EXAMPLE 345

2-[Benzyl-(4-methoxy-benzenesulfonyl)-amino]-N-hydroxy-3-(2-hydroxy-ethoxy)-benzamide To a solution of 0.957 g (1.633 mmol) of the product of Example 344 in 20 mL of acetonitrire was added 1.5 mL of 48% hydrofluoric acid. The reaction was stined at room temprature for 3 h and then diluted with dichloromethane and washed with water. The organics were dried over $MgSO_4$, filtered and concentrated in vacuo to give 0.76 g (99%) of the hydroxamic acid as a white foam. Electrospray Mass Spec: 473.3 (M+H)+.

EXAMPLE 346

2-{5-Bromo-2-[(4-methoxy-benzenesulfonyl)-methyl-amino]-3-methoxycarbonyl-benzyl}-malonic acid dimethyl ester To a solution of 1.50 g (3.505 mmol) of the product of Example 202 in 65 mL of carbon tetrachloride was added 0.749 g (4.206 mmol) of N-bromosuccinimide and 0.06 g of dibenzoyl peroxide. The reaction was heated to reflux for 15 h, cooled and washed with water. The organics were dried over $MgSO_4$, filtered and concentrated in vacuo. The residue was chromatographed on silica gel eluting with EtOAc/Hiexanes (1:3) to provide 1.46 g of the benzylic bromide.

To a solution of the benzylic bromide in 7.5 mL of DMF was added 0.39 mL (3.456 mmol) of dimethyl malonate followed by 0.171 g (3.168 mmol) of sodium methoxide. The reactioon was stirred at room temperature for 24 h then acidified with 10% HCl solution and extracted with ether. The organics were dried over $MgSO_4$, filtered and concentraed in vacuo. The residue was chromatographed on silica gel eluting with EtOA/Hexanes (1:3) to provide 0.766 g (48%) of the triester as a colorless oil. Electrospray Mass Spec: 558.0 (M+H)+.

EXAMPLE 347

2-{5-Bromo-3-carboxy-2-[(4-methoxy-benzenesulfonyl)-methyl-amino]-benzyl}-malonic acid Following the procedure of Example 342, 0.674 g (1.208 mmol) of the product of Example 45 gives 0.623 g (100%) of the triacid as a tan foam. Electrospray Mass Spec: 513.9 (M–H)–.

EXAMPLE 348

5-Bromo-3-(2-carboxy-ethyl)-2-[(4-methoxy-benzenesulfonyl)-methyl-amino]-benzoic acid A solution of 0.542 g (1.050 mmol) of the product of Examnple 347 in 25 mL of pyridine was heated to reflux for 12 h and then cooled to room temperure. The reaction was diluted with water, acidified with 10% HCl solution and extracted with EtOAc. The combined organics were dried over $MgSO_4$, filtered and concentrated in vacuo. The residue was triturated with ether to give 0.339 g of the diester as a tan solid. Electrospray Mass Spec: 470.0 (M–H)–.

EXAMPLE 349

5-Bromo-N-hydroxy-3-[2-(hydroxycarbamoyl)-ethyl]-2-[(4-methoxy-benzenesulfonyl)-methyl-amino]-benzamide Following the procedure of Example 23 0.304 g (0.644 mmol) of the product of Example 348 gives 0.114 g (35%) of the bis-hydroxamic acid as a white solid. Electrospray Mass Spec: 504.0 (M+H)+.

EXAMPLE 350

N-Hydroxy-3-[2-(hydroxycarbamoyl)-ethyl]-2-[(4-methoxy-benzenesulfonyl)-methyl-amino]-benzamide Following the procedures of Examples 346 to 349 the product of Example 188 gives the bis-hydroxamic acid as a white foam. Electrospray Mass Spec: 424.2 (M+H)+.

EXAMPLE 351

5-Biphenyl-4-ylethynyl-2-[(4-methoxy-benzenesulfonyl)-methyl-amino]-3-methyl-benzoic acid methyl ester To a solution of 1.0 g (2.336 mmol) of the product of Example 202 in 7.5 mL of DMF was added 0.50 g (2.804 mmol) of ethynyl biphenyl, 0.033 g (0.047 mmol) of bis triphenylphosphine palladium(II) dichloride 4.4 mg of copper(I) iodide and 7.5 mL of triethylamine. The reaction was heated to 80° for 5 h and then diluted with ether. the organics were washed with water, 5% HCl solution and sodium bicarbonate solution, dried over $MgSO_4$, filtered and concentrated in vacuo. The residue was chromatographed on silica gel cluting with EtOAc/hexanes (1:3) to provide 0.777 g (63%) of the alkyne as a brown foam. Electrospray Mass Spec: 526.2 (M+H)+.

EXAMPLE 352

5-Biphenyl-4-ylethynyl-2-[(4-methoxy-benzenesulfonyl)-methyl-amino]-3-methyl-benzoic acid Following the procedure of Example 18, 0.400 g (0.762 mmol) of the product of Example 351 gives 0.383 g (98%) of the carboxylic acid as a brown foam. Electrospray Mass Spec: 510.1 (M–H)–.

EXAMPLE 353

5-Biphenyl-4-ylethynyl-N-hydroxy-2-[(4-methoxy-benzenesulfonyl)-methyl-amino]-3-methyl-benzamide Following the procedure of Example 23, 0.132 g (0.258 mmol) of the product of Example 352 gives 0. 107 g (79%) of the hydroxamic acid as a yellow solid. Electrospray Mass Spec: 527.1 (M+H)+.

EXAMPLE 354

5-(2-Biphenyl-4-yl-ethyl)-2-[(4-methoxy-benzenesulfonyl)-methyl-amino]-3-methyl-benzoic acid To a solution of 0.20 g (0.391 mmol) of the product of Example 352 in 25 mL of methanol and 10 mL of ethyl acetate was added 0.050 g of 10% palladium on carbon. The mixture was hydrogenated in a Parr apparatus at 30 psi of hydrogen for 5 h, then filtered through Celite. The Celite pad was washed with 100 mL of methanol and 100 mL of ethyl acetate and the filtrate was concentrated in vacuo. The residue was trituratedwith ether to give 0.173 g (86%) of the carboxylic acid as a pale yellow solid. Electrospray Mass Spec: 514.2 (M–H)–.

EXAMPLE 355

5-(2-Biphenyl-4-yl-ethyl)-N-hydroxy-2-[(4-methoxy-benzenesulfonyl)-methyl-amino]-3-methyl-benzamide Following the procedure of Example 23, 0.138 g (0.268 mmol) of the product of Example 354 gives 0.091 g (64%) of the hydroxamic acid as a yellow solid. Electrospray Mass Spec: 531.1 (M+H)+.

EXAMPLE 356

5-Dodec-1-ynyl-2-[(4-methoxy-benzenesulfonyl)-methyl-amino]-3-methyl-benzoic acid methyl ester Following the procedure of Example 351, using 1-dodecyne instead of ethynyl biphenyl, 1.0 g (2.336 mmol) of the product of Example 202 gives 0.874 g (73%) of the alkyne as a brown oil. Electrospray Mass Spec: 514.4 (M+H)+.

EXAMPLE 357

5-Dodec-1-ynyl-2-[(4-methoxy-benzenesulfonyl)-methyl-amino]-3-methyl-benzoic acid Following the procedure of Example 18, 0.808 g (1.575 mmol) of the product of Example 356 gives 0.731 g (93%) of the carboxylic acid as a pale yellow oil. Electrospray Mass Spec: 498.2 (M–H)–.

EXAMPLE 358

5-Dodec-1-ynyl-N-hydroxy-2-[(4-methoxy-benzenesulfonyl)-methyl-amino]-3-methyl-benzamide Following the procedure of Example 23, 0.200 g (0.401 mmol) of the product of Example 357 gives 0.170 g (83%) of the hydroxamic acid as a colorless oil. Electrospray Mass Spec: 515.2 (M+H)+.

EXAMPLE 359

5-Dodecyl-2-[(4-methoxy-benzenesulfonyl)-methyl-amino]-3-methyl-benzoic acid

Following the procedure of Example 354, 0.217 g (0.435 mmol) of the product of Example 357 gives 0.214 g (98%) of the carboxylic acid as a pale white solid. Electspray Mass Spec: 502.3 (M–H)–.

EXAMPLE 360

5-Dodecyl-N-hydroxy-2-[(4-methoxy-benzenesulfonyl)-methyl-amino]-3-methyl-benzamide Following the procedure of Example 23, 0.189 g (0.376 mmol) of the product of Example 359 gives 0.153 g (79%) of the hydroxamic acid as a brown oil. Electrospray Mass Spec: 519.2 (M+H)+.

EXAMPLE 361

2-[(4-Methoxy-benzenesulfonyl)-pyridin-3-ylmethyl-amino]-3-methoxymethyl-benzoic acid methyl ester To a solution of 0.200 g (0.452 mmol) of the product of Example 336 in 5.0 mL of dry THF was added 0.022 g (0.543 mmol) of 60% sodium hydride followed by 0.028 mL of iodomethane. The reaction was stired at room temperature for 18 h and then diluted with ethyl acetate. The organics were washed with water and brine, dried over $Na_2SO_4$, filtered and concentrated in vacuo. The residue was chromatographed on silica gel eluting with EtOAc to provide 0.057 g (28%) of the methyl ether as ayellow solid. Electrospray Mass Spec: 457.3 (M+H)+.

EXAMPLE 362

2-[(4-Methoxy-benzenesulfonyl)-pyridin-3-ylmethyl-amino]-3-

Following the procedure of Example 53, 0.275 g (0.603 mmol) of the product of Example 361 gives 0.267 g (100%) of the carboxylate salt as a yellow foam. Electspray Mass Spec: 443.1 (M+H)+.

EXAMPLE 363

N-Hydroxy-2-[(4-methoxy-benzenesulfonyl)-pyridin-3-ylmethyl-amino]-3-methoxymethyl-benzamide Following the procedure of Example 328, 0.260 g (0.588 mmol) of the product of Example 362 gives 0.115 g of the hydroxamic acid as a tan solid. Electrospray Mass Spec: 456.3 (M–H)–.

EXAMPLE 364

3-Formyl-2-(4-methoxy-benzenesulfonylamino)-benzoic acid tert-butyl ester

Following the procedure of Example 321, 1.90 g (5.04 mmol) of the product of Example 330 gives 1.19 g (60%) of the aldehyde as a pale yellow solid. Electrospray Mass Spec: 392.2 (M+H)+.

EXAMPLE 365

3-Formyl-2-[(4-methoxy-benzenesulfonyl)-pyridin-3-ylmethylamino]-benzoic acid tert-butyl ester Following the procedure of Example 335, 1.106 g (2.829 mmol) of the product of Example 364 gives 1.282 (94%) of the N-picolyl sulfonamide as a brown oil. Electspray Mass Spec: 483.4 (M+H)+.

EXAMPLE 366

2-[(4-Methoxy-benzenesulfonyl)-pyridin-3-ylmethyl-amino]-isophthalic acid mono-tert-butyl ester To a solution of 0.417 g (0.865 mmol) of the product of Example 365 in 40 mL of water and 25 mL of THF was added 0.126 g (1.298 nmol) of sulfamic acid and 0.122 g (1.341 nmol) of sodium chlorite. The reaction was stirrd overnight at room temperature and then concentrated in vacuo. The residue was diluted with water and exte with chloroform. The organics were dried over $Na_2SO_4$, filtered and concentrated in vacuo. The residue was triturated with ether to give 0.080 g (77%) of the carboxylic acid as a pale yellow solid. Electrospray Mass Spec: 499.4 (M+H)+.

Example 367

N-Hydroxy-2-[(4-methoxy-benzenesulfonyl)-pyridin-3-ylmethylamino]-isophthalamic acid tert-butyl ester Following the procedure of Example 328, 0.354 g (0.711 mmol) of the product of Example 366 gives 0.063 g (17%)

105 of the hydroxamic acid as a brown foam. Electospray Mass Spec: 514.3 (M+H)+.

EXAMPLE 368

2-[(4-Methoxy-benzenesulfonyl)-pyridin-3-ylmethyl-amino]-isophthalic acid monomethyl ester Following the procedure of Example 366, 0.10 g (0.227 mmol) of the product of Example 335 gives 0.080 g (77%) of the carboxylic acid as a white solid. Electrospray Mass Spec: 457.3 (M+H)+.

EXAMPLE 369

N-Hydroxy-2-[(4-methoxy-benzenesulfonyl)-pyridin-3-ylmethyl-amino]-isophthalamic acid methyl ester Following the procedure of Exarmple 23, 0.600 g (1.316 mmol) of the product of Example 368 gives 0.48 g (77%) of the hydroxamic acid. The hydroxamate was dissolved in 10.0 mL of dichloromethane and 0.5 mL of methanol and 2.0 mL of a 1N solution of HCl in ether was added. After 1 h the resulting solid was filtered and dried in vacuo to give 0.358 g of the product as a tan solid. Electrospray Mass Spec: 472.2 (M+H)+.

EXAMPLE 370

3-Acetoxymethyl-5-bromo-2-[(4-methoxy-benzenesulfonyl)-methyl-amino]-benzoic acid methyl ester To a solution of 1.00 g (2.336 mmol) of the product of Example 202 in 50 mL of carbon tetrachloride was added 0.457 g (2.57 mmol) of N-bromosuccinimide the reaction was heated to reflux under a sunlamp for 1 h, cooled and washed with water. The organics were dried over MgSO$_4$, filtered and concentrated in vacuo. The residue was dissolved in 15 mL of DMF and 0.958 g (0.012 mmol) of sodium acetate was added. The reaction was heated to 80° for 4 h, cooled to room temperature and diluted with ether. The organics were washed with water, dried over MgSO$_4$, filtered and concentrated in vacuo. The residue was chromatographed on silica gel eluting with EtOAc/hexanes (1:3) to provide 0.408 g (36%) of the acetate as a colorless oil. Electrospray Mass Spec: 487.8 (M+H)+.

EXAMPLE 371

5-Bromo-2-[(4-methoxy-benzenesulfonyl)-methyl-amino]-isophthalic acid monomethyl ester To a solution of 0.272 g (0.826 mmol) of the product of Example 370 in 2.0 mL of THF/MeOH (1:1) was added 0.87 mL of 1N sodium hydroxide solution and the reaction was stir for 3 h at room temperature. The reaction was then extracted with ether. The combined organics were dried over MgSO$_4$, filtered and concentrated in vacuo. The residue was triturated with ether to give 0.241 g of the alcohol as a white solid.

The alcohol was then dissolved in 1.5 mL of DMF and 0.366 g (0.973 mmol) of pyridinium dichromate was added and the reaction was stirred overnight. The reaction mixture was then diluted with ether, washed with water, dried over MgSO$_4$, filtered and concentrated in vacuo. The residue was dissolved in 17 mL of THF and 28 mL of water and 0.091 g (1.005 mmol) of sodium chlorite and 0.094 g (0.973 mmol) of sulfamic acid was added. The reaction was stirred overnight at room temperature, concentrated in vacuo, diluted with water and extraced with chloroform. The orgamics were dried over MgSO$_4$, filtered and concentrated in vacuo. The residue was triturated with ether to give 0.282 g of the carboxylic acid as a white solid. Electrospray Mass Spec: 456.0 (M–H)–.

EXAMPLE 372

2-[(4-Methoxy-benzenesulfonyl)-methyl-amino]-isophthalic acidmonomethyl ester

Following the procedure of Example 370, 0.50 g (1.168 mmol) of the product of Example 188 gives 0.314 g (66%) of the acetate. Following the procedure of Example 371 0.287 g (0.705 mmol) of the acetate gives 0.152 g of the carboxylic acid as a white solid. Electrospray Mass Spec: 377.9 (M–H)–.

EXAMPLE 373

N-Hydroxy-2-[(4-methoxy-benzenesulfonyl)-methyl-amino]-isophthalamic acid methyl ester Following the procedure of Example 23, 0.126 g (0.332 mmol) of the product of Example 372 gives 0.116 g (89%) of the hydroxamic acid as a white solid. Electrospray Mass Spec: 394.8 (M+H)+.

EXAMPLE 374

N-Hydroxy-2-[(4-methoxy-benzenesulfonyl)-pyridin-3-ylmethyl-amino]-isophthalamic acid To a solution of 0.235 g (0.458 mnmol) of the product of Example 367 dissolved in 5 mL of dichlo ethane was added 2 mL of trifluoroacetic acid. The reaction was stirred at room tenperature for 2 h and then concentrated in vacuo. The residue was triturated with ether and the resulting solid was collected by filtration and dried in vacuo to give 0.178 (65%) of the hydroxamic acid as a tan solid. Electrospray Mass Spec: 456.4 (M–H)–.

EXAMPLE 375

N-Hydroxy-2-[(4-methoxy-benzenesulfonyl)-pyridin-2-ylmethyl-amino]-3-methyl-benzamide Following the procedure of Example 45, 0.750 g (2.239 mmol) of the product of Example 3 was alkylated with 2-picolyl chloride hydrochloride to give 0.916 g (96%) of the N-picolyl sulfonamide.

Following the procedure of Example 53 the ester was then hydrolyzed to provide the corresponding carboxylic acid.

Following the procedure of Example 369 the acid was converted into the hydroxamic acid to give 0.180 g of the pyridinium salt as a brown foam. Electrospray Mass Spec: 428.1 (M+H)+.

EXAMPLE 376

N-Hydroxy-2-[(4-methoxy-benzenesulfonyl)-pyridin-4-ylmethyl-amino]-3-methyl-benzamide Following the procedure of Example 45, 0.750 g (2.239 mmol) of the product of Example 3 was alkylated with 4-picolyl chloride hydrochloride to give 0.897 g (94%) of the N-picolyl sulfonamide.

Following the procedure of Example 53 the ester was then hydrolyzed to provide the corresponding carboxylic acid.

Following the procedure of Example 369 the acid was converted into the hydroxamic acid to give 0.180 g of the pyridinium salt as a brown foam. Electrospray Mass Spec: 428.2 (M+H)+.

EXAMPLE 377

2-[(4-Diethylaminomethyl-benzyl)-(4-methoxy-benzenesulfonyl)-amino]-N-hydroxy-3-methyl-benzamide Following the procedure of Example 9, 1.50 g (4.478 mmol) of the product of Example 3 was alkylated with 4-carboethoxybenzyl bromide to give 2.00 g (93%) of the benzylated sulfonamide as a tan solid. Electrospray Mass Spec: 484.2 (M+H)+.

This ester was dissolved in 9.0 mL of MeOH/THF (1:1) and 4.3 mL of 1.0N sodium hydroxide solution was added. The reaction was stired for 3 h at room temperature, acidified with 5% HCl solution and extracted with ethyl acetate. The combined organics were dried over $MgSO_4$, filtered and concentrated in vacuo to give the carroxylic acid as a white solid which was washed with ether and dried. Electrospray Mass Spec: 468.5 (M–H)–.

The acid was then reduced with borane-THF as in Example 341, to provide the alcohol as a white solid. Electrospray Mass Spec: 456.2 (M+H)+.

The alcohol was converted into the corresponding diethylamine, according to the procedure in Example 324, isolated as a white solid. Electrospray Mass Spec: 511.5 (M+H)+.

Hydrolysis of the benzoate ester according to the procedure of Example 319, followed by conversion to the hydroxamic acid and salt formation according to the procedure of Example 369 gives 0.105 g of the hydroxamate as a white solid. Electrospray Mass Spec: 512.1 (M+H)+.

EXAMPLE 378

2-[(4-Dimethyl-aminomethyl-benzyl)-(4-methoxy-benzenesulfonyl)-amino]-N-hydroxy-3-methyl-benzamide Following the procedures of Example 377, 1.50 g (4.478 mmol) of the product of Example 3 was converted into the dimethylamine-hydroxamate, isolated as a white foam. Electrospray Mass Spec: 483.9 (M+H)+.

EXAMPLE 379

2-[(4-Methoxy-benzenesulfonyl) prop-2-ynyl-amino]-3-methyl-benzoic acid methyl ester Following the procedure of Example 9, 1.50 g (4.478 mmol) of the product of Example 3 was alkylated with propargyl bromide to give 1.33 g (79%) of the propargyl sulfonamide as a white solid. Electrospray Mass Spec: 374.3 (M+H)+.

EXAMPLE 380

2-[(4-Diethylamino-but-2-ynyl)-(4-methoxy-benzenesulfonyl)-amino]-3-methyl-benzoic acid methyl ester To a solution of 1.27 g (3.61 mmol) of of the product of Example 379 in 11 mL of dioxane and 1.3 mL of acetic acid was added 0.293 g of paraformaldehyde, 0.75 mL of diethylamine and 13 mg of cuprous chloride. The reaction was stire at room temperture for 15 minutes and then heated to reflux for 1.5 h, after which the reaction color had changed from green to brown. The reaction was cooled and then extted with 10% HCl solution. The acid wash was then basified with 1N sodium hydroxide solution and extracted with ether. The combined organics were dried over $Na_2SO_4$, filtered and concentrated in vacuo to give 1.56 g (100%) of the propargylic amine as a brown oil. Electrospray Mass Spec: 459.5 (M+H)+.

EXAMPLE 381

2-[(4-Diethylamino-but-2-ynyl)-(4-methoxy-benzenesulfonyl)-amino]-N-hydroxy-3-methyl-benzamide Following the procedure of Example 319, 1.50 g (3.275 mmol) of the product of Example 380 was hydrolyzed to give 0.86 g (59%) of the carboxylic acid as a tan foam. Electrospray Mass Spec: 443.4 (M–H)–.

Following the procedure of Example 328, 0.649 g (1.462 mmol) of the carboxylic acid gives 0.228 g of the hydroxamic acid-amine salt as a tan solid. Electrospray Mass Spec: 460.1 (M+H)+.

EXAMPLE 382

N-Hydroxy-2-{(4-methoxy-benzenesulfonyl)-[4-(4-methyl-piperazin-1-yl)-benzyl]-amino}-3-methyl-benzamide Following the procedure of Example 9, 1.50 g (4.478 mmol) of the product of Example 3 was alkylated with 4-bromobenzyl bromnide to give 2.16 g (96%) of the benzylated sulfonamide as a pale yellow solid. Electrospray Mass Spec: 504.0 (M+H)+.

To a solution of 2.04 g (4.048 mrol) of the aryl bromide in 60 mL of toluene was added 0.99mL (8.91 mmol) of N-methylpiperazine, 0.856 g (8.91 mmol) of sodium t-butoxide, 0.148 g (0.162 nunol) of tris-(dibenzylideneacetone)dipalladium and 0.301 g (0.486 mmol) of (R)-(+)-2,2'-bis(diphenylphosphino-1'-binaphthyl (BINAP). The resulting mixture was heated to 80° for 3 h then cooled to room temperature. The reaction was diluted with ether and filtered through Celite. The filtrate was concentrated in vacuo and the residue was chromatographed on silica gel eluting with ethyl acetate to give 1.3 g of the aryl pipera.ine.

Following the procedure of Example 319 the aryl piperazine-ester was hydrolyzed to give 0.837 g (66%) of the carboxylic acid as a brown foam. Electrospray Mass Spec: 508.6 (M–H)–.

Following the procedure of Example 328 the carboxylic acid was converted into 0.432 g of the hydroxamic acid-amine salt, isolated as a pale yellow solid. Electrospray Mass Spec: 525.1 (M+H)+.

EXAMPLE 383

4-[(2-Hydroxycarbamoyl-6-methyl-phenyl)-(4-methoxy-benzenesulfonyl)-amino]-butyric acid ethyl ester Following the procedure of Example 45, 0.750 g (1.989 mmol) of the product of Example 330 was rted with ethyl bromobutyrate to give 0.96 g (98%) of the alkylated sulfonamide as a colorless oil. Electrospray Mass Spec: 492.4 (M+H)+.

To a solution of 0.828 g (1.686 mmol) of the t-butyl ester in 5 mL of dichloromethane was added 5.0 mL of trifluoroacetic acid. The reaction was stirred at room temperature for 2 h and then concentrated in vacuo. The residue was triturated with ether/hexanes (1:1) and the resulting white solid carboxylic acid (0.653 g) was collected by filtration and dried in vacuo. Electrospray Mass Spec: 434.2 (M–H)–.

Following the procedure of Example 23, 0.603 g (1.386 mmol) of the carboxylic acid gives 0.234 g (38%) of the hydroxamic acid as a white foam. Electrospray Mass Spec: 451.4 (M+H)+.

EXAMPLE 384

5-[(2-Hydroxycarbamoyl-6-methyl-phenyl)-(4-methoxy-benzenesulfonyl)-amino]-pentanoic acid ethyl ester Following the procedure of Example 45, 0.750 g (1.989 mmol) of the product of Example 330 was reacted with ethyl bromovalerate to give 0.93 g (93%) of the alkylated sulfonamide as a white solid. Electrospray Mass Spec: 506.4 (M+H)+.

To a solution of 0.813 g (1.610 mmol) of the t-butyl ester in 5 mL of dichloromethane was added 5.0 mL of trifluoroacetic acid. The reaction was stirred at room temperature for 2 h and then concentrated in vacuo. The residue was triturated with ether/hexanes (1:1) and the resulting white solid carboxylic acid (0.693 g) was colkcted by filtration and dried in vacuo. Electrospray Mass Spec: 448.1 (M–H)–.

Following the procedure of Example 23, 0.631 g (1.405 mmol) of the carboxylic acid gives 0.219 g (34%) of the hydroxamic acid as a brown glass. Electrospray Mass Spec: 465.4 (M+H)+.

EXAMPLE 385

[(2-Hydroxycarbamoyl-6-methyl-phenyl)-(4-methoxy-benzenesulfonyl)-amino]-acetic acid benzyl ester Following the procedure of Example 9, 1.50 g (3.979 mmol) of the product of Example 330 was reacted with benzyl 2-bromoacetate to give 2.03 g (97%) of the alkylated sulfonamide as a colorless oil. Electrospray Mass Spec: 526.3 (M+H)+.

To a solution of 1.00 g (1.905 mmol) of the t-butyl ester in 5 mL of dichloromethane was added 5.0 mL of trirluoroacetic acid. The reaction was stirred at room temperature for 1 h and then concentrated in vacuo to give 0.893 g (100%) of the carboxylic acid as a white foam. Electrospray Mass Spec: 468.2 (M–H)–.

Following the procedure of Example 23, 0.802 g (1.71 mmol) of the carboxylic acid gives 0.675 g (82%) of the hydroxamic acid as a white foam. Electrospray Mass Spec: 485.3 (M+H)+.

EXAMPLE 386

N-Hydroxy-2-[[(4-methoxyphenyl)sulfonyl][2-oxo-2-[(2pyridinylmethyl)-amino]ethyl]amino]-3-methlylbenamide Following the procedure of Example 9, 4.0 g (0.011 mol) of the product of Example 330 was reacted with benzyl 2-bromoacetate to give 5.57 g (100%) of the alkyad sulfonamide as a colorless oil. Electrospray Mass Spec: 526.3 (M+H)+.

To a solution of 5.50 g (0.010 mol) of the benzyl ester in 150 mL of ethanol was added 3.30 g (0.052 mol) of ammonium formate and 0.550 g of 10% palladium on carbon. The reaction was stired at room temperature for 18 h and then filtered through celite. The filtrate was concentrated in vacuo, diluted with ethyl acetate, washed with water, dried over MgSO$_4$, filtered and concentrated. The residue was chromatographed on silica gel eluting with EtOAc/hexanes (1:1) to give the carboxylic acid as a white foam. Electrospray Mass Spec: 436.2 (M+H)+.

To a solution of 1.00 g (2.299 mmol) of the carboxylic acid in 10 mL of dichloromethane was added 0.36 mL of DMF followed by 2.3 mL of a 2M solution of oxalyl chloride in dichloromethane. The reaction was stirred at room temperature for 1 h and then poured into a 0° C. solution of 0.47 mL (4.598 mmol) of 2-aminomethylpyridine and 0.96 mL of triethylamine in 10 mL of dichloromethane. The reaction was stirred overnight and then poured into water and extrccted with ether. The organics were then washed with water, dried over Na$_2$SO$_4$, filtered and concentrated in vacuo. The residue was choomatogwaphed on silica gel eluting with ethyl acetate to give 1.094 g (91%) of the amide as a white foam. Electrospray Mass Spec: 526.4 (M+H)+.

Next, HCl gas was bubbled through a solution of 0.985 g (1.876 mmol) of the amide dissolved in 20 mL of dichloromethane for 10 minutes. The reaction was stoppered and stirred for an additional 1 h and then diluted with 50 mL of ether and let sit overnight. The resulting white solid carboxylic acid was collected by filtration and dried in vacuo. Electrospray Mass Spec: 468.1 (M–H)–.

Following the procedure of Example 328, 0.850 g (1.682 mmol) of the carboxylic acid gives 0.693 g of the hydroxamic acid-amine salt as a tan solid. Electrospray Mass Spec: 485.3 (M+H)+.

EXAMPLE 387

N-Hydroxy-2-{(4-methoxy-benzenesulfonyl)-[2-(4-methyl-piperazin-1-yl)-2-oxo-ethyl]-amino}-3-methyl-benzamide Following the procedure of Example 9, 4.0 g (0.011 mol) of the product of Example 330 was reacted with benzyl 2-bromoacetate to give 5.57 g (100%) of the alkylated sulfonamide as a colorless oil. Electrospray Mass Spec: 526.3 (M+H)+.

To a solution of 5.50 g (0.010 mol) of the benzyl ester in 15.0 mL of ethanol was added 3.30 g (0.052 mol) of ammonium formate and 0.550 g of 10% palladium on carbon. The reaction was stirred at room temperature for 18 h and then filtered through celite. The filtrate was concentrated in vacuo, diluted with ethyl acetate, washed with water, dried over MgSO$_4$, filtered and concentrated. The residue was chromatographed on silica gel eluting with EtOAc/hexanes (1:1) to give the carboxylic acid as a white foam. Electrospray Mass Spec: 436.2 (M+H)+.

To a solution of 1.00 g (2.299 mmol) of the carboxylic acid in 10 mL of dichloromethane was added 0.36 mL of DMF followed by 2.3 mL of a 2M solution of oxalyl chloride in dichlcwo thane. The reaction was steeed at room terpeanre for 1 h and then poured into a 0° solution of 1.3 mL (0.011 mmol) of N-methylpiperazine in 10 mL of dichloromethane. The reaction was stirred overnight and then poured into water and extracted with ether. The organics were then washed with water, dried over Na$_2$SO$_4$, filtered and concentrated in vacuo. The residue was chromatographed on silica gel eluting with ethyl acetate to give 1.19 g (100%) of the amide as a colorless oil. Electrospray Mass Spec: 518.4 (M+H)+.

Next, HCl gas was bubbled through a solution of 1.10 g (2.128 mmol) of the amide dissolved in 25 mL of dichloromethane for 10 minutes. The reaction was stopped and stirred for an additional 1 h and then diluted with 50 mL of ether and let sit overnight. The resulting white solid cafroxylic acid was collected by filtration and dried in vacuo. Electrospray Mass Spec: 459.8 (M−H)−.

Following the procedure of Example 328, 0.927 g (1.863 mmol) of the carboxylic acid gives 0.350 g of the hydroxamic acid-amine salt as a white solid. Electrospray Mass Spec: 477.3 (M+H)+.

EXAMPLE 388

N-Hydroxy-2-[(2-hydroxy-ethyl)-(4-methoxy-benzenesulfonyl)-amino]-3-methyl-benzamide Following the procedure of Example 9, 2.0 g (5.97 mmol) of the product of Example 3 was reacd with t-butyl bromoacetate to give 2.38 g (89%) of the alkylated sulfonamide as a colorless oil. Electrospray Mass Spec: 449.9 (M+H)+.

To a solution of 2.20 g (4.90 mmol) of the t-butyl ester in 10 mL of dichloromethane was added 5.0 mL of trifluoroacetic acid. The reaction was stirred at room temperature for 2 h and then concentrated in vacuo. The residue was triturated with ether and the resulting white solid carboxylic acid (1.85 g) was collected by filtration and dried in vacuo. Electrospray Mass Spec: 392.0 (M−H)−.

The acid (1.75 g, 4.45 mmol) was then reduced with borane-THF as in Example 341, to provide 1.21 g of the alcohol as a white solid. Electrospray Mass Spec: 379.9 (M+H)+.

Following the procedure of Example 337, 0.812 g (2.142 mmol) of the alcohol then gives 0.910 g (92%) of the terahydropyranyl ether. This ether-ester is then hydrolyzed following the procedure of Example 19 to give 0.634 g (72%) of the carboxylic acid as a brown glass. Electrospray Mass Spec: 372.2 (M+Na)+.

Following the procedure of Example 328, 0.592 g (1.318 nmuol) of the ether-carboxylate then gives 0.105 g of the hydroxy-hydroxamic acid as a tan solid. Electrospray Mass Spec: 381.1 (M+H)+.

EXAMPLE 389

2-[Benzyl-(4-methoxy-benzenesulfonyl)-amino]-5-dimethyl-amino-N-hydroxy-3-methyl-benzamide To a solution of 0.83 g (1.649 mmol) of the product of Example 11 in 25.0 mL of toluene was added 0.639 (3.627 mmol) of tris(dimethyl-amino)borane, 0.349 (3.627 mmol) of sodium t-butoxide, 0.060 g (0.066 mmol) of tris-(dibenzylideneacetone)-dipalladium and 0.123 (0.198 mmol) of BINAP. The resulting mixture was heated to 80° for 3 h then cooled to room temperature. The reaction was diluted with ether and filtered through Celite. The filtrate was concentrated in vacuo and the residue was chromatographed on silica gel eluting with EtOAc/Hexanes (1:3) to give 0.342 g (44%) of the N,N-dimethyl aniline-ester.

Following the procedure of Example 53 0.356 g (0.761 mmol) of the N,N-dimethyl aniline-ester is hydrolyzed to give 0.170 g (50%) of the carboxylic acid as a white solid. Electrospray Mass Spec: 453.1 (M−H)−.

Following the procedure of Example 369, 0.225 g (0.496 mmol) of the carboxylc acid gives 0.159 g (69%) of the hydroxamic acid-aniline salt as a pale yellow foam. Electrospray Mass Spec: 469.9 (M+H)+.

EXAMPLE 390

2-[Benzyl-(4-methoxy-benzenesulfonyl)-amino]-3-dimethyl-amino-N-hydroxy-benzamide To a solution of 0.100 g (0.219 mmol) of the product of Example 168 in 10 mL of ethanol was added 0.247 g (1.096 mmol) of $SnCl_2$ dihydrate and the reaction mixture was then heated to reflux for 3 h. After cooling to room temperature the reaction was concentreed in vacuo and then diluted with ether. The organics were washed with 1N sodium hydroxide solution and water, dried over $Na_2SO_4$, filtered and concentred in vacuo. The residue was triturated with ether to give 0.060 g of the aniline as a white solid. Electrospray Mass Spec: 426.9 (M+H)+.

To a solution of 0.455 g (1.068 mmol) of the aniline in 10 mL of DMF was added 1.44 g (0.011 mol) of potassium carbonate and 0.66 mL of iodomethane and the reaction was heated to 80° for 18 h. The reaction was then allowed to cool to room temperature and diluted with ether. The organics were washed with water, dried over $Na_2SO_4$, filtered and concentrated in vacuo. The residue was chromatographed on silica gel eluting with EtOAc/hexanes (1:3) to give 0.44 g (91%) of the N,N-dimethyl aniline-ester as a pink oil. Electrospray Mass Spec: 454.9 (M+H)+.

Following the procedure of Example 53, 0.388 g (0.855 mmnol) of the N,N-dimethyl aniline-ester gives 0.314 g (82%) of the N,N-dimethyl aniline-arboxylate as a white foam. Electrospray Mass Spec: 439.0 (M−H)−.

Following the procedure of Example 369, 0.251 g (0.563 mmol) of the carboxylate gives 0.226 g (88%) of the hydroxamic acid as a pink foam. Electrospray Mass Spec: 455.9 (M+H)+.

EXAMPLE 391

4-(2-Piperidin-1-yl-ethoxy)-benzyl chloride

To a stirred solution of 4-hydroxy benzaldehyde (12.2 gm, 0.1 mol) and K2CO3 (25 gm, excess) in N,N-dimethlformamide (250 ml) was added 1-(2-chloroethyl) piperidine monohydrochloride (20.0 gm, 1.08 mol). The reaction mixture was heated to 80° C. for 24 hrs and cooled to room temperature. The reaction mixture was quenched with ice cold water and extracted with chloroform. The organics were washed with water, dried over anhydrous $MgSO_4$, filtered and concentrated in vacuo. The residue was dissolved in methanol and sodium borohydride (10 gms, excess) was slowly added at 0° C. The reaction mixture was stirred at room temperature for 2 h and then quenched with water. The alcohol was extracte with chloroform, the organics were washed well with water, dried over $Na_2SO_4$, filtered and concentrated in vacuo.

The crude alcohol thus obtained was dissolved in THF (200 ml) and HCl gas was passed through for 30 minutes at 0° C. To the suspension of hydrochloride thus obtained, thionyl chloride (30 ml, excess) was slowly added. The reaction mixture was refluxed for thirty minutes and cooled to room temperature. The reaction mixture was then concentrated to dryness and triturated with anhydrous ether. The precipitated solid was filtered and dried under vacuum at room temperature to give 25 g (86%) of the product as a white solid. m.p. 145–148° C. Electrospray Mass Spec: 256 (M+H).

EXAMPLE 392

4-(2-N,N-Diethyl-ethoxy)-benzyl chloride

To a stirred solution of 4-hydroxy benzaldehyde (12.2 gm, 0.1 mol) and $K_2CO_3$ (25 gm, excess) in N,N- diethlformamide (250 ml) was added 2-diethyl-aminoethyl chloride monohydrochloride (20.0 gm, 1.2 mol). The reaction mixture was heated at 80° C. for 24 hrs and cooled to room temperature. The reaction mixture was quenched with ice cold water and extracted with chloroform. The organics were washed with water, dried over anhydrous $MgSO_4$, filtered and concentrated in vacuo. The residue was dissolved in methanol and sodium borohydride (10 gms, excess) was slowly added at 0° C. The reaction mixture was stirred at room temperature for 2 h and then quenched with water. The alcohol was extracted with chloroform, washed well with water, dried, filtered and concentrated in vacuo.

The crude alcohol thus obtined was dissolved in ThF (200 ml) and HCl gas was passed through for 30 minutes at 0° C. To the suspension of hydrochloride thus obtained, thionyl chloride (30 ml, excess) was slowly added. The reaction mixture was refluxed for thirty minutes and cooled to room temperature. The reaction mixture was then concentrated to dryness and triturated with anhydrous ether. The precipitated solid was filtered and dried under vacuum at room temperature to give 18 g (65%) of the product as a white solid, m.p. 76–79° C. Electrospray Mass Spec: 244 (M+H).

EXAMPLE 393

N-Hydroxy-2-[[(4-methoxyphenyl)sulfonyl][[4-[2-(1-piperidinyl)ethoxy]phenyl]methyl]amino]-3-methylbenzamide Following the procedure of Example 45, 1.00 g (2.985 mmol) of the product of Example 3 reacts with 0.952 g (3.284 mmol) of the product of Example 391 to give 0.965 g (58%) of the piperidine-ester as a colorless oil. Electrospray Mass Spec: 553.5 (M+H)+.

Following the procedure of Example 319, 0.889 g (1.611 mmol) of the ester gives 0.872 g of the carboxylic acid as a white foam. Electrospray Mass Spec: 539.2 (M+H)+.

Following the procedure for Example 328, 0.814 g (1.513 mmol) of the carboxylic acid gives 0.179 g of the hydroxamate-amine salt as a white solid. Electrospray Mass Spec: 554.5 (M+H)+.

EXAMPLE 394

2-[[4-(2-Diethylamino-ethoxy)-benzyl]-(4-methoxy-benzenesulfonyl)-amino]-N-hydroxy-3-methyl-benzamide Following the procedure of Example 45, 1.00 g (2.653 mmol) of the product of Example 30 rtacts with 0.811 g (2.918 mmol) of the product of Example 392 to give 0.575 g (37%) of the pipeidine-ester as a tan foam. Electrospray Mass Spec: 583.1 (M+H)+.

Following the procedure of Exanple 374, 0.539 g (0.926 mmol) of the ester gives 0.369 g of the carboxylic acid as a white solid. Electrospray Mass Spec: 525.2 (M–H)–.

Following the procedure for Example 369, 0.328 g (0.513 mmol) of the caxboxylic acid gives 0.194 g of the hydroxamate-amine salt as a white solid. Electrospray Mass Spec: 542.3 (M+H)+.

EXAMPLE 395

5-Bromo-N-hydroxy-2-{(4-methoxy-benzenesulfonyl)-[4-(2piperidin-1-yl-ethoxy)-benzyl]-amino}-3-methyl-benzamide Following the procedures for Example 393, 1.00 g (2.415 nmol) of the product of Example 202 gives 0.470 g of the hydroxamate-amine salt as a pale yellow solid. Electrosray Mass Spec: 632.2 (M+H)+.

EXAMPLE 396

N-Hydroxy-2-[[(4-methoxyphenyl)sulfonyl][[4-[[2-(1-piperidinyl)ethyl]amino]carbonyl]phenyl]methyl]amino]-3-methylbenzambide Following the procedure of Example 9, 1.00 g (2.653 mmol) of the product of Example 330 reacts with 0.851 g (3.714 numol) of para-carbomethoxy benzyl bromide to give 1.30 g (94%) of the benzylated sulfonamide-ester as a white foam. Electrospray Mass Spec: 526.4 (M+H)+.

To a solution of 0.1.249 g (2.379 mmol) of the ester in 24.0 mL of THF/MeOH (1:1) was added 12 mL of 1N sodium hydroxide solution and the reaction was stirred for 3 h at room temperature. The reaction was then acidified and ex=aWd with ethyl acetate. The combined organics were dried over $MgSO_4$, filtered and concentrated in vacuo to give 0.1.08 g (89%) of the carboxylic acid as a white foam. Electrospray Mass Spec: 512.3 (M+H)+.

To a solution of 1.01 g (1.977 mmol) of the carboxylic acid in 10 mL of dichloromethane was added 0.306 mL of DMF followed by 2.0 mL of a 2M solution of oxalyl chloride in dichloromethane. The reaction was stirred at room temperatre for 1 h and then poured into a 0° C. solution of 0.56 mL (3.95 mmol) of aminoethyl piperidine and 0.825 mL of triethylamine in 7 mL of dichloromethane. The reaction was stired overnight and then poured into water and extracted with ether. The organics were then washed with water, dried over $Na_2SO_4$, filtered and concentrated in vacuo to give 1.23 g (100(%) of the amide as a white foarm Electrospray Mass Spec: 622.6 (M+H)+.

Next, HCl gas was bubbled through a solution of 1.167 g (1.879 mmol) of the amide dissolved in 20 mL of dichloromethane for 10 minutes. The reaction was stopped and stirred for an additional 1 h and then diluted with 50 mL of ether and let sit overnight. The resulting white solid carboxylic acid was collected by filtration and dried in vacuo. Electrospray Mass Spec: 566.6 (M+H)+.

Following the procedure of Example 328, 1.023 g (1.704 nunol) of the carboxylic acid gives 0.177 g of the hydroxamate-amine salt as a white solid. Electrospray Mass Spec: 581.0 (M+H)+.

EXAMPLE 397

4-[(4-Methoxy-benzenesulfonyl)-pyridin-3-ylmethyl-amino]-5-methyl-biphenyl-3-carboxylic acid hydroxyamide hydrochloride salt Following the procedure of Example 241 the product of Example 89 reacts with phenylboronic acid to give the corresponding biaryl-sulfonamide-ester. The ester is subsequendy hydrolyzed to the carboxylic acid following the procedure of Example 319 and then converted into the hydroxamic acid hydrochloride salt following the method of Example. 369. Electrospray Mass Spec: 504.5 (M+H)+.

EXAMPLE 398

N-Hydroxy-2-[(4-methoxy-benzenesulfonyl)-pyridin-3-ylmethyl-amino]-3-methyl-5-thiophen-3-yl-benzamide hydrochloride salt Following the procedure of Example 241 the product of Example 89 reacts with thiophene-3-boronic acid to give the corresponding biaryl-sulfonamide-ester. The ester is subsequently hydrolyzed to the carboxylic acid following the procedure of Example 319 and then converted into the hydroxamic acid hydrochloride salt following the method of Example 369. Electrospray Mass Spec: 508.1 (M–H)–

EXAMPLE 399

4"-Methoxy-4-[(4-methoxy-benzenesulfonyl)-pyridin-3-ylmethyl-amino]-5-methyl-[1,1';4',1"]terphenyl-3-carboxylic acid hydroxyamide hydrochloride salt Following the procedure of Example 241 the product of Example 89 reacts with 4-(4'-methoxyphenyl)phenylboronic acid to give the corresponding biaryl-sulfonamide-ester. The ester is subsequently hydrolyzed to the carboxylic acid following the procedure of Example 319 and then converted into the hydroxamic acid hydrochloride salt following the method of Example 369. Electrospray Mass Spec: 609.9 (M+H)+.

EXAMPLE 400

4-[(4-Methoxy-benzenesulfonyl)-pyridin-3-ylmethyl-amino]-5-methyl-3'-nitro-biphenyl-3-carboxylic acid hydroxyamide hydrochloride salt Following the procedure of Example 241 the product of Example 89 reacts with 3-nitrobenzeneboronic acid to give the corresponding biaryl-sulfonamide-ester. The ester is subsequently hydrolyzed to the carboxylic acid following the procedure of Example 319 and then converted into the hydroxamic acid hydrochloride salt following the method of Example 369. Electrospray Mass Spec: 549.1 (M+H)+

EXAMPLE 401

4'-Methoxy-4-[(4-methoxy-benzenesulfonyl)-pyridin-3-ylmethyl-amino]-5-methyl-biphenyl-3-carboxylic acid hydroxyamide hydrochloride salt Following the procedure of Example 241 the product of Example 89 reacts with 4 methoxybenzeneboronic acid to give the corresponding biaryl-sulfonamnide-ester. The ester is subsequently hydrolyzed to the carboxylic acid following the procedure of Example 319 and then converted into the hydroxamic acid hydrochloride salt following the method of Example 369. Electrospray Mass Spec: 534.1 (M+H)+

EXAMPLE 402

5-Benzo[b]thiophen-2-yl-N-hydroxy-2-[(4-methoxy-benzenesulfonyl)-pyridin-3-ylmethyl-amino]-3-methyl-benzamide hydrochloride salt Following the procedure of Example 241 the product of Example 89 reacts with benzo[b]thiophene-2-boronic acid to give the corresponding biaryl-sulfonamide-ester. The ester is subsequently hydrolyzed to the carboxylic acid following the procedure of Example 319 and then converted into the hydroxamic acid hydrochloride salt following the method of Example 369. Electrospray Mass Spec: 560.1 (M+H)+

EXAMPLE 403

5-Benzo[b]furaphen-2-yl-N-hydroxy-2-[(4-methoxy-benzenesulfonyl)-pyridin-3-ylmethyl-amino]-3-methyl benzamide hydrochloride salt Following the procedure of Example 241 the product of Example 89 reacts with benzo[b]furan-2-boronic acid to give the corresponding biaryl-sulfonamide-ester. The ester is subsequently hydrolyzed to the carboxylic acid following the procedure of Example 319 and then converted into the hydroxamic acid hydrochloride salt following the method of Example 369. Electrospray Mass Spec: 544.3 (M+H)+

Example 404

4-[(4-Methoxy-benzenesulfonyl)-pyridin-3-ylmethyl-amino]-5-methyl-4'-trifluoromethoxy-biphenyl-3-carboxylic acid hydroxyamide hydrochloride salt Following the procedure of Example 241 the product of Example 89 reacts with 4-trifluoromethoxybenzeneboronic acid to give the corresponding biaryl-sulfonamide-ester. The ester is subsequently hydrolyzed to the carboxylic acid following the procedure of Example 319 and then converted into the hydroxamic acid hydrochloride salt following the method of Example 369. Electrospray Mass Spec: 588.1 (M+H)+

EXAMPLE 405

5-Benzo[1,3]dioxol-5-yl-N-hydroxy-2-[(4-methoxy-benzenesulfonyl)-pyridin-3-ylmethyl-amino]-3-methyl-benzamide hydrochloride salt Following the procedure of Example 241 the product of Example 89 reacts with 3,4-methylenedioxybenzeneboronic acid to give the corresponding biaryl-sulfonamide/ester. The ester is subsequently hydrolyzed to the carboxylic acid following the procedure of Example 319 and then converted into the hydroxamic acid hydrochloride salt following the method of Example 369. Electrospray Mass Spec: 548.1 (M+H)+

EXAMPLEI 406

4-[(4-Methoxy-benzenesulfonyl)-pyridin-3-ylmethyl-amino]-5-methyl-3'-trifluoromethyl-biphenyl-3-carboxylic acid hydroxyamide hydrochloride salt Following the procedure of Example 241 the product of Example 89 reacts with 3-trifluoromethylbenzeneboronic acid to give the corresponding biaryl-sulfonanide-cter. The ester is subsequently hydrolyzed to the carboxylic acid following the procedure of Example 319 and then converted into the hydroxamic acid hydrochloride salt following the method of Example 369. Electrospray Mass Spec: 572.0 (M+H)+.

EXAMPLE 407

2-[(4-Chloro-benzyl)-(5-pyridin-2-yl-thiophene-2-sulfonyl)-amino]-N-hydroxy-3-methyl-benzamide A mixture of Wang resin (Wang, S. J. Am. Chem. Soc. 1973, 95, 1328–1333) (Advanced ChemTech 200–400 mesh, 1% crosslinked; loading: 0.92 mmol/g; 15.0 g, 0.011 mol), LiCl (1.4 g, 0.033 mol) and DMF (150 mL) was magnetically stired for 40 min. Collidine (4.0 g, 0.033 mol) was added and the mixture was cooled (0–5° C.) with an ice bath. Methanesulfonyl chloride (3.8 g, 0.033 mol) was added over 5 min. After 10 min. the cooling bath was removed and stirring was continued for 68 h. The mixture was filtaed and the resin was washed with DMF (250 mL), 30% $H_2O$/DMF ((2×300 mL), DMF (2×250 mL), EtOH (3×250 mL), $CH_2Cl_2$ (3×300 mL), and hexane (2×250 mL).

The resin was dried over $P_2O_5$ in vacuo to give 14.3 g; $^{13}$C NMR (CDCl$_3$) δ 46.22 (CH$_2$Cl); IR (KBr) cm$^{-1}$: 2900, 1600, 1520, 1485, 1450.

A mixture of chloWang resin (1.13 mmol/g, 1 g), NaI (169 mg, 1.13 mmol), Cs$_2$CO$_3$ (1.11 g, 3.39 mmol) and N-hydroxyphthalimide (922 mg, 5.65 mmol) in DMF was heated at 50° C. for 16 h. After filtration, the resin was washed with DMF/H$_2$O (3:2, 4×25 mL), DMF/H$_2$O (9:1, 4×25 mL), DMF (2×25 mL), dichloromethane (3×25 mL) and MEOH (2×20 mL). The resin was then dried under vacuum to give the product resin (1.1 g, 96%). N% theory 1.38%, found 1.09%.

Phthalimido hydroxylamine resin (10 g) was treated with a mixture of THF/EtOH/NH$_2$NH$_2$ (80 mL/80 mL/26 mL) for 18 h at room temperature. The mixture was filtered and the resin was washed with MeOH (200 mL), DMF (200 mL), and the process was repeated. The resin was then washed with MeOH (200 mL) and dichloromethane (2×150 mL). Finally the resin was dried under vacuum.

A cold (−5° C., ice-salt bath) solution of 2-amino-3methylbenzoic acid (1.51 g, 10 mmol) and pentafluorophenol (2 g, 11 mmol) in dry DMF (2 mL) was treated with a solution of DCC (2.27 g, 11 mmol) in EtOAc (20 mL). The reaction mixture was stored at 0° C. overnight. The precipitate was removed by filtration and washed with EtOAc (~10 mL). The washings were combined with the filtrate and washed with 5% aqueous NaHCO$_3$ (2×15 mL), H$_2$O (15 mL) and dried (Na$_2$SO$_4$). The solvent was removed to give the product (3.2 g, 100%) as a solid.

To a suspension of hydroxylamine on Wang resin (3.05 g, 1.13 mmol/g) in DMF was added a solution of pentafluorophenyl 2-amino-3-methylbenzoate (4.37 g, 13.8 mmol) followed by 4-dimethylarinopyridine (2.1 g, 17.2 mmol). The resultant mixture was shaken at room tempertue for 40 h. The resin was filtered and washed with DMF (4×100 ml), dichloromethane (3×80 mL), MeOH (2×80 mL), and dichloromethane (4×80 mL). Finally the resin was dried under vacum to give product resin (3.51 g, 100%).

To a suspension of 2-amino-3-methylbenzoic acid hydroxyamide on Wang resin (3.51 g, 0.98 mmol/g) in dichloromethane (20 mL) was added pyridine (2.78 mL, 34.4 mmol). After 5 min, a solution of 5-(pyridin-2-yl) thiophen-2-yl-sulfonyl chloride (4.46 g, 17.2 mmol) in dichloromethane (15 mL) was added to the reaction mixture. The resultant suspension was shaken at room temperature for 24 h. The resin was filtered and washed with DMF (4×40 mL), dichloromethane (3×40 mL), MeOH (2×40 mL) and dichlncthane (4×40 mL), and dried under vacum to give 4.25 g (97%) of product resin.

To confirm the completion of the reaction, a sample of resin (100 mg) was suspended in TFA/dichloromethane (1:1,2 mL) and allowed to sit for 1 h. The resin was filtered and washed with dichloromethane (2×1.5 mL). The combined filtrates were evaporated to dryness to give 24.7 mg of product, (5-pyridin-2-yl-thiophene-2-sulfonyl)-amino]-N-hydroxy-3-methyl-benzamide on Wang Resin. Mass Spec: expected 389.0504, found 389.9.

To a suspension of (5-pyridin-2-yl-thiophene-2-sulfonyl)-amino]-N-hydroxy-3-methyl-benzamide on Wang resin (100 mg, 0.84 mmol/g) in a solution of 4chlorobenzyl alcohol (0.485 mmol) in ThF (1 mL) was added a solution of triphenylphosphine (0.485 mmol) and diethyl azodicarboxylate (0.485 mmol) in THF (1.24 mL). The resultant mixture was shaken for 4 h at room temperature. The resin was filtered, washed with THF (4×3 mL) and dichloromethane (4×3 mL), and dried under vacuum. The resin was suspended in trifluoroacetic acid/dichloromethane (1:1, 2 mL) and allowed to sit for 1 h. The resin was filtered and washed with dichloromethane (2×1.5 mL). The combined filtrates were evaporated to dryness, and the crude product was purified on a solid phase exton cartridge (reverse phase) to give 16.7 mg of product, 2-[(4-chloro-benzyl)-(5-pyridin-2-yl-thiophene-2-sulfonyl)-amino]-N-hydroxy-3-methyl-benzamide. mass Spec: Spec: expected 513.0584, found 513.8.

EXAMPLE 408

2-[(3,4-Dimethyl-benzyl)-(5-pyridin-2-yl-thiophene-2-sulfonyl)-amino]-N-hydroxy-3-methyl-benzamide To a suspension of (5-pyridin-2-yl-thiophene-2-sulfonyl)-amino]-N-hydroxy-3-methyl-benzamide on Wang resin, the product of Example 407 (100 mg, 0.84 mmol/g), in a solution of 3,4 dimethylbenzyl alcohol (0.485 mmol) in THF (1 mL) was added a solution of triphenylphosphine (0.485 mmol) and diethyl azodicarboxylate (0.485 mmol) in THF (1.24 mL). The resultant mixture was shaken for 4 h at room temperature. The resin was filtered, washed with THF (4×3 mL) and dichloromethane (4×3 mL), and dried under vacuum. The resin was suspended in trifluoroacetic acid/dichloromethane (1:1, 2 mL) and allowed to sit for 1 h. The resin was filtered and washed with DCM (2×1.5 mL). The combined filtrates were evaporated to dryness, and the crude product was purified on a solid phase extraction cartridge (reverse phase) to give 18.1 mg of product Mass Spec: expected 507.1286, found 507.9.

EXAMPLE 409

2-[(4-Bromo-benzenesulfonyl)-pyridin-3-ylmethyl-amino]-3-methyl-benzoic acid methyl ester Following the procedure of Example 1, methyl-3-methyl anthranilate reacts with p-bromobenzenesulfonyl chloride to provide the aryl sulfonamide as a white powder. Electrospray Mass Spec: 475 (M+H)+.

EXAMPLE 410

N-Hydroxy-3-methyl-2-[pyridin-3-ylmethyl-(4'-trifluoromethyl-biphenyl-4-sulfonyl)-amino]-benzamide Following the procedure of Example 241, the product of Example 409 is converted into the biaryl sulfonamide-ester. Hydrolysis of the ester according to the procedure of Example 190 gives the corresponding carboxylic acid. The carboxylic acid is then converted into the hydroxamic acid, isolated as an off-white powder, according to the procedure of Example 68. Electrospray Mass Spec: 542.1 (M+H)+.

EXAMPLE 411

2-[(2',4'-Dimethoxy-biphenyl-4-sulfonyl)-pyridin-3-ylmethyl-amino]-N-hydroxy-3-methyl-benzamide Following the procedure of Example 241, the product of Example 409 is converted into the biaryl sulfonamide-ester. Hydrolysis of the ester according to the procedure of Example 190 gives the corresponding carboxylic acid. The carboxylic acid is teen converted into the hydroxamic acid, isolated as an off-white powder, according to the procedure of Example 68. Electrospray Mass Spec: 534.0 (M+H)+.

EXAMPLE 412

N-Hydroxy-3-methyl-2-[pyridin-3-ylmethyl-(4-thiophen-2-yl-benzenesulfonyl)-amino]-benzamide Following the procedure of Example 241, the product of Example 409 is converted into the bivyl sulfonamide-ester.

Hydrolysis of the ester according to the procedure of Example 190 gives the corresponding carboxylic acid. The carboxylic acid is then converted ihto the hydroxamic acid, isolated as an off-white powder, according to the procedure of Example 68. Electrospray Mass Spec: 480.3 (M+H)+.

EXAMPLE 413

2-[(4-Ethynyl-benzenesulfonyl)-pyridin-3-ylmethyl-amino]-N-hydroxy-3-methyl-benzamide Following the procedure of Examnple 78 the product of Example 409 is converted into the alkynl-aryl sulfonamide-ester. Hydrolysis of the ester according to the procedure of Example 190 gives the corresponding carboxylic acid. The carboxylic acid is then converted into the hydroxamic acid, isolated as an off-white powder, according to the procedure of Example 68. Electrospray Mass Spec: 422.3 (M+H)+.

EXAMPLE 414

2-[(4-Benzo[b]thiophen-2-yl-benzenesulfonyl)-pyridin-3-ylmethyl-amino]-N-hydroxy-3-methyl-benzamide Following the procedure of Example 241, the product of Example 409 is converted into the biaryl sulfonamide-ester. Hydrolysis of the ester according to the procedure of Example 190 gives the corresponding carboxylic acid. The carboxylic acid is then converted into the hydroxamic acid, isolated as an off-white powder, according to the procedure of Example 68. Electrospray Mass Spec: 530.0 (M+H)+.

EXAMPLE 415

2-[(4-Benzo[1,3]dioxol-5-yl-benzenesulfonyl)-pyridin-3-ylmethyl-amino]-N-hydroxy-3-methyl-benzamide Following the procedure of Example 241, the product of Example 409 is converted into the biaryl sulfonamide-ester. Hydrolysis of the ester according to the procedure of Example 190 gives the corresponding carboxylic acid. The carboxylic acid is then converted into the hydroxamic acid, isolated as an off-white powder, according to the procedure of Example 68. Electrospray Mass Spec: 518 (M+H)+.

EXAMPLE 416

3-Methyl-2-[4-(pyidin-4-yloxy)-benzensulfonylamino]-N-hydroxy-benzoic acid methyl ester Following the procedure of Example 1, the product of Example 3 reacts with 4-[(pyrid-4-yl)oxy]benzenesulfonyl chloride hydrochloride to provide the NH-sulfonamide as a white powder. Electrospray Mass Spec: 399 (M+H)+.

EXAMPLE 417

3-Methyl-2-[4-(pyridin-4-yloxy)-benzensulfonylamino]-N-hydroxy-benzamide

Following the procedure of Example 9, the NH-sulfonamide product of Example 416 reacs with iodomethane to provide the N-methyl sulfonamide-ester.

Hydrolysis of the ester according to the procedure of Example 190 gives the corresponding carboxylic acid. The carboxylic acid is then converted into the hydroxamic acid, isolated as a white powder, according to the procedure of Example 68. Electropray Mass Spec: 414 (M+H)+.

Pharmacology

Procedures for Measuring MMP-1, MMP-9, and MMP-13 Inhibition

These assays are based on the cleavage of a thiopeptide substrates such as Ac-Pro-Leu-Gly(2-mercapto-4-methyl-pentanoyl)-Leu-Gly-OEt by the matrix metalloproteinases MMP-1, MMP-13 (collagenases) or MMP-9 (gelatinase), which results in the release of a substrate product that reacts coloimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with assay buffer (50 mM HEPES, pH 7.5, 5 mM $CaCl_2$, 0.02% Brij) to the desired final concentration. The assay buffer, enzyme, vehicle or inhibitor, and DThB/substrate are added in this order to a 96 well plate (total reaction volume of 200 $\mu$l) and the increase in color is monitored spectiophotometrically for 5 minutes at 405 nm on a plate reader and the increase in color over time is plotted as a linear line.

Alternatively, a fluorescent peptide substrate is used. In this assay, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM $Ca^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide assays, the slope of the line is calculated and represents the reaction rate. The linearity of the reaction rate is confirmed ($r^2>0.85$). The mean (x±sem) of the control rate is calculated and compared for statistical significance ($p<0.05$) with drug-treated rates using Dunnett's multiple comparison test. Dose-response relationships can be generated using multiple doses of drug and $IC_{50}$ values with 95% CI are estimated using linear regression.

In vivo MMP Inhibition

A 2 cm piece of dialysis tubing (molecular weight cut-off 12–14,000, 10 mm flat width) containing matrix metallo-proteinase enzyme (stromelysin, coflagenase or gelatnase in 0.5 mL of buffer) is implanted either ip or sc (in the back) of a rat (Sprague-Dawley, 150–200 g) or mouse (CD-1, 2514 50 g) under anesthesia. Drugs are administered PO, IP, SC or IV through a canula in the jugular vein. Drugs are administered in a dose volume of 0.1 to 0.25 mL/animal. Contents of the dialysis tubing is collected and enzyme activity assayed.

Enzyme reaction rates for each dialysis tube are calculated. Tubes from at least 3 different animals are used to calculate the meani sem. Statistical significance ($p<0.05$) of vehicle-treated animals versus drug-treated animals is determined by analysis of variance. (*Agents and Actions* 21: 331, 1987).

Procedure for Measuring TACE Inhibition

Using 96-well black microtiter plates, each well receives a solution composed of 10 $\mu$L TACE (Immunex, final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confined ($r^2 > 0.85$). The mean (x±sem) of the control rate is calculated and compared for statistical significance (p<0.05) with drug-treated rates using Dunnert's multiple comparison test. Dose-response relationships can be generate using multiple doses of drug and $IC_{50}$ values with 95% CI are estimated using linear regression.

Results of the above in-vitro and in-vivo matrix metalloproteinase inhibition and TACE inhibition phamalogical assays are given in Table I below.

TABLE I

Inhibition of MMP and TACE

| Example | MMP-1[1] | MMP-9[1] | MMP-13[1] | in-vivo MMP[2] | TACE[1] |
|---|---|---|---|---|---|
| 23 | 639 | 650 | 555 | | >1000 |
| 24 | 398 | 31 | | | 1000 |
| 25 | | | | 32%(100), ip | >1000 |
| 26 | 884 | 346 | 982 | | >1000 |
| 27 | 1573 | 440 | 717 | | >1000 |
| 28 | 115 | 23 | 50 | | 460 |
| 29 | 553 | 353 | 728 | | 1000 |
| 34 | 281 | 28 | 69 | 31.6(100), ip | >1000 |
| 54 | 24 | 3 | 4 | | |
| 55 | 670 | 29 | 216 | | >1000 |
| 56 | >1000 | 57 | 138 | | >1000 |
| 57 | >500 | 12 | 33 | | 1000 |
| 58 | 244 | 5 | 36 | | 682 |
| 59 | 242 | 8 | 34 | | >1000 |
| 60 | 152 | 7 | 15 | | 232 |
| 61 | | 34 | 33 | 46(20), po 59(50), po | 289 |
| 68 | 82 | 21 | 15 | | 239 |
| 69 | 153 | 874 | 1370 | | >1000 |
| 72 | >1000 | 144 | 137 | | 377 |
| 74 | >1000 | 554 | 959 | | 429 |
| 77 | | 131 | | | |
| 80 | 109 | 21 | 18 | | 134 |
| 83 | | 34 | 32 | | |
| 85 | | 663 | | | >1000 |
| 88 | 132 | 15 | 11 | | 50 |
| 91 | | 24 | 20 | 55(100), po | |
| 94 | 1000 | 276 | 209 | | >1000 |
| 101 | 267 | 23 | 138 | | 422 |
| 102 | 314 | 29 | | | 162 |
| 115 | >1000 | 11 | 20 | | 173 |
| 116 | 201 | 13 | 14 | | 271 |
| 117 | 114 | 10 | 10 | 28.3(100), ip | 154 |
| 118 | 248 | 345 | 229 | | >1000 |
| 119 | 223 | 27 | 14 | | 252 |
| 120 | 238 | 18 | 39 | | 310 |
| 125 | >1000 | 27 | 134 | | 300 |
| 130 | 213 | 4 | 13 | | 76 |
| 131 | 212 | 54 | 48 | | 80 |
| 138 | 258 | 77 | 57 | | 215 |
| 145 | 55 | 7 | 3 | | 158 |
| 150 | 213 | 4 | 13 | | 76 |
| 151 | 212 | 54 | 48 | | 80 |
| 156 | >1000 | 104 | 134 | | |
| 158 | >1000 | 11 | 62 | | |
| 165 | | 286 | 350 | | |
| 166 | | 203 | >300 | | |
| 167 | | 42 | 178 | | |
| 170 | 347 | 12 | 39 | | 176 |
| 174 | 323 | 16 | 71 | | 50% |
| 175 | 90 | 7 | 4 | | 57 |
| 179 | 680 | 40 | 53 | | 64% |
| 186 | 37 | 13 | 1.4 | | 61 |
| 191 | 1239 | 10 | 67 | | 210 |
| 194 | 306 | | 12 | | 154 |
| 197 | 711 | 5 | 6 | | 32% |
| 201 | 104 | 11 | 27 | | 1000 |
| 207 | 1117 | 2.0 | 2.5 | | 375 |
| 212 | 415 | 5.2 | 11 | | 314 |
| 214 | 423 | 6.4 | 19 | | 232 |
| 219 | 290 | 6.7 | 5.8 | | 548 |
| 224 | 957 | 11 | 14 | | 715 |
| 227 | 193 | 3.1 | 4.1 | | 446 |
| 230 | 20 | 2.4 | 1.9 | | 47%(1) |
| 233 | 32 | 2.3 | 1.8 | | 450 |
| 240 | 86 | 3.5 | 1.6 | | 548 |
| 243 | 528 | 6.6 | 3.1 | | 66 |
| 246 | 106 | 6.0 | 3.6 | | 56 |
| 249 | 231 | 2.8 | 6.0 | | 100 |
| 252 | 652 | 15 | 10 | | 346 |
| 255 | 48 | 7.1 | 3.2 | | 65 |
| 258 | 169 | 8.0 | 7.0 | | 110 |
| 261 | 247 | 1.3 | 2.8 | | 54 |
| 264 | 159 | 3.7 | 6.4 | | 77 |
| 267 | 59 | 3.0 | 13 | | 136 |
| 272 | 66 | 0.5 | 6.0 | | 311 |
| 277 | 56 | 4.0 | 4.0 | | 34 |
| 282 | 1050 | 5.0 | 113 | | 44%(1) |
| 285 | 312 | 6.0 | 9.8 | | 61 |
| 292 | 184 | 8.0 | 29 | | 7%(1) |
| 297 | 297 | 9.0 | 14 | | 58%(1) |
| 301 | 211 | 6.9 | 8.7 | | 1484 |
| 302 | 291 | | 24 | | 173 |
| 303 | 2782 | 64 | 104 | | 218%(1) |
| 304 | 4100 | | 305 | | 25%(1) |
| 308 | 10%(1) | 45%(1) | 36%(1) | | 285 |
| 309 | 608 | 5 | 14 | | 174 |
| 310 | 4800 | 21 | 101 | | 154 |
| 311 | 781 | 10 | 43 | | 157 |
| 313 | 180 | 1.4 | 6.3 | | 26 |
| 314 | 954 | 8.4 | 13 | | 27 |
| 320 | 2188 | 46 | 150 | | 142 |
| 325 | 15%(1) | 49%(1) | 60%(1) | | 1640 |
| 325 | 20 | 2.4 | 1.9 | | 47%(1) |
| 328 | 326 | 4.9 | 13 | | 263 |
| 329 | 319 | 6.1 | 23 | | 173 |
| 339 | 216 | 5.2 | 5.7 | | 564 |
| 340 | 522 | 11 | 30 | | 110 |
| 344 | 1173 | 69 | 320 | | 529 |
| 345 | 1158 | 31 | 134 | | 523 |
| 349 | 396 | 8 | 9 | | 32 |
| 350 | 450 | 5 | 21 | | 373 |
| 353 | 23%(1) | 61 | 141 | | 780 |
| 355 | 701 | 28 | 20 | | 288 |
| 358 | 25%(10) | 101 | 107 | | 1054 |
| 360 | 14%(10) | 525 | 1260 | | 1405 |
| 363 | 449 | 20 | 54 | | 137 |
| 367 | 597 | 12 | 13 | | 2700 |
| 369 | 207 | 6.4 | 3.8 | | 38 |
| 373 | 1280 | 26 | 59 | | 539 |
| 374 | 56%(10) | 36%(1) | 17%(1) | | 29%(1) |
| 375 | 329 | 7.1 | 18 | | 356 |
| 376 | 391 | 8.4 | 18 | | 645 |
| 377 | 123 | 4.7 | 15 | | 258 |
| 378 | 213 | 2.9 | 11 | | 243 |
| 381 | 470 | 11 | 19 | | 218 |
| 382 | 142 | 6.5 | 20 | | 146 |
| 383 | 34%(1) | 87%(1) | 48%(1) | | 45%(1) |
| 384 | 48%(1) | 52%(1) | 61%(1) | | 55%(1) |

TABLE I-continued

Inhibition of MMP and TACE

| Example | MMP-1[1] | MMP-9[1] | MMP-13[1] | in-vivo MMP[2] | TACE[1] |
|---|---|---|---|---|---|
| 385 | 25%(1) | 65%(1) | 66%(1) | | 56%(1) |
| 386 | 21%(1) | 16%(.1) | 11%(.1) | | 46%(1) |
| 387 | 2715 | 96 | 307 | | 38%(1) |
| 388 | 66%(10) | 47%(1) | 39%(1) | | 35%(1) |
| 389 | 63 | 2 | 39 | | 633 |
| 390 | 19%(1) | 64 | 531 | | 39%(1) |
| 393 | 176 | 6.9 | 56 | | 277 |
| 394 | 96 | 2.3 | 8.8 | | 215 |
| 395 | 35 | 2.3 | 3.1 | | 108 |
| 396 | 184 | 6.3 | 35 | | 363 |
| 397 | 195 | 3.0 | 3.7 | | 64 |
| 398 | 85 | 2.0 | 3.7 | | 56 |
| 399 | 2197 | 45 | 41 | | 25%(1) |
| 400 | 295 | 6.0 | 4.9 | | 231 |
| 401 | 176 | 1.4 | 2.8 | | 146 |
| 402 | 543 | 2.6 | 8.5 | | 639 |
| 404 | 1800 | 5.9 | 9.5 | | 54%(1) |
| 405 | 176 | 4.1 | 5.8 | | 151 |
| 406 | 542 | 1.1 | 1.6 | | 294 |
| 407 | 1690 | 199 | 35 | | |
| 408 | 3450 | 731 | 148 | | |
| 410 | 47%(10) | 28%(1) | 40%(.1) | | 2%(1) |
| 411 | 32%(10) | 39%(1) | 44%(1) | | 9%(1) |
| 412 | 69%(10) | 44%(1) | 42%(.1) | | 3%(1) |
| 413 | 529 | 55 | 75 | | 43%(1) |
| 414 | 29%(10) | 68%(1) | 38 | | 6%(1) |
| 415 | 37%(10) | 43%(1) | 26 | | 9%(1) |
| 417 | 3245 | 6.8 | 3.7 | | |

[1]$IC_{50}$ nM or % inhibition at 1 $\mu$M concentration
[2]% inhibition vs. MMP-9(dose, mg/kg), ip = intraperitoneal, po = oral Cartilage Degradation in the Rat Twenty mg slices of cartilage are obtained from the knee of freshly slaughtered cattle. Discs of cellulose sponge, 6 mm in diameter, are cut and a 2 mm hole put in the center of the sponge. 100 $\mu$l of a sterile suspension containing 1 mg of heat-killed Myco bu m tuberculosis is applied to the sponge. After air-drying overnight, the sponges are autoclaved and a cartilage slice is placed in the hole cut in the sponge disc. Under sterile conditions, the cartilage-sponge disc is placed subcutaneously in the back of an anesthetized rat (Lewis strain, 200 to 250 g). The incision is closed with staples and the rat allowed to recover from anesthesia. Approximately 5 days after sponge implantation, osmotic minipumps (Alza Corp., Palo Alto, Calif.), containing either investigational conpound or vehicle were implanted intraperitoneally in the anesthetized rat under sterile conditions After 19 days, the rats are euthanieed by asphyxiation with $CO_2$ and the granulomas containing the implanted sponge excised from the surrounding tissue.

The weight of the piece of cartilage recovered from the sponge was recorded and the collagen content of the cartilage was determined. The mean of the cartilage weights and collagen content was determined for the vehicle and drug-treated groups. The inhibition of cartilage weight and collagen content loss produced by the compounds compared with vehicle-tated rats was determined. Statistical significance (p<0.05) of vehicle-treated animals versus drug-treated animals was determined by analysis of variance.

Results:

| Treatment | Average Daily Dose (mg/kg) | % Inhibition of Cartilage Weight Loss | % Inhibition of Cartilage Collagen Loss |
|---|---|---|---|
| E ample 83 | 50 | 44.6 | 51.2* |
| E ample 313 | 50 | 45.5 | 28.0* |

* = p < 0.05 vs Vehicle-treated rats

Reference Bishop J., Greenham A K., Lewis E J. A novel in vivo model for the study of cartilage degradation. J. Pharmacol. Toxicol. Methods, 30:19–25, 1993.

Pharmaceutical Composition

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-sintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a phrmaeutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carfier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intrpeitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a tansdrmal patch containing the active compound and a carrier that is inert to the active compound, is non-toxic to the skin, and allows delivery of the agent for systemic absorption into the blood stream via the skin. The carrier may take any number of forms such as crems and ointments, pastes, gels, and occlusive devices. The crews and ointments may be viscous liquid or semi-solid emulsions of either the oil in water or water in oil type. Pastes comprised of absorptive powders dispersed in petroleum or hydrophilic petoleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering from a disease or condition in which MMPs and TACE are involved must be subjectively deterrd by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the admiddering physician based on experience with the individual subject treated and standard medical principles.

Preferably the phartaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed:
1. A compound having the formula

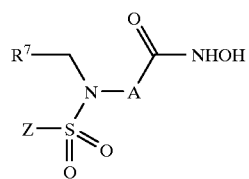

where the hydroxanic acid moiety and the sulfonamido moiety are bonded to adjacent carbons on the phenyl or naphthyl ring of group A where:
A is phenyl or naphthyl, optionally substituted by $R^1$, $R^2$, $R^3$ and $R^4$;
Z is aryl, heteroaryl, orheteroaryl fused to a phenyl,
  where aryl is phenyl or naphthyl optionally substituted by $R^1$, $R^2$, $R^3$ and $R^4$;
  heteroaryl is a 5–6 membered heteroaromatic ring having from 1 to 3 heteroatoms independently selected from N, O, and S, and optionally substituted by $R^1$, $R^2$, $R^3$ and $R^4$;
  and when heteroaryl is fused to phenyl, either or both of the rings can be optionally substituted by $R^1$, $R^2$, $R^3$ and $R^4$;
$R^1$, $R^2$, $R^3$ and $R^4$ are independently —H, —$COR^5$, —F, —Br, —Cl, —I, —$C(O)NR^5OR^6$, —CN, —$OR^5$, -$C_1$–$C_4$-perfluoroalkyl, —$S(O)_xR^5$ where x is 0–2, —$OPO(OR^5)OR^6$, —$PO(OR_6)R_5$, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, —$NR^5C(=NR^6)$ $NR^5R^6$, 3–6 membered cycloheteroalkyl having one to three heteroatoms independently selected from N, O, and S and optionally having 1 or 2 double bonds and optionally substituted by one to three groups each selected independently from $R^5$; -aryl or heterorryl as defined above, biphenyl optionally substituted by one to four groups each selected independently from $R^4$, —$SO_2NHCOR^5$ or $CONHSO_2R^5$ where $R^5$ is not H, -tetrazol-5-yl, —$SO_2NHCN$, —$SO_2NHCONR^5R^6$ or straight chain or branched -$C_1$–$C_6$ alkyl, -$C_2$–$C_6$-alkenyl, or -$C_2$–$C_6$-alkynyl, or -$C_3$–$C_6$-cycloalkyl optionally having 1 or 2 double bonds each optionally substituted with —$COR^5$, —CN, -$C_2$–$C_6$ alkenyl, -$C_2$–$C_6$ alkynyl, —$OR^5$, -$C_1$–$C_4$-perfluoroalkyl, —$S(O)_xR^5$ where x is 0–2, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, -$C_3$–$C_6$cycloalllyl as defined above, 3–6 membered cycloheteloalkyl as defined above, aryl or heteroaryl as defined above, biphenyl, —$SO_2NHCOR^5$ or —$CONHSO_2R^5$ where $R^5$ is not hydrogen; —$PO(OR^5)OR^6$, —$PO(OR^6)R^5$, -tetrazol-5-yl, $C(O)NR^5OR^6$, —$NR^5C(=NR^6)NR^5R^6$, —$SO_2NHCONR^5R^6$ or $SO_2NHCN$;

with the proviso that when $R^1$ and $R^2$ are on adjacent carbons of A, $R^1$ and $R^2$ together with the carbons to which they are attached can form a 5 to 7 membered saturated or unsaturated heterocyclic ring or a 5–6 membered heteroaryl ring, each having 1 to 3 heteroatoms independently selected from O, S, or N, and each optionally substituted by one to four groups each selected independently from $R^4$; or a 5 to 7 membered saturated or unsaturated carbocyclic ring optionally substituted by one to four groups each selected independently from $R^4$;

$R^5$ and $R^6$ are independently H, aryl and heteroaryl as defined above, -$C_3$–$C_6$-cycloalkyl as defined above, -$C_3$–$C_6$-cycloheteroalkyl as defined above, -$C_1$–$C_4$-perfluoroaikyl, or straight chain or branched -$C_1$–$C_6$ alkyl, -$C_2$–$C_6$-alkenyl, or -$C_2$–$C_6$-alkynyl each optionally substituted with —OH, —$COR^8$, —CN, —$C(O)$ $NR^8OR^9$, -$C_2$–$C_6$-alkenyl, -$C_2$–$C_6$-alkynyl, —$OR^8$, -$C_1$–$C_4$-perfluoroalkyl, —$S(O)_xR^8$ where x is 0–2, —$OPO(OR^8)OR^9$, —$PO(OR^8)R^9$, —$OC(O)NR^8R^9$, —$COOR^8$, —$CONR^8R^9$, —$SO_3H$, —$NR^8R^9$,—$NCOR^8R^9$, —$NR^8COOR^9$, —$SO_2NR^8R^9$, —$NO_2$, —$N(R^8)SO_2R^9$, —$NR^8CONR^8R^9$, -$C_3$–$C_6$ cycloaalyl as defined above, 3–6 membered cycloheteroalkyl as defined above, aryl or heteroaryl as defined above, —$SO_2NHCOR^8$ or —$CONHSO_2R^8$ where $R^8$ is not hydrogen, -tetrazol-5-yl, —$NR^8C(=NR^9)NR^8R^9$, —$SO_2NHCONR^8R^9$, or —$SO_2NHCN$;

$R^7$ is hydrogen, straight chain or branched -$C_1$–$C_6$-alkyl, -$C_2$–$C_6$-alkenyl, or -$C_2$–$C_6$-alkynyl each optionally substituted with —OH, —$COR^5$, —CN, -$C_2$–$C_6$-alkenyl, -$C_2$–$C_6$-alkynyl, —$OR^5$, -$C_1$–$C_4$-perfluoroalkyl, —$S(O)_xR^5$ where x is 0–2, —$OPO(OR^5)OR^6$, —$PO(OR^5)R^6$, —$OC(O)NR^5R^6$, —$COOR^5$, —$CONR^5R^6$, —$SO_3H$, —$NR^5R^6$, —$NR^5COR^6$, —$NR^5COOR^6$, —$SO_2NR^5R^6$, —$NO_2$, —$N(R^5)SO_2R^6$, —$NR^5CONR^5R^6$, -$C_3$–$C_6$ cycloalkyl as defined above, -$C_3$–$C_6$-cycloheteroalkyl as defined above, -aryl or heteroaryl as defined above, —SO₂NHCOR⁵ or —CONHSO₂R⁵ where R⁵ is not hydrogen, -tetrazol-5-yl, —NR⁵C(=NR6)NR⁵R⁶, —C(O)NR⁵OR⁶, —SO₂NHCONR⁵R⁶ or —SO₂NHCN;
- or R⁷ is phenyl or naphthyl, optionally substituted by R¹, R², R³ and R⁴ or a 5 to 6 membered heteroaryl group having 1 to 3 heteroatoms selected independendy from N, O, and S and optionally substituted by R¹, R², R³ and R⁴;
- or R⁷ is C₃–C₆ cycloalkyl or 3–6 membered cycloheteroalkyl as defined above;
- or R⁷CH₂—N—A—, where A is as defined above, can form a non-aromatic 1,2-benzo-fused 7–10 membered heterocyclic ring optionally containing an additional heteroatom selected from O, S and N wherein said heterocyclic ring may be optionally fused to another benzene ring;
- R⁸ and R⁹ are independently H, aryl or heteroaryl as defined above, -C₃–C₇-cycloalkyl or 3 to 6 membered cycloheteroalkyl as defined above, -C₁–C₄-perfluoroalkyl, straight chain or branched -C₁–C₆-alkyl, -C₂–C₆-alkenyl, or -C₂–C₆-alkynyl, each optionally substituted with hydroxy, alkoxy, aryloxy, -C₁–C₄-perfluoroalkyl, amino, mono- and di-C₁–C₆-alkylanino, carboxylic acid, carboalkoxy and carboaryloxy, nitro, cyano, carboxamido primary, mono- and di-C₁–C₆-alkylcarbamoyl;
- a pharmaceutically acceptable salt thereof where one may be formed; and an optical isomer or diastereorner thereof where optical isomers and diastereoeers exist.

2. A compound according to claim 1 wherein both of the carbons of A adjacent to the carbon bearing the sulfonamido group have a substituent other than hydrogen.

3. A cornpound according to claim 2 wherein the Z group is para-alkoxyphenyl, para-aryloxyphenyl or para-heteroaryloxyphenyl.

4. A compound according to claim 3 which is selected from the group consisting of:
2-[Benzyl-(4-methoxy-benzenesulfonyl)-amino]-3-chloro-N-hydroxy-benzamide,
2-[Benzyl-(4-methoxy-benzentsulfonyl)-amino]-5-bromo-N-hydroxy-3-methyl-benzamide,
2-[Benzyl-(4-methoxy-benzenesulfonyl)-amino]-N-hydroxy-3-methyl-benzamnide,
2-[Benzyl-(4-methoxy-benzenesulfonyl)-amino]-3-benzyloxy-N-hydroxy-benzamide,
2-[Benzyl-(4-methoxy-benzenesulfonyl)-amino]-N-hydroxy-3-hydroxycarbamoyl-methoxy-benzamide,
2-[Benzyl-(4-methoxy-benzenesulfonyl)-amino]-N-hydroxy-3-(2,2,2-trifuoroethoxy)-benzamide,
2-[Benzyl-(4-methoxy-benzenesulfonyl)-amino]-N-hydroxy-3-(2-methoxy-ethoxymethoxy)-benzamide,
2-[Benzyl-(4-methoxy-benzenesulfonyl)-amino]-3-[4-(hydroxyaminocarbonyl)-benzyloxy]-N-hydroxy-benzamide,
2-[Benzyl-(4-methoxy-benzenesulfonyl)-amino]-N-hydroxy-3-(3-hydroxycarbamoyl-propoxy)-benzamide,
2-[Benzyl-(4-methoxy-benzenesulfonyl)-amino]-N-hydroxy-3-(4-hydroxy-cabamoyl-butoxy)-benzamide,
2-[Benzyl-(4-methoxy-benzenesulfonyl)-amino]-N-hydroxy-3-isopropoxy-benzamide,
N-Hydroxy-2-[(4-methoxy-benzenesulfonyl)-pyrdin-3-ylmethyl-amino]-3-methyl-benzamide,
2-[Benzyl-(4-methoxy-benzenesulfonyl)-amino]-N-hydroxy-3,5-dimethyl-benzamide,
2-[Benzyl-(4-fluoro-benzenesulfonyl)-amino]-N-hydroxy-3,5-dimethyl-benzamide,
2-[Benzyl-(4-butoxy-benzenesulfonyl)-anino]-N-hydroxy-3,5-dimethyl-benzamide,
2-[Benzyl-(4-benzyloxy-benzenesulfonyl)-amino]-N-hydroxy-3,5-dimethyl-benzamide,
2-[Benzyl-(4-methoxy-benzenesulfonyl)-amino]-5-hex-1-ynyl-N-hydroxy-3-methyl-benzamide,
2-[Benzyl-(4-methoxy-benzenesulfonyl)-amino]-5-ethynyl-N-hydroxy-3-methyl-benzamide,
N-Hydroxy-2-[(4-methoxy-benzenesulfonyl)-pyridin-3-ylmethyl-amino]-3-methyl-benzamide,
N-Hydroxy-2-[(4-methoxy-benzenesulfonyl)-pyridin-3-ylmethyl-amino]-3,5-dimethyl-benzamide,
5-Bromo-N-hydroxy-2-[(4-methoxy-benzenesulfonyl)-pyridin-3-ylmethyl-amino]-3-methyl-benzamide,
2-[Benzyl-(4-methoxy-benzenesulfonyl)-amino]-N-hydroxy-3-methoxy-benzamide,
2-[Benzyl-(4-methoxy-benzenesulfonyl)-amino]-4-chloro-N-hydroxy-3-methyl-benzamide,
N-Hydroxy-2-[(4-methoxy-benzenesulfonyl)-(3-methoxy-benzyl)-amino]-3,5-dimethyl-benzamide,
N-Hydroxy-2-[(4-methoxy-benzenesulfonyl)-(2,3,5,6-tetrafluoro-4-nethoxy-benzyl)-amino]-3,5-dimethyl-benzamide,
N-Hydroxy-2-[(4-methoxy-benzenesulfonyl)-propyl-amino]-3,5-dimethyl-benzamide,
2-[(2-Bromo-benzyl)-(4-methoxy-benzenesulfonyl)-amino]-N-hydroxy-3,5-dimethyl-benzamide,
2-[(3-Bromo-benzyl)-(4-methoxy-benzenesulfonyl)-amino]-N-hydroxy-3,5-dimethyl-benzamide,
2-[(4-Bromo-benzyl)-(4-methoxy-benzenesulfonyl)-amino]-N-hydroxy-3,5-dimethyl-benzamide,
2-[Benzyl-(4-methoxy-benzenesulfonyl)-amino]-N-hydroxy-3-trifluoromethyl-benzamide,
N-Hydroxy-2-[(4-methoxy-benzenesulfonyl)-methyl-amino]-3,5-dimethyl-benzamide,
2-[Ethyl-(4-methoxy-benzenesulfonyl)-amino]-N-hydroxy-3,5-dimethyl-benzamide,
3-Bromo-N-hydroxy-2-[(4-methoxy-benzenesulfonyl)-pyridin-3-ylmethyl-amino]-5-methyl-benzamide,
N-Hydroxy-2-[(4-methoxy-benzenesulfonyl)-pyridin-3-ylmethyl-amino]-5-methyl-3-thiophen-2-yl-benzamide,
N-Hydroxy-2-[(4-methoxy-benzenesulfonyl)-methyl-amino]-3,5-dimethyl-benzamide,
2-[Ethyl-(4-methoxy-benzenesulfonyl)-amino]-N-hydroxy-3,5-dimethyl-benzamide,
2-[Benzyl-(4-methoxy-benzenesulfonyl)-amino]-N-hydroxy-3,4,5-trimethoxy-benzamide,
N-Hydroxy-3,4,5-trimethoxy-2-[(4-methoxy-benzenesulfonyl)-pyridin-3-ylmethyl-amino]-benzamide,
5-(4-Methoxy-benzenesulfonyl)-2,3,4,5-tetrahydro-1,5-benzoxazepine-6-carboxylic acid hydroxyamide,
12-(4-Methoxy-benzenesulfonyl)-11,12-dihydro-6H-dibenz[b,f][1,4]oxazocine-1-carboxylic acid hydroxyamide,
6-(4-Methoxy-benzenesulfonyl)-3,4,5,6-tetrahydro-2H-1,6-benzoxazocine-7-carboxylic acid hydroxyamide,
2-[Benzyl-(4-methoxy-benzenesulfonyl)-amino]-N-hydroxy-3-nitro-benzamide,
2-[Benzyl-(4-methoxy-benzenesulfonyl)-amino]-N-hydroxy-3-(3-hydroxy-propoxy)-benzamide,
N-Hydroxy-2-[(4-methoxybenzenesulfonyl)-pyridin-3-ylmethyl-amino]-3-methyl-5-thiophen-2-yl benzamide,
2-[Benzyl-(4-methoxybenzenesulfonylamino)-N-hydroxy-3-cyano-5-methyl-benzamide,
3-Furan-2-yl-N-hydroxy-2-[(4-methoxybenzenesulfonyl)-pyridin-3-ylmethyl-amino]-5-methyl-benzamide,
3-Diethylaminomethyl-N-hydroxy-2-[(4-methoxybenzenesulfonyl)-methylamino]-benzamide, N-Hydroxy-2-[(4-methoxybenzenesulfonyl)-methylamino]-3-(4-methylpiperazin-1-ylmethyl)-benzamide,
2-[Benzyl-(4-methoxybenzenesulfonyl)amno]-3-(1-ethoxycarbonyl-N-hydroxy-1-methylethoxy-benzamide,
3-Bromo-2-[benzyl-(4-methoxybenzenesulfonyl)amino]-N-hydroxy-benzamide,
N-Hydroxy-2-[(4-methoxy-benzenesulfonyl)-methyl-amino]-3-methyl-5-[2-(methyl-octyl-carbanoyl)-vinyl]-benzamide,
N-Hydroxy-2-[(4methoxy-benzenesulfonyl)-methyl-amino]-3-methyl-5-[2-(methyl-octyl-carbamoyl)-ethyl]-benzamide,
5-(2-Dimethylcarbamoyl-vinyl)-N-hydroxy-2-[(4-methoxy-benzenesulfonyl)-methyl-amino]-3-methyl-benzamide,
5-[2-(Ethyl-pyridin-4-ylmethyl-carbamoyl)-vinyl]-N-hydroxy-2-[(4-methoxy-benzenesulfonyl)-methyl-amino]-3-methyl-benzamide,
N-Hydroxy-2-[(4-methoxy-benzenesulfonyl)-pyridin-3-ylmethyl-amino]-3-methyl-5-[2-(methyl-octyl-carbamoyl)-vinyl]-benzamide,
5-(2-Dimethylcarbamoyl-vinyl)-N-hydroxy-2-[(4-methoxy-benzenesulfonyl)-pyridin-3-ylmethyl-amino]-3-methyl-benzamide,
5-[2-(Ethyl-phenyl-carbamoyl)-vinyl]-N-hydroxy-2-[(4-methoxy-benzenesulfonyl)-pyridin-3-ylmethyl-amino]-3-methyl-benzamide,
5-(2-Diallylcarbamoyl-vinyl)-N-hydroxy-2-[(4-methoxy-benzenesulfonyl)-pyridin-3-ylmethyl-amino]-3-methyl-benzamide,
N-Hydroxy-2-[(4-methoxy-benzenesulfonyl pyridin-3-ylmethyl-amino]-3-methyl-5-(3-morpholin-4-yl-3-oxo-propenyl)-benzamide,
2'-(Hydroxyimino-methyl)-4-[(4-methoxy-benzenesulfonyl)-pyridin-3-ylmethyl-amino]-5-methyl-biphenyl-3-carboxylic acid hydroxyamide,
3'-(Hydroxyimino-methyl)-4-[(4-methoxy-benzenesulfonyl)-pyridin-3-ylmethyl-amino]-5-methyl-biphenyl-3-carboxylic acid hydroxyamide,
4'-(Hydroxyimino-methyl)-4-[(4-methoxy-benzenesulfonyl)-pyridin-3-ylmethyl-amino]-5-methyl-biphenyl-3-carboxylic acid hydroxyamide,
4-[(4-Methoxy-benzenesulfonyl)-pyridin-3-ylmethyl-amino]-5-methyl-2'-trifluoromthyl-biphenyl-3-carboxylic acid hydroxyamide,
5-Furan-2-yl-N-hydroxy-2-[(4-methoxy-benzenesulfonyl)-pyridin-3-ylmethyl-amino]-3-methyl-benzamide,
N-Hydroxy-5-[3-(hydroxyimino-methyl)-thiophen-2-yl]-2-[(4-methoxy-benzenesulfonyl)-pyridin-3-ylmethyl-amino]-3-methyl-benzamide,
5-(5-Chloro-thiophen-2-yl)-N-hydroxy-2-[(4-methoxy-benzenesulfonyl)-pyridin-3-ylmethyl-amino]-3-methyl-benzamide,
5-(5-Acetyl-thiophen-2-yl)-N-hydroxy-2-[(4-methoxy-benzenesulfonyl)-pyridin-3-ylmethyl-amino]-3-methyl-benzamide,
2-[Benzyl-(4-methoxy-benzenesulfonyl)-amino]-N-hydroxy-3-methyl-5-vinyl-benzamide,
4-[Benzyl-(4-methoxy-benzenesulfonyl)-amino]-N(1),N(3)-dihydroxy-5-methyl-isophthalamide di-sodium salt,
5-Ethyl-N-hydroxy-2-[(4-methoxy-benzenesulfonyl)-pyridin-3-ylmethyl-amino]-3-methyl-benzamide,
2-[Benzyl-(4-methoxy-benzenesulfonyl)-amino]-5-diethyiaminomethyl-N-hydroxy-3-methyl-benzamide,
N-Hydroxy-2-[(4-methoxy-benzenesulfonyl)-pyridin-3-ylmethyl-amino]-3-methyl-5-pyridin-3-yl-benzamide,
2-[Benzyl-(4-methoxy-benzenesulfonyl)-amino]-N-hydroxy-3,6-dimethyl-benzamide,
N-Hydroxy-2-[(4-methoxy-benzenesulfonyl)-pyridin-3-ylmethyl-amino]-3,6-dimethyl-benzamide,
N-Hydroxy-2-[(4-methoxy-benzenesulfonyl)-pyridin-3-ylmethyl-amino]-3-methyl-5-[3-(5-methyl-furan-2-yl)-isoxazol-5-yl]-benzamide,
2-[Benzyl-(4-ethoxy-benzenesulfonyl)-amino]-N-hydroxy-3,5-dimethyl-benzamide,
2-[Benzyl-(4-propoxy-benzenesulfonyl)-arnino]-N-hydroxy-3,5-dimethyl-benzamide,
2-[Benzyl-(4-isopropoxy-benzenesulfonyl)-amino]-N-hydroxy-3,5-dimethyl-benzamide,
2-[Benzyl-(4-benzyloxy-benzenesulfonyl)-amino]-5-bromo-N-hydroxy-3-methyl-benzamide,
N-Hydroxy-2-[(4-methoxy-benzenesulfonyl)-methyl-amino]-3-morpholin-4-ylmethyl-benzamide,
N-Hydroxy-2-[(4-methoxy-benzenesulfonyl)-methyl-amino]-3-pyrrolidin-1-ylmethyl-benzamide,
N-Hydroxy-3-imidazol-1-ylmethyl-2-[(4-methoxy-benzenesulfonyl)-methyl-amino]-benzamide,
5-Bromo-N-hydroxy-2-[(4-methoxy-benzenesulfonyl)-methyl-amino]-3-(4-methyl-piperazin-1-ylmethyl)-benzamide,
5-Bromo-N-hydroxy-2-[(4-methoxy-benzenesulfonyl)-methylamino]-3-pyrrolidin-1-ylmethyl-benzamide,
N-Hydroxy-2-[(4-methoxy-benzenesulfonyl)-pyridin-3-ylmethyl-amino]-3-pyrrolidin-1-ylmethyl-benzamide,
N-Hydroxy-2-[(4-methoxy-benzenesulfonyl)-octyl-amino]-3-(4-methyl-piperazin-1-ylmethyl)-benzamide,
N-Hydroxy-2-[(4-methoxy-benzenesulfonyl)-thiophen-3-ylmethyl-amino]-3-(4-methyl-piperazin-1-ylmethyl)-benzamide,
N-Hydroxy-2-[[(4-methoxyphenyl)sulfonyl](phenylmethyl)-amino]-3-[(4-methyl-1-piperazinyl)methyl]benzamide,
N-Hydroxy-2-[(4-methoxy-benzenesulfonyl)-pyridin-3-ylmethyl-amino]-3-(tetrahydro-pyran-2-yloxymethyl)-benzamide,
N-Hydroxy-3-hydroxymethyl-2-[(4-methoxy-benzenesulfonyl)-pyridin-3-ylmethyl-amino]-benzamide,
2-[Benzyl-(4-methoxy-benzenesulfonyl)-amino]-3-[2-(tert-butyl-dimethyl-silanyloxy)-ethoxy]-N-hydroxy-benzamide,
2-[Benzyl-(4-methoxy-benzenesulfonyl)-amino]-N-hydroxy-3-(2-hydroxy-ethoxy)-benzamide,
5-Bromo-N-hydroxy-3-[2-(hydroxycarbamoyl)-ethyl]-2-[(4-methoxy-benzenesulfonyl)-methyl-amino]-benzamide,
N-Hydroxy-3-[2-(hydroxycarbamoyl)-ethyl]-2-[(4-methoxy-benzenesulfonyl)-methyl-amino]-benzamide,
5-Biphenyl-4-ylethynyl-N-hydroxy-2-[(4-methoxy-benzenesulfonyl)-methyl-amino]-3-methyl-benzamide,
5-(2-Biphenyl-4-yl-ethyl)-N-hydroxy-2-[(4-methoxy-benzenesulfonyl)-methyl-amino]-3-methyl-benzamide,
5-Dodec-1-ynyl-N-hydroxy-2-[(4-methoxy-benzenesulfonyl)-methyl-amino]-3-methyl-benzamide,
5-Dodecyl-N-hydroxy-2-[(4-methoxy-benzenesulfonyl)-methyl-amino]-3-methyl-benzamide,
N-Hydroxy-2-[(4-methoxy-benzenesulfonyl)-pyridin-3-ylmethyl-amino]-3-methoxymethyl-benzamide,
N-Hydroxy-2-[(4-methoxy-benzenesulfonyl)-pyridin-3-ylmethyl-amino]-isophthalamic acid tert-butyl ester,
N-Hydroxy-2-[(4-methoxy-benzenesulfonyl)-pyridin-3-ylmethyl-amino]-isophthalamic acid methyl ester,
N-Hydroxy-2-[(4-methoxy-benzenesulfonyl)-methyl-amino]-isophthalamnic acid methyl ester,
N-Hydroxy-2-[(4-methoxy-benzenesulfonyl)-pyridin-3-ylmethyl-amino]-isophthalamic acid, N-Hydroxy-2-[(4-methoxy-benzenesulfonyl)-pyridin-2-ylmethyl-amino]-3-methyl-benzamide,
N-Hydroxy-2-[(4-methoxy-benzenesulfonyl)-pyridin-4-ylmethyl-amino]-3-methyl-benzamide,
2-[(4-Diethylaminomethyl-benzyl)-(4-methoxy-benzenesulfonyl)-amino]-N-hydroxy-3-methyl-benzamide,
2-[(4-Dimethylaminomethyl-benzyl)-(4-methoxy-benzenesulfonyl)-amino]-N-hydroxy-3-methyl-benzamide,
2-[(4-Diethylamino-but-2-ynyl)-(4-methoxy-benzenesulfonyl)-amino]-N-hydroxy-3-methyl-benzamide,
N-Hydroxy-2-{(4-methoxy-benzenesulfonyl)-[4-(4-methyl-piperazin-1-yl)-benzyl]-amino}-3-methyl-benzamide,
4-[(2-Hydroxycarbamoyl-6-methyl-phenyl)-(4-methoxy-benzenesulfonyl)-animo]-butyric acid ethyl ester,
5-[(2-Hydroxycarbanoyl-6-methyl-phenyl)-(4-methoxy-benzenesulfonyl)-amino]-pentanoic acid ethyl ester,
[(2-Hydroxycarbamoyl-6-methyl-phenyl)-(4-methoxy-benzenesulfonyl)-amino]-acetic acid benzyl ester,
N-Hydroxy-2-[[(4-methoxyphenyl)sulfonyl][2-oxo-2-[(2-pyridinylmethyl)amino]ethyl]amino]-3-methylbenzamide,
N-Hydroxy-2-{(4-methoxy-benzenesulfonyl)-[2-(4-methyl-piperazin-1-yl)-2-oxo-ethyl]-amino}-3-methyl-benzamide,
N-Hydroxy-2-[(2-hydroxy-ethyl)-(4-methoxy-benzenesulfonyl)-amino]-3-methyl-benzamide,
2-[Benzyl-(4-methoxy-benzenesulfonyl)-amino]-5-dimethylamino-N-hydroxy-3-methyl-benzamide,
2-[Benzyl-(4-methoxy-benzenesulfonyl)-amino]-3-dimethylamino-N-hydroxy-benzamide,
N-Hydroxy-2-[[(4-methoxyphenyl)sulfonyl][[4-[2-(1-piperidinyl)ethoxy]phenyl]methyl]amino]-3-methylbenzamide,
2-[[4(2-Diethylamino-ethoxy)-benzyl]-(4-methoxy-benzenesulfonyl)-amino]-N-hydroxy-3-methyl-benzamide,
5-Bromo-N-hydroxy-2-{(4-methoxy-benzenesulfonyl)-[4-(2-piperidin-1-yl-ethoxy)-benzyl]-amino}-3-methyl-benzamide,
N-Hydroxy-2-[[(4-methoxyphenyl)sulfonyl][[4-[[2-(1-piperidinyl)ethyl]amino]carbonyl]phenyl]methyl]amino]-3-methylbenzamide,
4-[(4-Methoxy-benzenesulfonyl)-pyridin-3-ylmethyl-amino]-5-methyl-biphenyl-3-carboxylic acid hydroxamide hydrochloride salt,
N-Hydroxy-2-[(4-methoxy-benzenesulfonyl)-pyridin-3-ylmethyl-amino]-3-methyl-5-thiophen-3-yl-benzamide hydrochloride salt,
4"-Methoxy-4-[(4-methoxy-benzenesulfonyl)-pyridin-3-ylmethyl-amino]-5-methyl-[1,1';4',1"]terphenyl-3-carboxylic acid hydroxyamide hydrochloride salt,
4-[(4-Methoxy-benzenesulfonyl)-pyridin-3-ylmethyl-amino]-5-methyl-3'-nitro-biphenyl-3-carboxylic acid hydroxyamide hydrochloride salt,
4'-Methoxy-4-[(4-methoxy-benzenesulfonyl)-pyridin-3-ylmethyl-amino]-5-methyl-biphenyl-3-carboxylic acid hydroxyamide hydrochloride salt,
5-Benzo[b]thiophen-2-yl-N-hydroxy-2-[(4-methoxy-benzenesulfonyl)-pyridin-3-ylmethyl-amino]-3-methyl-benzamide hydrochloride salt,
5-Benzo[b]furaphen-2-yl-N-hydroxy-2-[(4-methoxy-benzenesulfonyl)-pyridin-3-ylmethyl-amino]-3-methyl-benzamide hydrochloride salt,
4-[(4-Methoxy-benzenesulfonyl)-pyridin-3-ylmethyl-amino]-5-methyl-4'-trifluoromethoxy-biphenyl-3-carboxylic acid hydroxyamide hydrochloride salt,
5-Benzo[1,3]dioxol-5-yl-N-hydroxy-2-[(4-methoxy-benzenesulfonyl)-pyridin-3-ylmethyl-amino]-3-methyl-benzamide hydrochloride salt,
4-[(4-Methoxy-benzenesulfonyl)-pyridin-3-ylmethyl-amino]-5-methyl-3'-trifluoromethyl-biphenyl-3-carboxylic acid hydroxyamide hydrochloride salt,
2-[(4-Chloro-benzyl)-(5-pyridin-2-yl-thiophene-2-sulfonyl)-amino]-N-hydroxy-3-methyl-benzamide,
2-[(3,4-Dimethyl-benzyl)-(5-pyridin-2-yl-thiophene-2-sulfonyl)-amino]-N-hydroxy-3-methyl-benzamide,
N-Hydroxy-3-methyl-2-[pyridin-3-ylmethyl-(4'-triuoromethyl-biphenyl-4-sulfonyl)-amino]-benzamide,
2-[(2',4'-Dimethoxy-biphenyl-4-sulfonyl)-pyridin-3-ylmethyl-amino]-N-hydroxy-3-methyl-benzamide,
N-Hydroxy-3-methyl-2-[pyridin-3-ylmethyl-(4-thiophen-2-yl-benzenesulfonyl)-amino]-benzamide,
2-[(4-Ethynyl-benzenesulfonyl)-pyridin-3-ylmethyl-amino]-N-hydroxy-3-methyl-benzamide,
2-[(4-Benzo[b]thiophen-2-yl-benzenesulfonyl)-pyridin-3-ylmethyl-amino]-N-hydroxy-3-methyl-benzamide,
2-[(4-Benzo[1,3]dioxol-5-yl-benzenesulfonyl)-pyridin-3-ylmethyl-amino]-N-hydroxy-3-methyl-benzamide and
3-Methyl-2-[4-(pyridin-4-yloxy)-benzensulfonylamino]-N-hydroxy-benzamide.

5. A compound according to claim 1 which is selected from the group consisting of:
2-[Benzyl-(4-methoxy-benzenesulfonyl)-amino]-N-hydroxy-benzamide,
2-[Benzyl-(4-methoxy-benzenesulfonyl)-amino]-N-hydroxy-4-methyl-benzamide,
2-[Benzyl-(4-medhoxy-benzenesulfonyl)-amino]-N-hydroxy-6-methyl-benzamide,
2-[Benzyl-(4-methoxy-benzenesulfonyl)-amino]-N-hydroxy-5-methyl-benzamide,
N-Hydroxy-2-[(4-methoxy-benzenesulfonyl)-pyridin-3-ylmethyl-amino]-benzamide, and
3-[Benzyl-(4-methoxybenzenesulfonyl)-amino]-naphthalene-2-carboxylic acid hydroxyamide.

6. A method of inhibiting pathological changes mediated by matrix metalloproteinases in mammals which comprises administration to a mammal in need thereof a therapeutically effective amount of a matrix metalloproteinase inhibiting compound according to claim 1.

7. A method according to claim 6 wherein the condition treated is atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, or periodontal disease.

8. A medtod according to claim 6 wherein the condition treated is age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

9. A method of inhibiting pathological changes mediated by TNF-α converting enzyme (TACE) in mammals which comprises administration to a mammal in need thereof a theapeufically effective amount of a TACE inhibiting compound according to claim 1.

10. The method according to claim 9 wherein the condition treated is rheumatoid arthritis, graft rejection, cachexia, anorexia, inflammation, fever, insulin resistance, septic shock, congestive heart failure, inflamatory disease of the central nervous system, inflammatory bowel disease, or HIV infection.

11. A pharmaceutical composition comprising a pharmaceutical carrier and a therapeutically effective amount of a matrix metalloproteinase or TACE inhibiting compound according to claim 1.

* * * * *

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 1 - line 17 - delete "abnormoal", insert abnormal"

Col. 1 - line 34 - delete "intimtly", insert "intimately"

Col. 1 - line 44 - delete "gelatnase", insert "gelatinase"

Col. 2 - line 22 - delete "inflamon", insert "inflammation"

Col. 2 - line 23 - delete "keratoconus", insert "keratoconus"

Col. 2 - line 44 - delete articulr", insert "articular"

Col. 2 - line 61 - delete "arly", insert "early"

Col. 2 - line 62 - delete mimeti, insert "mimetic"

Col. 3 - line 1 - delete "pro inflao iatory", insert "pro-inflammatory"

Col. 3 - line 5 - delete "animas", insert "animals"

Col. 3 - line 19 - delete "treting", insert "treating"

Col. 3- line 30 - delete "non-peptide", insert "non-peptic"

Col. 3 - line 31 - delete "recendy", insert "recently"

Col. 4 - line12 - delete "contning", insert "containing"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 4 - line 27 - delete "stmcture", insert "structure"

Col. 5 - line 24 - delete "cycloheteroallyl", insert "cycloheteroalkyl"

Col. 5 - line 51 - delete "NCOR⁸R⁹", insert "NR⁸COR⁹"

Col. 5 - line 53 - delete "rnembered", insert "membered"

Col. 6 - line 30 - delete "primay", insert "primary"

Col. 6 - line 34 - delete "diastremrs", insert "diastereomers"

Col. 10 - line 2 - delete "alkli-forming", insert "alkali-forming"

Col. 10 - line 16 - delete "cerain", insert "certain"

Col. 12 - line 3 - delete "antanilic", insert "anthranitic"

Col. 17 - line 2 - delete "padium", insert "palladium"

Col. 18 - line 50 - delete "anthrnilic", insert "anthranilic"

Col. 19 - line 1 - delete "anthanilic", insert "anthranilic"

Col. 19 - line 3 - delete "anthanilic", insert "anthranilic"

Col. 19 - line 4 - delete "diplaced", insert "displaced"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 19 - line 4 - delete "malonte", insert "malonate"

Col. 24 - line 31 - delete "transforred", insert "transformed"

Col. 25 - line 18 - delete "lopimr", insert "primary"

Col. 25 - line 20 - delete "hydroxamnic", insert "hydroxamic"

Col. 35 - next to last line - delete 'may, insert "may"

Col. 39 - line 66 - delete "anthilt", insert "anthranilate"

Col. 40 - line 2 - delete "reacon", insert "reaction"

Col. 41 - line 39 - delete "EtOAc/Iexanes", insert "EtOAc/hexanes

Col. 47 - line 67 - delete "extrcted", insert "extracted"

Col. 52- line 20 - delete "eaction", insert "reaction"

Col. 52 - line 31 - delete "edter", insert "ether"

Col. 52 - line 53 - delete "motion", insert "reaction"

Col. 52 - line 54 - delete "zeflux", insert "reflux"

Col. 52 - line 54 - delete "tempemaure", insert "temperature"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 53 - line 25 - delete "Hcl", insert "HCl"

Col. 53- line 29 - delete "temperatue", insert "temperature"

Col. 53- line 65 - delete "temre", insert "temperature"

Col. 53 - line 67 - delete "steeed", insert "stirred"

Col. 54 - line 19 - delete "temeratue", insert "temperature"

Col. 54 - line 21 - delete "tide", insert "title"

Col. 54 - line 31 - delete "stined", insert "stirred"

Col. 54 - line 34 - delete "stifed", insert "stirred"

Col. 54 - line 36 - delete tdethylamine, insert "triethylamine"

Col. 54 - line 42 - delete "temperatue", insert "temperature"

Col. 54 - line 42 - delete "stirng", insert "stirring"

Col. 54 - line 42 - delete "Ie", insert "The"

Col. 54 - line 47 - delete "tide", insert "title"

Col. 54 - line 49 - delete "tempeture", insert "temperature"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 54 - line 50 - delete "tempeture", insert "temperature"

Col. 54 - line 52 - delete "stimd", insert "stirred"

Col. 54 - line 54 - delete "died", insert "dried"

Col. 54 - line 65 - delete "steeed", insert "stirred"

Col. 54 - line 66 - delete "temprature", insert "temperature"

Col. 55 - line 1 - delete "stied", insert "stirred"

Col. 55 - line 15 - delete "tide", insert "title"

Col. 55 - line 33 - delete "Exalmpe", insert "Example"

Col. 56 - line 19 - delete "maaer", insert "manner"

Col. 57 - line 40 - delete "triton", insert "trituration"

Col. 58 - line 8 - delete "concentad", insert "concentrated"

Col. 59 - line 19 - delete "Electm-spray", insert "Electrospray"

Col. 59 - line 27 - delete "amn", insert "manner"

Col. 59 - line 59 - delete "trturation", insert "trituration"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 61 - line 28 - delete "nitrosonium", insert "nitrosodium"

Col. 61 - line 49 - delete "iodomethaie", insert "iodomethane"

Col. 62 - line 38 - delete "Iromine", insert "bromine"

Col. 63 - line 4 - delete "triteretd", insert "triturated"

Col. 63 - line 18 - delete "conntrated", insert "concentrated"

Col. 63 - line 30 - delete "niixture", insert "mixture"

Col. 63 - line 34 - delete "concentraed", insert "concentrated"

Col. 63 - line 44 - delete "neutraliation", insert "neutralization"

Col. 64 - line 1 - delete "tdbutyltin", insert "tributyltin"

Col. 70 - line 22 - delete "aceteexane", "insert acetate/hexane"

Col. 70 - line 34 - delete "neutized", insert "neutralized"

Col. 70 - line 57 - delete "pyridi", insert "pyridine"

Col. 73 - line 11 - delete "tide comod", insert "title compound"

Col. 73 - line 32 - delete "tide", insert "title"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 74 - line 40 - delete "stird", insert "stirred"

Col. 74 - line 44 - delete "dichlromethane", insert "dichloromethane"

Col. 75 - line 20 - delete "stifled", insert "stirred"

Col. 75 - line 26 - delete "concentnted", insert "concentrated"

Col. 75 - line 38 - delete "stirre", insert "stirred"

Col. 77 - line 4 - delete "sired", insert "stirred"

Col. 77 - line 53 - delete "stilred", insert "stirred"

Col. 77 - line 54 - delete "nmxture", insert "mixture"

Col. 77 - line 54 - delete "brne", insert "brine"

Col. 79 - line 49 - delete "N-ethylacrylianilide", insert "N-ethylacrylanilide"

Col. 80 - line 43 - delete "tenperature", insert "temperature"

Col. 87 - line 25 - delete "Exanple", insert "Example"

Col. 87 - line 55 - delete "vacu", insert "vacuo"

Col. 91 - line 62 - delete "accoding", insert "according"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 93 - line 19 - delete "Electmspray", insert "Electrospray"

Col. 94 - line 30 - delete "pyrrodine", insert "pyrrolidine"

Col. 94 - line 67 - delete "pyirolidine", insert "pyrrolidine"

Col. 95 - line 1 - delete "raction", insert "reaction"

Col. 95 - line 6 - delete "a.", insert "a"

Col. 95 - line 44 - delete "exited", insert "extracted"

Col. 97 - line 43 - delete "concenteeted in.", insert "concentrated in."

Col. 98 - line 1 - delete "N-N-imethylformamide", insert "N,N-dimethylformamide"

Col. 98 - line 39 - delete "chlorofornmethanol", insert "chloroform/methanol"

Col. 99 - line 24 - delete "temperate", insert "temperature"

Col. 99 - line 35 - delete "methyl", insert "methyl] "

Col. 100 - line 3 - delete "collcted", insert "collected"

Col. 100 - line 14 - delete "tciaerpate", insert "temperature"

Col. 100 - line 23 - delete "died", insert "dried"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 100 - line 25 - delete "sicca", insert "silica"

Col. 100 - line 39 - delete "chnoatographed", insert "chromatographed"

Col. 101 - line 8 - delete "acetonitrire", insert "acetonitrile"

Col. 101 - line 9 - delete "stined", insert "stirred"

Col. 101 - line 10 - delete "temprature", insert "temperature"

Col. 101 - line 28 - delete "Hiexanes", insert "hexanes"

Col. 101 - line 32 - delete "reactioon", insert "reaction"

Col. 102 - line 28 - delete "cluting", insert "eluting"

Col. 104 - line 55 - delete "exte", insert "extracted"

Col. 107 - line 22 - delete "carroxylic", insert "carboxylic"

Col. 107 - line 67 - delete "stire", insert "stirred"

Col. 109 - line 29 - delete "colketed", insert "collected"

Col. 110 - line 61 - delete "dichlcwo thane", insert "dichloromethane"

Col. 110 - line 61 - delete "steeed", insert "stirred"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 110 - line 62 - delete "terpeanre", insert "temperature"

Col. 111 - line 21 - delete "cafroxylic", insert "carboxylic"

Col. 111 - line 67 - delete "carboxylc", insert "carboxylic"

Col. 113 - line 13 - delete "obtined", insert "obtained"

Col. 114 - line 18 - delete "ex=aWd", insert "extracted"

Col. 114 - line 54 - delete "subsequendy", insert "subsequently"

Col. 114 - line 58 - delete "Example.", insert "Example"

Col. 115 - line 41 - delete "sulfonamnide", insert "sulfonamide"

Col. 116 - line 45 - delete "sulfonanide-eter", insert "sulfonamide-ester"

Col. 116 - line 65 - delete "filtaed", insert "filtered"

Col. 117 - line 4 - delete "chlo", insert "chloro"

Col. 117 - line 11 - delete "vacum", insert "vacuum"

Col. 117 - line 49 - delete "dichlncthane", insert "dichloromethane"

Col. 118 - line 59 - delete "teen", insert "then"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 118 - line 67 - delete "bivyl", insert "biary"

Col. 119 - line 3 - delete "ihto", insert "into"

Col. 120 - line 61 - delete "meani", insert "mean± "

Col. 123 - line 54 - delete "euthanieed", insert "euthanized"

Col. 125 - line 51 - delete "hydroxanic", insert "hydroxamic"

Col. 125 - line 56 - delete "orheteroaryl", insert "or heteroaryl"

Col. 126 - line 10 - delete "heterorryl", insert "heteroaryl"

Col. 126 - line 23 - delete "cycloallyl", insert "cycloalkyl"

Col. 126- line 23 - delete "cycloheteloalkyl", insert "cycloheteroalkyl"

Col. 126 - line 44 - delete "perfluoroaikyl", insert "perfluoroalkyl"

Col. 126 - line 52 - delete "cycloaalyl", insert "cycloalkyl"

Col. 127 - line 41 - delete benzetsulfonyl" , insert "benzenesulfonyl"

Col. 127 - line 44 - delete "benzamnide", insert "benzamide"

Col. 127 - line 59 - delete "cabamoyl", insert "carbamoyl"

UNITED STATES PATENT AND TRADEMARK OFFICE
CERTIFICATE OF CORRECTION

PATENT NO. : 5,929,097

DATED : July 27, 1999

INVENTOR(S) : Jeremy I. Levin, et al

It is certified that error appears in the above-identified patent and that said Letters Patent is hereby corrected as shown below:

Col. 127 - line 62 - delete "pyrdin", insert "pyridin"

Col. 128 - line 1 - delete "anino", insert "amino"

Col. 129 - line 8 - delete "carbanoyl", insert "carbamoyl"

Col. 129 - line 43 - delete "trifluoromthyl", insert "trifluoromethyl"

Col. 129 - line 63 - delete "diethyiaminomethyl", insert "diethylaminomethyl"

Col. 130 - line 8 - delete "arnino", insert "amino"

Col. 130 - line 65 - delete "isophthalamnic", insert "isophthalamic"

Col. 132 - line 57 - delete "medtod", insert "method"

Signed and Sealed this

Third Day of April, 2001

Attest:

NICHOLAS P. GODICI

Attesting Officer

Acting Director of the United States Patent and Trademark Office